United States Patent
Minassian et al.

(10) Patent No.: US 10,577,657 B2
(45) Date of Patent: Mar. 3, 2020

(54) MECP2E1 GENE

(71) Applicants: The Hospital For Sick Children, Toronto (CA); Centre for Addiction and Mental Health, Toronto (CA)

(72) Inventors: Berge A. Minassian, Toronto (CA); John B. Vincent, Toronto (CA)

(73) Assignees: The Hospital For Sick Children, Toronto (CA); Centre for Addiction and Mental Health, Toronto (CA)

(*) Notice: Subject to any disclaimer, the term of this patent is extended or adjusted under 35 U.S.C. 154(b) by 0 days.

(21) Appl. No.: 15/914,770

(22) Filed: Mar. 7, 2018

(65) Prior Publication Data

US 2018/0265926 A1 Sep. 20, 2018

Related U.S. Application Data

(63) Continuation of application No. 15/429,143, filed on Feb. 9, 2017, now abandoned, which is a continuation of application No. 14/100,889, filed on Dec. 9, 2013, now Pat. No. 9,605,314, which is a continuation of application No. 12/657,559, filed on Jan. 21, 2010, now Pat. No. 8,637,236, which is a continuation-in-part of application No. 11/352,153, filed on Feb. 9, 2006, now Pat. No. 7,670,773, which is a continuation of application No. PCT/CA2005/000198, filed on Feb. 17, 2005.

(60) Provisional application No. 60/544,311, filed on Feb. 17, 2004.

(51) Int. Cl.

| *A61K 47/26* | (2006.01) |
| *C12Q 1/6883* | (2018.01) |
| *C07K 14/47* | (2006.01) |
| *G01N 33/68* | (2006.01) |
| *A61K 38/17* | (2006.01) |
| *A61K 38/00* | (2006.01) |
| *A61K 48/00* | (2006.01) |

(52) U.S. Cl.
CPC ........ *C12Q 1/6883* (2013.01); *A61K 38/1709* (2013.01); *C07K 14/47* (2013.01); *G01N 33/6896* (2013.01); *H05K 999/99* (2013.01); *A61K 38/00* (2013.01); *A61K 48/00* (2013.01); *C12Q 2600/156* (2013.01); *G01N 2500/00* (2013.01); *G01N 2800/28* (2013.01)

(58) Field of Classification Search
None
See application file for complete search history.

(56) References Cited

U.S. PATENT DOCUMENTS

| 6,709,817 B1 | 3/2004 | Zoghbi et al. |
| 7,670,773 B2 | 3/2010 | Minassian et al. |
| 2002/0137067 A1 | 9/2002 | Beaudet et al. |
| 2003/0082606 A1 | 5/2003 | Lebo et al. |
| 2005/0227229 A1 | 10/2005 | Lebo et al. |
| 2006/0194257 A1 | 8/2006 | Minassian et al. |
| 2009/0098565 A1 | 4/2009 | Minassian et al. |
| 2017/0137887 A1 | 5/2017 | Minassian et al. |

FOREIGN PATENT DOCUMENTS

| JP | 2001-292775 | 10/2001 |
| WO | WO 02/068579 A2 | 9/2002 |
| WO | WO 2005/078099 A1 | 8/2005 |

OTHER PUBLICATIONS

ThermoFisher Scientific, 2018.*
Ahren, The Scientist, 1995.*
Traynor et al., BMC Medical Genetics, 2002, 3: 1-15.*
De Silva et al., J. Chromatography B, 2000, 741: 3-13.*
Lay et al., Clin. Chem., 1997, 43: 2262-2267.*
Office Action for Japanese Application No. 2006-553398, dated Aug. 4, 2010.
Office Action for U.S. Appl. No. 12/313,251, dated Sep. 1, 2010.
Liu, J. and G. Baynam, "Cornelia deLange Syndrome," *Adv. Exp. Med. Biol.* 685: 111-123, Abstract (2010) (month not available).
De Brouwer, A.P., et al., "PRPS1 Mutations: Four Distinct Syndromes and Potential Treatment," *Am. J. Hum. Genet.*, 86: 506-518, Abstract (Apr. 2010).
Office Action, U.S. Appl. No. 12/313,251; dated Jul. 24, 2012.
Office Action for U.S. Appl. No. 11/352,153, dated May 3, 2007.
Office Action for U.S. Appl. No. 11/352,153, dated Nov. 30, 2007.
Office Action for U.S. Appl. No. 11/352,153, dated May 2, 2008.
Office Action for U.S. Appl. No. 11/352,153, dated Oct. 2, 2008.
Office Action for U.S. Appl. No. 11/352,153, dated Dec. 30, 2008.
Office Action for U.S. Appl. No. 11/352,153, dated Jul. 31, 2009.
Office Action for U.S. Appl. No. 11/352,153, dated Oct. 20, 2009.
Office Action for U.S. Appl. No. 12/313,251, dated Mar. 18, 2010.
Schollen, et al., "Gross Rearrangements in the MECP2 Gene in Three Patients with Rett Syndrome: Implications for Routine Diagnosis of Rett Syndrome," *Human Mutation*, vol. 22, pp. 116-120 (2003).
Office Action for U.S. Appl. No. 12/313,251, dated Feb. 22, 2011.
Final Office Action cited in U.S. Appl. No. 12/313,251, dated Oct. 21, 2011.
Office Action cited in U.S. Appl. No. 12/313,251, dated Feb. 1, 2012.
Bloecker, H., et al., Accession No. BX538060, GENBANK Database, [online] Jun. 17, 2003, [retrieved on May 17, 2006] retrieved from the Internet http://www.ncbi.nlm.nih.gov/entrez/viewer.fcgi?db=nucleotide&val=31874178.
Bloecker, H., et al., Access on No. CAD97991, GENPEPT Database, [online] Jun. 17, 2003, [retrieved on May 17, 2006] retrieved from the Internet http://www.ncbi.nlm.nih.gov/entrez/viewerfegi?db=protein&val-31874179.

(Continued)

Primary Examiner — Ileana Popa
(74) Attorney, Agent, or Firm — Foley & Lardner LLP

(57) ABSTRACT

The invention is a novel MECP2E1 splice variant and its corresponding polypeptide. The invention also includes methods of using these nucleic acid sequences and proteins in medical diagnosis and treatment of neuropsychiatric disorders or development disorders.

6 Claims, 10 Drawing Sheets
Specification includes a Sequence Listing.

(56) References Cited

OTHER PUBLICATIONS

Kass, S.U., et al., Accession No. AF051768, GENBANK Database [online] Jan. 5, 1999 [retrieved on May 17, 2006] retrieved from the Internet http://www. ncbi .n 1 m nih.gov/entrez/viewer.fegi?db=nucleotide&val=4105998.

Kass, S.U., et al. Accession No. AAD02651, GENPEPT Database, [online] Jan. 5, 1999 [retrieved on May 17, 2006] retrieved from the Internet http:/www.ncbi_.nih._gov/entreevi ewer Segi?db=protein&val=4105999.

Coenraads, M., "Researchers Confirm Novel Form of the Rett Syndrome Protein," Rett Syndro Research Foundation: Press Releases: Mar. 22, 2004, pp. 1-2, [retrieved on May 17, 2006] Retrieved from the Internet http://www.rsrforg/about_rsrf/1.5.2.html.

Che, R. Z., et al., "Deficiency of Methyl-CpG Binding Protein-2 in CNS Neurons Results in a Rett-like Phenotype in Mice," *Nature Genetics*, 27: 327-331 (2001).

Kriaucionis, S., et al., "The Major Form of MeCP2 has a Novel N-terminus Genera ed by Alternative Splicing," *Nucleic Acids Research*, 32(5): 1818-1823 (2004).

Evans, J. C., et al., "Variation in Exon 1 Coding Region and Promotor of MECP2 in Rat Syndrome and Controls," *European Journal of Human Genetics*, 13: 124-126 (2005).

Kim, S., et al., Novel de novo Nonsense Mutation of MECP2 in a Patient with Rett S Human Mutation, Mutation in Brief #307 Online (2000).

Erlandson, A., et al., "Multiplex Ligation-Dependent Probe Amplification (MLPA) Detects Large Deletions in the MECP2 Gene of Swedish Rett Syndrome Patients," *Genetic Testing*, 7(4): 329-332 (2003).

Bienvenu, T., et al., "MECP2 Mutations Account for most Cases of Typical Form s of Rett Syndrome," *Human Molecular Genetics*, 9(9): 1377-1384 (2000).

Nicolao, P., et al., "DHPLC Analys s of the MECP2 Gene in Italian Rett Patients," *Human Mutation*, 18: 132-140 ( 2001).

Mnatzakanian, G. N., et al, "A Preiously Unidentified MECP2 Open Reading Frame Defines a New Protein Isoform Relevant to Rett Syndrome," *Nature Genetics*, 36(4): 339-341 (2004).

Vacca. M., et al, "Mutation Analysis fo the MECP2 Gene in British and Italian Rett Syndrome Fales," *J. Mol Med.*, 78: 648-655 (2001).

Cheadle, J. P., et al., "Long-Read Sequence Analysis of the MECP2 Gene in Rett Syndrome Patients: Correlation of Disease Severity with Mutation Type and Location," *Human Molecular Genetics*, 9(7): 1119-1129 (2000).

Bourdon, V., et al., "A Detailed Analysis of MECP2 Gene: Prevalence of Recurrent Mutations and Gross DNA Rearrangements in Rett Syndrome Patients," *Hum. Genet*, 108: 43-50 (2001).

Charman, T., et al., "Dimensional Phenotypic Analysis and Functional Categorisation of Mutations Reveal Novel Genotype-Phenotype Associations in Rett Syndrome," *European Journal of Human Genetics*, 13: 1121-1130 (2005).

Christodoulou, J., et al., "RettBASE: The USA MECP2 Variation Database—A New Mutation Database in Evolution," *Human Mutation*, 21: 466-472 (2003).

Amir, R. E., et al., "Rett Syndrome is Caused by Mutations in X-Linked MECP2, Encoding Methyl-CpG-Binding Protein 2," *Nature Genetics*, 23: 185-188 (1999).

Willard, H. F. and Hendrich, B.D., "Breaking the Silence in Rett Syndrome," *Nature Genetics*, 23: 27-128 (1999).

Buyse, I. M. and Hendrich, B.D., "Diagnostic Testing for Rett Syndrome by DHPLC and Direct Sequencing Analysis of the MECP2 Gene: Identification of Several Novel Mutations and Polymorphisms," *Am. J. Hum. Genet.*, 67: 1428-1436 (2000).

Thistlethwaite, W. A., et al., "Rapid Genotyping of Common MeCP2 Mutations with an Electronic DNA Microchip Using Serial Differential Hybridiztion," *Journal of Molecular Diagnostics*, 5(2): 21-126 (2003).

Hammer, S., et al., "The Phenotypic Consequences of MECP2 Mutations Extend Beyond Rett Syndrome." *Mental Retardation and Development Disabilities Research Reviews*, 8: 94-98 (2002).

Meloni, I., et al., "A Mutation in the Rat Syndrome Gene, MECP2, Causes X-Linked Mental Retardation and Progresive Spasticity in Males," *Am. J. I-Turn. Genet.*, 67: 982-985 ( 2000).

Samaco, R. C., et al., "Multiple Pathways Regula e MeCP2 Expression in Normal Brain Development and Exhibit Defects in Autism-Spectrum Disorders," *Human Molecular Genetics*, 3(6): 629-639 (2004).

Beyer, K. S., et al. "Mutation Analysis Analysis of the Coding Sequence of the MECP2 Gene in Infantile Autism," *Hum. Genet.*, 111: 305-309 (2002).

Shi, J., et al., Detection of Heterozygous Deletions and Duplications in the MECP2 Gene in Rett Syndrome by Robust Dosage PCT (RD-PCR), Human Mutation, Mutation in Brief #809 Online, 7 pages (2005).

Fyfe, S., et al., "InterRett and RettBASE: International Rett Syndrome Association Da abases for Rett Syndrome." *Journal of Child Neurology*, 18: 709-713 (Oct. 2003).

Archer, H. L., et al., "Gross Rearrang ments of the MECP2 Gene Are Found in Both Classical an Atypical Rett Syndrome Patients," *J Med. Genet.*, 43: 451-456 (2006).

Van Esch, H., et al., "Duplication of the MECP2 Region is a Frequent Cause of Severe Mental Retardation and Progressive Neurological Systems in Males," *Am. J. Hum. Genet.*, 77: 442-453 (Jul. 2005).

Boulanger, S., et al., "Evaluation of the Multiplex Ligation-Dependent Probe Amplification (MLPA) Technology in the Diagnosis of Rett Syndrome," *Am. J. Hum, Genet.*, 73 (5): 572 (Nov. 2003).

Aber, K. M., et al., "Methly-CpG-Binding Protein 2 Is Localized in the Postsynapt e Compartment: An Immunchemical Study of Subcellular Fractions," *Neuroscience*, 116: 77-80 (2003).

Bienvenu, T., et al., "ARX, a Novel Prd-class-homeobox Gene Highly Expressed in the Telencephalon, Is Mutated in X-linked Mental Retrdation," *Hum. Mol. Gen.*, 11(8): 981-991 (2002).

Brown, L. Y. and Brown, S. A., "Alanine Tracts: The Expanding Story of Human Illness and Trinucleotide Repeats," *Trends Genet.*, 20(1): 51-58 (2004).

Cohen, D., et al., 1VIECP2 Mutation in a Boy With Language Disorder and Schizophrenia, *A Psychiatry, Letters to the Editor*, 159(1): 148-149 (Jan. 2002).

Collins, A. L., et al., "Mild Overexpression of MeCP2 Causes a Progress ve Neurological Disorder in Mice," *Hum. Mol. Gen.*, 13(21): 2679-2689 (Sep. 2004).

Coy, J. F., et al., "A Complex Pattern of Evolutionary Conservation and Alternative Polyadenylation withiin the Long 3'-Untranslated Region of the Methy-CpG-Binding Protein 2 Gene (MeCP2) Suggests a Regulatory Role in Gene Expression," *Hum. Mol. Gentics*, 8(7): 1253-1262 (1999).

D'Esposito, M., et al., "Isolation, Physical Mapping and Northern Analysis of the X-Linked Human Gene Encoding Methyl CpG-Binding Protein, MECP2," *Mamm. Genorne.*, 7, 533-535 (1996).

Groskov, K., et al., "Screening of the ARX Gene in 682 Retarded Males," *Eur. J. Hum. Genet.*, 12: 701-705 (Jun. 2004).

Hagberg, B., "Clinical Manifestations and States of Rett Syndrome," *Mental Retardation and Developmental Disabilities Research Reviews*, 8:61-65 (2002, month not available).

Hardingham, G. E., et al., "A Calcium Microdomain Near NMDA Receptors: On Switch for ERK-dependent Synapse-to-Nucleus Communication," *Nature Neuroscience*, 4(6): 565-566 (Jun. 2001).

Inoue, K. and Keegstra, K., "A Polyglycine Stretch is Necessary for Proper Targeting of the Protein Translocation Channel Precursor to the Outer Envelope Membrane of Chloroplasts," *The Plant Journal*, 34: 661-669 (2003).

Miltenberger-Miltenyi, G. and Laccone, F., "Mutations and Polymorphisms in the Human Methyl CpG-Binding Protein MECP2," *Human Mutation*, 22: 107-115 (2003).

Orrico, A., et al., "M_ECP2 Mutation in Male Patients with Non-specific X-linked Mental Retardation," *FEBS Letters*, 481: 285-288 (2000).

(56) References Cited

OTHER PUBLICATIONS

Reichwald, K., et al., "Comparative Sequence Analysis of the MECP2-Locus in Human and Mouse Reveals New Transcribed Regions," *Mamm. Genorne.*, 11: 182-190 (2000).
Schouten, J. P., et al., "Relative Quantification of 40 Nucleic Acid Sequences by Multiplex Ligation-Dependent Probe Amplification," *Nucleic Acids Research*, 30(12): e57, 13 pages (2002).
Shahbazian, M. D., et al., "Insight into Rett Syndrome: MeCP2 Levels Display Tissue-and-Cell-Specific Differenes and Correlate with Neuronal Maturation," *Hum. Mol. Gene.*, 11(2): 115-124 (2002).
Stancheva, I., et al., "A Mutant form of MeCP2 Protein Associated with Human Rett Syndrome Cannot be Displaced from Methylated DNA by Notch in *Xenopus* Embryos," *Hifol. Cell.*, 12: 425-435 (2003).
Utsch, B., et al., "A Novel Stable Polyalanine [Poly(A)] Expansion in the HOXA13 Gene Associated with Hand-Foot-Genital Syndrome: Proper Function of Poly(A)—Harbouring Transcription Factors Depends on a Critical repeat Length?," *Hum. Genet.* 110:488-494 (Apr. 2002).
Muhle, R., et al., "The Genetics of Autism," *Pediatrics*, 113:472-486 (May 2004).
Kato, M., "A New Paradigm for West Syndrome Based on Molecular and Cell Biology," *Epilespy Research*, 70:S87-S95 (2006).
Abdolma eky, H.M. et al., "Genetics and Epigenetics in Major Psychiatric Disorders: Dilemmas, Achievements, Applications, and Future Scope," *Am. J. Pharmacogenomics*, 5:149-160 (2006).
Hardy, J., and Gwinn-Hardy, K., Genetic Classification of Primary Neurodegereative Disease, *Science*, 282:1075-1079 (1998).
Amir, R.E., et al., "Mutations in Exon 1 of MECP2 Are a Rare Cause of Rett Syndrome" *J. Med. Genet.* 42: e15, 4 pages (2005).
Kleefstra, T., et al., "MECP2 Analysis in Mentally Retarded Patients: Implications for Routine DNA Diagnostis" *Eur. J. Hum. Genet.* 12:24-28 (2004).
Mnatzakanian, G.N., et al., "A Previously Unidentified MECP2 Open Reading Frame Defines a New Protein Isoform Relevant to Rett Syndrome," *Nat. Genet.* 36: 339-341 (2004).
Peippo, M.M., et al., "Pitt-Hopkins Syndrome in Two Patients and Further Definition of the Phenotype," *Clinical Dysmorphology*, 15: 47-54 (2006).
Poirier, K., et al., "Mutations in Exon 1 of MECP2B are Not a Common Cause of X-Linked Mental Retardation in Males," *European J. Hum. Genet.* 13:523-524 (2005).
Ylisaukko-ojo, T., et a ., "MECP2 Mutation Analysis in Pat ents with Mental Retarda ion," *Am. I Med. Genet.* 132A: 121-124 (2005).
Notification of Transmittal of the International Search Report and the Written Opinion of the International Searching Authority, or the Declaration for International Application No. PCT/CA2005/000198, dated Jul. 4, 2005.
International Preliminary Report on Patentability for International Application No. PCT/CA2005/000198, dated Aug. 31, 2006.
Office Action for U.S. Appl. No. 11/352,153, dated Nov. 29, 2006.
Notice of Allowance issued in related U.S. Appl. No. 12/313,251, dated Sep. 30, 2016.
Database GenBank [online], Accession No. NM_004992 http://www.ncbi.nlm.nih.gov/sviewer/viewer.fcgi?val=7710148&sat=OLD03&satkey=6827913 Dec. 21, 2003 uploaded, Leonard, H. et al., Definition: *Homo sapiens* methyl CpG binding protein 2 (Rett syndrome) (MECP2), mRNA. [retrieved on Jul. 27, 2010].
Notice of Reasons for Rejection issued in related Japanese Patent Application No. 2015-147517, dated Jun. 23, 2016.
Office Action issued in related U.S. Appl. No. 12/313,251, dated Jul. 6, 2016.
Office Action issued in related U.S. Appl. No. 12/313,251, dated Jan. 13, 2016.
Office Action issued in related U.S. Appl. No. 12/313,251, dated Aug. 27, 2015.
Sawada, et al,. "Detection of Triplet Repeat Expansion in the Human Genome by Use of Hybridization signal intensity," *Analytical Biochemistry*, vol. 286, pp. 59-66 (2000).
Yusufazai et al., "Functional consequences of Rett syndrome mutations of human MeCP2," *Nucleic Acids Research*, vol. 28. No. 21; pp. 4172-4179 (2000).
U.S. Office Action issued in related U.S. Appl. No. 12/313,251, dated Feb. 4, 2014.
U.S. Office Action issued in related U.S. Appl. No. 12/313,251, dated Apr. 22, 2015.
Japanese Notice of Reasons for Rejection issued in related Japanese Patent Application No. 2006-553398, dated Jan. 28, 2015.
Notice of Reasons for Rejection issued in related Japanese Patent Application No. 2006-553398, dated Apr. 28, 2014.
Opitz, Am. J. Med. Genet. vol. 130B, No. Sep. 15, 2004, p. 104 [Abstract].
Office Action issued in related U.S. Appl. No. 12/313,251, dated Feb. 4, 2014.
Gauthier, et al., "Clinical Stringency Greatly improves Mutation Detection in Rett Syndrome," *Can. J. Neurol. Sci.*, vol. 32, pp. 321-326 (2005).
Non-Final Office Action issued in related U.S. Appl. No. 15/421,156, dated Sep. 8, 2017 (US 2017/0137887).
Office Action issued in co-pending U.S. Appl. No. 15/914,800, dated Nov. 16, 2018.

\* cited by examiner

MECP2A  MECP2B e)

FIG. 1F

| Protein Name | Species | N-Terminus Sequence | Accession |
|---|---|---|---|
| MeCP2A | H. sapiens | MVAGMLGL R | Y12643 |
| MeCP2B | H. sapiens | MAAAAAAA------------------PSGGGGGEEERL | BX538060 |
| Mecp2B (predicted) | P. troglodytes | MAAAAAAA------------------PSGGGGGEEERL | AACZ01193635 |
| Mecp2B | M. musculus | MAAAAATAAAAAA-----------PSGGGGGEEERL | BU817697 |
| Mecp2B (predicted) | R. norvegicus | MAAAAAAAAAAAAAAAAAAAAAAPSGGGGGEEERL | AC134952 |
| Mecp2B (predicted) | F. catus | MAAAAAAA------------------PSGGGGGEEERL | AC133395 |
| Mecp2 (ARBP) | G. gallus | MAAAAAAAA-------------------GG-----EERL | Y16166 |
| Mecp2 | X. laevis | MAAA-------------------------PSG----EERL | AF106951 |
| Mecp2 | D. rerio | MAAA-------------------------ESG----EERL | AY796900 |
| Mecp2 (predicted) | F. rubripes | MAA---------------------------VESG----EE | Ensembl contig 2476 |
| ERK1 (MAPK3) | H. sapiens | MAAAAAA---------------------QGGGG-E | NM_002746 |
| Erk1 (Mapk3) | M. musculus | MAAAAAA---------------------P-GGGGG-E | BC029712 |
| Erk1 (Mapk3) | R. norvegicus | MAAAAAA---------------------P-GGGGG-E | NM_017347 |

A.

B.

C.

```
                        SEQUENCE LISTING

<160> NUMBER OF SEQ ID NOS: 55

<210> SEQ ID NO 1
<211> LENGTH: 10182
<212> TYPE: DNA
<213> ORGANISM: Homo sapiens

<400> SEQUENCE: 1
ccggaaaatg gccgccgccg ccgccgccgc gccgagcgga ggaggaggag gaggcgagga      60
ggagagactg ctccataaaa atacagactc accagttcct gctttgatgt gacatgtgac     120
tccccagaat acaccttgct tctgtagacc agctccaaca ggattccatg gtagctggga     180
tgttagggct cagggaagaa aagtcagaag accaggacct ccagggcctc aaggacaaac     240
ccctcaagtt taaaaaggtg aagaaagata agaaagaaga gaaagagggc aagcatgagc     300
ccgtgcagcc atcagcccac cactctgctg agcccgcaga ggcaggcaaa gcagagacat     360
cagaagggtc aggctccgcc ccggctgtgc cggaagcttc tgcctccccc aaacagcggc     420
gctccatcat ccgtgaccgg ggacccatgt atgatgaccc caccctgcct gaaggctgga     480
cacggaagct taagcaaagg aaatctggcc gctctgctgg gaagtatgat gtgtatttga     540 tcaatccccca gggaaaagcc tttcgctcta aagtggagtt gattgcgtac ttcgaaaagg     600
taggcgacac atccctggac cctaatgatt ttgacttcac ggtaactggg agagggagcc     660
cctcccggcg agagcagaaa ccacctaaga agcccaaatc tcccaaagct ccaggaactg     720
gcagaggccg gggacgcccc aaagggagcg gcaccacgag acccaaggcg gccacgtcag     780
agggtgtgca ggtgaaaagg gtcctggaga aaagtcctgg gaagctcctt gtcaagatgc     840
cttttcaaac ttcgccaggg ggcaaggctg aggggggtgg ggccaccaca tccacccagg     900
tcatggtgat caaacgcccc ggcaggaagc gaaaagctga ggccgaccct caggccattc     960
ccaagaaacg gggccgaaag ccggggagtg tggtggcagc cgctgccgcc gaggccaaaa    1020
agaaagccgt gaaggagtct tctatccgat ctgtgcagga gaccgtactc cccatcaaga    1080
agcgcaagac ccgggagacg gtcagcatcg aggtcaagga agtggtgaag cccctgctgg    1140
tgtccaccct cggtgagaag agcgggaaag gactgaagac ctgtaagagc cctgggcgga    1200
```

```
aaagcaagga gagcagcccc aagggcgca gcagcagcgc ctcctcaccc ccaagaagg      1260 agcaccacca ccatcaccac cactcagagt ccccaaaggc ccccgtgcca ctgctcccac    1320
ccctgccccc acctccacct gagcccgaga gctccgagga ccccaccagc ccccctgagc    1380
cccaggactt gagcagcagc gtctgcaaag aggagaagat gccagagga ggctcactgg     1440 agagcgacgg ctgccccaag gagccagcta agactcagcc cgcggttgcc accgccgcca    1500
cggccgcaga aaagtacaaa caccgagggg agggagagcg caaagacatt gtttcatcct    1560
ccatgccaag gccaaacaga gaggagcctg tggacagccg gacgcccgtg accgagagag    1620
ttagctgact ttacacggag cggattgcaa agcaaaccaa caagaataaa ggcagctgtt    1680
gtctcttctc cttatgggta gggctctgac aaagcttccc gattaactga aataaaaaat    1740
attttttttt ctttcagtaa acttagagtt tcgtggcttc agggtgggag tagttggagc    1800
attggggatg ttttcttac cgacaagcac agtcaggttg aagcctaac cagggccaga      1860 agtagctttg cacttttcta aactaggctc cttcaacaag gcttgctgca gatactactg    1920
accagacaag ctgttgacca ggcacctccc ctcccgccca aaccttttccc ccatgtggtc   1980 gttagagaca gagcgacaga gcagttgaga ggacactccc gttttcggtg ccatcagtgc    2040
cccgtctaca gctcccccag ctcccccac ctcccccact cccaaccacg ttgggacagg     2100
gaggtgtgag gcaggagaga cagttggatt ctttagagaa gatggatatg accagtggct    2160
atggcctgtg cgatcccacc cgtggtggct caagtctggc cccacaccag ccccaatcca    2220
aaactggcaa ggacgcttca caggacagga aagtggcacc tgtctgctcc agctctggca    2280
tggctaggag gggggagtcc cttgaactac tgggtgtaga ctggcctgaa ccacaggaga    2340
ggatggccca gggtgaggtg gcatggtcca ttctcaaggg acgtcctcca acgggtggcg    2400
ctagaggcca tggaggcagt aggacaaggt gcaggcaggc tggcctgggg tcaggccggg    2460
cagagcacag cggggtgaga gggattccta atcactcaga gcagtctgtg acttagtgga    2520
caggggaggg ggcaaagggg gaggagaaga aaatgttctt ccagttactt tccaattctc    2580
ctttagggac agcttagaat tatttgcact attgagtctt catgttccca cttcaaaaca    2640
aacagatgct ctgagagcaa actggcttga attggtgaca tttagtccct caagccacca    2700
gatgtgacag tgttgagaac tacctggatt tgtatatata cctgcgcttg ttttaaagtg    2760
ggctcagcac atagggttcc cacgaagctc cgaaactcta agtgtttgct gcaatttttat   2820 aaggacttcc tgattggttt ctcttctccc cttccatttc tgccttttgt tcatttcatc    2880
ctttcacttc ttttcccttcc tccgtcctcc tccttcctag ttcatccctt ctcttccagg   2940
cagccgcggt gcccaaccac acttgtcggc tccagtcccc agaactctgc ctgcccttttg   3000 tcctcctgct gccagtacca gccccaccct gttttgagcc ctgaggaggc cttgggctct    3060
gctgagtccg acctggcctg tctgtgaaga gcaagagagc agcaaggtct tgctctccta    3120
ggtagccccc tcttccctgg taagaaaaag caaaaggcat ttcccaccct gaacaacgag    3180 cctttttcacc cttctactct agagaagtgg actggaggag ctgggcccga tttggtagtt   3240
gaggaaagca cagaggcctc ctgtggcctg ccagtcatcg agtggcccaa caggggctcc    3300
atgccagccg accttgacct cactcagaag tccagagtct agcgtagtgc agcagggcag    3360
tagcggtacc aatgcagaac tcccaagacc cgagctggga ccagtacctg gtccccagc     3420 ccttcctctg ctccccctttt tccctcggag ttcttcttga atggcaatgt tttgcttttg   3480
ctcgatgcag acaggggggcc agaacaccac acatttcact gtctgtctgg tccatagctg   3540
tggtgtaggg gcttagaggc atgggcttgc tgtgggtttt taattgatca gttttcatgt    3600
```

```
gggatcccat cttttaacc tctgttcagg aagtccttat ctagctgcat atcttcatca    3660
tattggtata tccttttctg tgtttacaga gatgtctctt atatctaaat ctgtccaact    3720
gagaagtacc ttatcaaagt agcaaatgag acagcagtct tatgcttcca gaaacaccca    3780
caggcatgtc ccatgtgagc tgctgccatg aactgtcaag tgtgtgttgt cttgtgtatt    3840
tcagttattg tccctggctt ccttactatg gtgtaatcat gaaggagtga acatcatag     3900 aaactgtcta gcacttcctt gccagtcttt agtgatcagg aaccatagtt gacagttcca    3960
atcagtagct taagaaaaaa ccgtgtttgt ctcttctgga atggttagaa gtgagggagt    4020
ttgccccgtt ctgtttgtag agtctcatag ttggactttc tagcatatat gtgtccattt    4080
ccttatgctg taaaagcaag tcctgcaacc aaactcccat cagcccaatc cctgatccct    4140
gatcccttcc acctgctctg ctgatgaccc cccagcttc acttctgact cttccccagg     4200
aagggaaggg gggtcagaag agagggtgag tcctccagaa ctcttcctcc aaggacagaa    4260
ggctcctgcc cccatagtgg cctcgaactc ctggcactac caaggacac ttatccacga     4320 gagcgcagca tccgaccagg ttgtcactga aagatgtttt atttggtca gttgggtttt     4380 tatgtattat acttagtcaa atgtaatgtg gcttctggaa tcattgtcca gagctgcttc    4440
cccgtcacct gggcgtcatc tggtcctggt aagaggagtg cgtggcccac caggcccccc    4500
tgtcacccat gacagttcat tcagggccga tggggcagtc gtggttggga acacagcatt    4560
tcaagcgtca ctttatttca ttcgggcccc acctgcagct ccctcaaaga ggcagttgcc    4620
cagcctcttt cccttccagt ttattccaga gctgccagtg gggcctgagg ctccttaggg    4680
ttttctctct atttcccct ttcttcctca ttccctcgtc tttcccaaag gcatcacgag      4740
tcagtcgcct ttcagcaggc agccttggcg gtttatcgcc ctggcaggca ggggccctgc    4800
agctctcatg ctgcccctgc cttggggtca ggttgacagg aggttggagg gaaagcctta    4860
agctgcagga ttctcaccag ctgtgtccgg cccagttttg gggtgtgacc tcaatttcaa    4920
ttttgtctgt acttgaacat tatgaagatg ggggcctctt tcagtgaatt tgtgaacagc    4980
agaattgacc gacagctttc cagtacccat ggggctaggt cattaaggcc acatccacag    5040
tctcccccac ccttgttcca gttgttagtt actacctcct ctcctgacaa tactgtatgt    5100
cgtcgagctc cccccaggtc taccctccc ggccctgcct gctggtgggc ttgtcatagc     5160
cagtgggatt gccggtcttg acagctcagt gagctggaga tacttggtca cagccaggcg    5220
ctagcacagc tcccttctgt tgatgctgta ttcccatatc aaaagacaca ggggacaccc    5280
agaaacgcca catcccccaa tccatcagtg ccaaactagc caacggcccc agcttctcag    5340
ctcgctggat ggcggaagct gctactcgtg agcgccagtg cgggtgcaga caatcttctg    5400
ttgggtggca tcattccagg cccgaagcat gaacagtgca cctgggacag ggagcagccc    5460
caaattgtca cctgcttctc tgcccagctt ttcattgctg tgacagtgat ggcgaaagag    5520
ggtaataacc agacacaaac tgccaagttg ggtggagaaa ggagtttctt tagctgacag    5580
aatctctgaa tttaaatca cttagtaagc ggctcaagcc caggagggag cagagggata     5640
cgagcggagt cccctgcgcg ggaccatctg gaattggttt agcccaagtg gagcctgaca    5700
gccagaactc tgtgtccccc gtctaaccac agctccttt ccagagcatt ccagtcaggc     5760
tctctgggct gactgggcca ggggaggtta caggtaccag ttcttaaga agatctttgg     5820 gcatatacat ttttagcctg tgtcattgcc ccaaatggat tcctgtttca agttcacacc    5880
tgcagattct aggacctgtg tcctagactt cagggagtca gctgtttcta gagttcctac    5940
```

```
catggagtgg gtctggagga cctgcccggt gggggggcag agccctgctc cctccgggtc    6000
ttcctactct tctctctgct ctgacgggat ttgttgattc tctccatttt ggtgtctttc    6060
tcttttagat attgtatcaa tctttagaaa aggcatagtc tacttgttat aaatcgttag    6120
gatactgcct cccccagggt ctaaaattac atattagagg ggaaaagctg aacactgaag    6180
tcagttctca acaatttaga aggaaaacct agaaacatt tggcagaaaa ttacatttcg     6240
atgttttga atgaatacga gcaagctttt acaacagtgc tgatctaaaa atacttagca    6300
cttggcctga gatgcctggt gagcattaca ggcaagggga atctggaggt agccgacctg    6360
aggacatggc ttctgaacct gtcttttggg agtggtatgg aaggtggagc gttcaccagt    6420
gacctggaag gcccagcacc accctccttc ccactcttct catcttgaca gagcctgccc    6480
cagcgctgac gtgtcaggaa aacccccagg gaactaggaa ggcacttctg cctgaggggc    6540
agcctgcctt gcccactcct gctctgctcg cctcggatca gctgagcctt ctgagctggc    6600
ctctcactgc ctccccaagg cccctgcct gccctgtcag gaggcagaag gaagcaggtg     6660
tgagggcagt gcaaggaggg agcacaaccc ccagctcccg ctccgggctc cgacttgtgc    6720
acaggcagag cccagaccct ggaggaaatc ctacctttga attcaagaac atttggggaa    6780
tttgaaatc tctttgcccc caaaccccca ttctgtccta cctttaatca ggtcctgctc     6840
agcagtgaga gcagatgagg tgaaaaggcc aagaggtttg ctcctgcccc actgatagcc    6900
cctctccccg cagtgtttgt gtgtcaagtg gcaaagctgt tcttcctggt gaccctgatt    6960
atatccagta acacatagac tgtgcgcata ggcctgcttt gtctcctcta tcctgggctt    7020
ttgttttgct ttttagtttt gcttttagtt tttctgtccc ttttatttaa cgcaccgact    7080
agacacacaa agcagttgaa ttttttatata tatatctgta tattgcacaa ttataaactc   7140
attttgcttg tggctccaca cacacaaaaa aagacctgtt aaaattatac ctgttgctta   7200
attacaatat ttctgataac catagcatag acaagggaa aataaaaaaa gaaaaaaaag     7260
aaaaaaaac gacaaatctg tctgctggtc acttcttctg tccaagcaga ttcgtggtct    7320
tttcctcgct tctttcaagg gctttcctgt gccaggtgaa ggaggctcca ggcagcaccc    7380
aggttttgca ctcttgtttc tcccgtgctt gtgaaagagg tcccaaggtt ctgggtgcag    7440
gagcgctccc ttgacctgct gaagtccgga acgtagtcgg cacagcctgg tcgccttcca    7500
cctctgggag ctggagtcca ctggggtggc ctgactcccc cagtccccctt cccgtgacct   7560
ggtcagggtg agcccatgtg gagtcagcct cgcaggcctc cctgccagta gggtccgagt    7620
gtgtttcatc cttcccactc tgtcgagcct ggggctggga gcggagacgg gaggcctggc    7680
ctgtctcgga acctgtgagc tgcaccaggt agaacgccag ggaccccaga atcatgtgcg    7740
tcagtccaag gggtcccctc caggagtagt gaagactcca gaaatgtccc tttcttctcc    7800
cccatcctac gagtaattgc atttgctttt gtaattctta atgagcaata tctgctagag    7860
agtttagctg taacagttct ttttgatcat cttttttaa taattagaaa caccaaaaaa     7920
atccagaaac ttgttcttcc aaagcagaga gcattataat caccagggcc aaaagcttcc    7980
ctccctgctg tcattgcttc ttctgaggcc tgaatccaaa agaaaacag ccataggccc     8040
tttcagtggc cgggctaccc gtgagcccct cggaggacca gggctgggc agcctctggg     8100
cccacatccg gggccagctc cggcgtgtgt tcagtgttag cagtgggtca tgatgctctt    8160
tcccacccag cctgggatag gggcagagga ggcgaggagg ccgttgccgc tgatgtttgg    8220
ccgtgaacag gtgggtgtct gcgtgcgtcc acgtgcgtgt tttctgactg acatgaaatc    8280
gacgcccgag ttagcctcac ccggtgacct ctagccctgc ccggatggag cggggcccac    8340
```

```
ccggttcagt gtttctgggg agctggacag tggagtgcaa aaggcttgca gaacttgaag    8400
cctgctcctt cccttgctac cacggcctcc tttccgtttg atttgtcact gcttcaatca    8460
ataacagccg ctccagagtc agtagtcaat gaatatatga ccaaatatca ccaggactgt    8520
tactcaatgt gtgccgagcc cttgcccatg ctgggctccc gtgtatctgg acactgtaac    8580
gtgtgctgtg tttgctcccc ttccccttcc ttctttgccc tttacttgtc tttctggggt    8640
ttttctgttt gggtttggtt tggttttat ttctcctttt gtgttccaaa catgaggttc     8700
tctctactgg tcctcttaac tgtggtgttg aggcttatat ttgtgtaatt tttggtgggt    8760
gaaaggaatt ttgctaagta aatctcttct gtgtttgaac tgaagtctgt attgtaacta    8820
tgtttaaagt aattgttcca gagacaaata tttctagaca cttttctttt acaaacaaaa    8880
gcattcggag ggagggggat ggtgactgag atgagagggg agagctgaac agatgacccc    8940
tgcccagatc agccagaagc cacccaaagc agtggagccc aggagtccca ctccaagcca    9000
gcaagccgaa tagctgatgt gttgccactt tccaagtcac tgcaaaacca ggttttgttc    9060
cgcccagtgg attcttgttt tgcttcccct ccccccgaga ttattaccac catcccgtgc    9120
ttttaaggaa aggcaagatt gatgtttcct tgaggggagc caggagggga tgtgtgtgtg    9180
cagagctgaa gagctgggga gaatgggggct gggcccaccc aagcaggagg ctgggacgct    9240
ctgctgtggg cacaggtcag gctaatgttg gcagatgcag ctcttcctgg acaggccagg    9300
tggtgggcat tctctctcca aggtgtgccc cgtgggcatt actgtttaag cacttccgt     9360
cacatcccac cccatcctcc agggctcaac actgtgacat ctctattccc caccctcccc    9420
ttcccagggc aataaaatga ccatggaggg ggcttgcact ctcttggctg tcacccgatc    9480
gccagcaaaa cttagatgtg agaaaacccc ttcccattcc atggcgaaaa catctcctta    9540
gaaaagccat taccctcatt aggcatggtt ttgggctccc aaaacacctg acagcccctc    9600
cctcctctga gaggcggaga gtgctgactg tagtgaccat tgcatgccgg gtgcagcatc    9660
tggaagagct aggcagggtg tctgccccct cctgagttga agtcatgctc ccctgtgcca    9720
gcccagaggc cgagagctat ggacagcatt gccagtaaca caggccaccc tgtgcagaag    9780
ggagctggct ccagcctgga aacctgtctg aggttgggag aggtgcactt ggggcacagg    9840
gagaggccgg gacacactta gctggagatg tctctaaaag ccctgtatcg tattcacctt    9900
cagttttttgt gttttgggac aattacttta gaaataagt aggtcgtttt aaaaacaaaa    9960
attattgatt gcttttttgt agtgttcaga aaaaggttc tttgtgtata gccaaatgac    10020
tgaaagcact gatatattta aaaacaaaag gcaatttatt aaggaaattt gtaccatttc    10080
agtaaacctg tctgaatgta cctgtatacg tttcaaaaac ccccccccc cactgaatcc     10140
ctgtaaccta tttattatat aaagagtttg ccttataaat tt                        10182
```

<210> SEQ ID NO 2
<211> LENGTH: 486
<212> TYPE: PRT
<213> ORGANISM: Homo sapiens

<400> SEQUENCE: 2

Met Val Ala Gly Met Leu Gly Leu Arg Glu Glu Lys Ser Glu Asp Gln
1               5                   10                  15

Asp Leu Gln Gly Leu Lys Asp Lys Pro Leu Lys Phe Lys Lys Val Lys
            20                  25                  30

Lys Asp Lys Lys Glu Glu Lys Glu Gly Lys His Glu Pro Val Gln Pro
        35                  40                  45

```
Ser Ala His His Ser Ala Glu Pro Ala Glu Gly Lys Ala Glu Thr
    50                  55                  60

Ser Glu Gly Ser Gly Ser Ala Pro Ala Val Pro Glu Ala Ser Ala Ser
65                  70                  75                  80

Pro Lys Gln Arg Arg Ser Ile Ile Arg Asp Arg Gly Pro Met Tyr Asp
                85                  90                  95

Asp Pro Thr Leu Pro Glu Gly Trp Thr Arg Lys Leu Lys Gln Arg Lys
            100                 105                 110

Ser Gly Arg Ser Ala Gly Lys Tyr Asp Val Tyr Leu Ile Asn Pro Gln
        115                 120                 125

Gly Lys Ala Phe Arg Ser Lys Val Glu Leu Ile Ala Tyr Phe Glu Lys
    130                 135                 140

Val Gly Asp Thr Ser Leu Asp Pro Asn Asp Phe Asp Phe Thr Val Thr
145                 150                 155                 160

Gly Arg Gly Ser Pro Ser Arg Arg Glu Gln Lys Pro Pro Lys Lys Pro
                165                 170                 175

Lys Ser Pro Lys Ala Pro Gly Thr Gly Arg Gly Arg Gly Arg Pro Lys
            180                 185                 190

Gly Ser Gly Thr Thr Arg Pro Lys Ala Ala Thr Ser Glu Gly Val Gln
        195                 200                 205

Val Lys Arg Val Leu Glu Lys Ser Pro Gly Lys Leu Leu Val Lys Met
    210                 215                 220

Pro Phe Gln Thr Ser Pro Gly Gly Lys Ala Glu Gly Gly Ala Thr
225                 230                 235                 240

Thr Ser Thr Gln Val Met Val Ile Lys Arg Pro Gly Arg Lys Arg Lys
                245                 250                 255

Ala Glu Ala Asp Pro Gln Ala Ile Pro Lys Lys Arg Gly Arg Lys Pro
            260                 265                 270

Gly Ser Val Val Ala Ala Ala Ala Glu Ala Lys Lys Lys Ala Val
        275                 280                 285

Lys Glu Ser Ser Ile Arg Ser Val Gln Glu Thr Val Leu Pro Ile Lys
    290                 295                 300

Lys Arg Lys Thr Arg Glu Thr Val Ser Ile Glu Val Lys Glu Val Val
305                 310                 315                 320

Lys Pro Leu Leu Val Ser Thr Leu Gly Glu Lys Ser Gly Lys Gly Leu
                325                 330                 335

Lys Thr Cys Lys Ser Pro Gly Arg Lys Ser Lys Glu Ser Ser Pro Lys
            340                 345                 350

Gly Arg Ser Ser Ser Ala Ser Ser Pro Lys Lys Glu His His
        355                 360                 365

His His His His Ser Glu Ser Pro Lys Ala Pro Val Pro Leu Leu Pro
    370                 375                 380

Pro Leu Pro Pro Pro Pro Glu Pro Glu Ser Ser Glu Asp Pro Thr
385                 390                 395                 400

Ser Pro Pro Glu Pro Gln Asp Leu Ser Ser Val Cys Lys Glu Glu
                405                 410                 415

Lys Met Pro Arg Gly Gly Ser Leu Glu Ser Asp Gly Cys Pro Lys Glu
            420                 425                 430

Pro Ala Lys Thr Gln Pro Ala Val Ala Thr Ala Thr Ala Ala Glu
        435                 440                 445

Lys Tyr Lys His Arg Gly Glu Gly Glu Arg Lys Asp Ile Val Ser Ser
    450                 455                 460
```

Ser Met Pro Arg Pro Asn Arg Glu Glu Pro Val Asp Ser Arg Thr Pro
465                 470                 475                 480

Val Thr Glu Arg Val Ser
                485

<210> SEQ ID NO 3
<211> LENGTH: 1504
<212> TYPE: DNA
<213> ORGANISM: Homo sapiens

<400> SEQUENCE: 3

```
ccggaaaatg gccgccgccg ccgccgccgc gccgagcgga ggaggaggag gaggcgagga      60
ggagagactg gaagaaaagt cagaagacca ggacctccag ggcctcaagg acaaaccct     120
caagtttaaa aaggtgaaga agataagaa agaagagaaa gagggcaagc atgagcccgt     180
gcagccatca gcccaccact ctgctgagcc cgcagaggca ggcaaagcag agacatcaga     240
agggtcaggc tccgcccgg ctgtgccgga agcttctgcc tccccaaac agcggcgctc     300
catcatccgt gaccggggac ccatgtatga tgaccccacc ctgcctgaag ctggacacg     360
gaagcttaag caaaggaaat ctggccgctc tgctgggaag tatgatgtgt atttgatcaa     420
tccccaggga aaagcctttc gctctaaagt ggagttgatt gcgtacttcg aaaaggtagg     480
cgacacatcc ctggaccct atgattttga cttcacggta actgggagag ggagcccctc     540
ccggcgagag cagaaaccac ctaagaagcc caaatctccc aaagctccag gaactggcag     600
aggccgggga cgccccaaag ggagcggcac cacgagaccc aaggcggcca cgtcagaggg     660
tgtgcaggta aaagggtcc tggagaaaag tcctgggaag ctccttgtca agatgccttt     720
tcaaacttcg ccaggggca aggctgaggg gggtggggcc accacatcca cccaggtcat     780
ggtgatcaaa cgccccggca ggaagcgaaa agctgaggcc gaccctcagg ccattcccaa     840
gaaacgggc cgaaagccgg ggagtgtggt ggcagccgct gccgccgagg ccaaaaagaa     900
agccgtgaag gagtcttcta tccgatctgt gcagagacc gtactcccca tcaagaagcg     960
caagacccgg gagacggtca gcatcgaggt caaggaagtg gtgaagcccc tgctggtgtc    1020
cacctcggt gagaagagcg ggaaaggact gaagacctgt aagagccctg gcggaaaag    1080
caaggagagc agccccaagg ggcgcagcag cagcgcctcc tcacccccca gaaggagca    1140
ccaccaccat caccaccact cagagtcccc aaaggcccc gtgccactgc tcccaccct    1200
gcccccacct ccacctgagc ccgagagctc cgaggacccc accagccccc ctgagcccca    1260
ggacttgagc agcagcgtct gcaaagagga gaagatgccc agaggaggct cactggagag    1320
cgacggctgc cccaaggagc cagctaagac tcagcccgcg gttgccaccg ccgccacggc    1380
cgcagaaaag tacaaacacc gaggggaggg agagcgcaaa gacattgttt catcctccat    1440
gccaaggcca aacagagagg agcctgtgga cagccggacg cccgtgaccg agagagttag    1500
ctga                                                                 1504
```

<210> SEQ ID NO 4
<211> LENGTH: 498
<212> TYPE: PRT
<213> ORGANISM: Homo sapiens

<400> SEQUENCE: 4

Met Ala Ala Ala Ala Ala Ala Pro Ser Gly Gly Gly Gly Gly Gly
1               5                   10                  15

Glu Glu Glu Arg Leu Glu Glu Lys Ser Glu Asp Gln Asp Leu Gln Gly
                20                  25                  30

```
Leu Lys Asp Lys Pro Leu Lys Phe Lys Val Lys Lys Asp Lys Lys
        35                  40                  45

Glu Glu Lys Glu Gly Lys His Glu Pro Val Gln Pro Ser Ala His His
 50                  55                  60

Ser Ala Glu Pro Ala Glu Ala Gly Lys Ala Glu Thr Ser Glu Gly Ser
 65                  70                  75                  80

Gly Ser Ala Pro Ala Val Pro Glu Ala Ser Ser Pro Lys Gln Arg
                 85                  90                  95

Arg Ser Ile Ile Arg Asp Arg Gly Pro Met Tyr Asp Asp Pro Thr Leu
                100                 105                 110

Pro Glu Gly Trp Thr Arg Lys Leu Lys Gln Arg Lys Ser Gly Arg Ser
             115                 120                 125

Ala Gly Lys Tyr Asp Val Tyr Leu Ile Asn Pro Gln Gly Lys Ala Phe
         130                 135                 140

Arg Ser Lys Val Glu Leu Ile Ala Tyr Phe Glu Lys Val Gly Asp Thr
145                 150                 155                 160

Ser Leu Asp Pro Asn Asp Phe Asp Phe Thr Val Thr Gly Arg Gly Ser
                165                 170                 175

Pro Ser Arg Arg Glu Gln Lys Pro Pro Lys Lys Pro Lys Ser Pro Lys
             180                 185                 190

Ala Pro Gly Thr Gly Arg Gly Arg Gly Arg Pro Lys Gly Ser Gly Thr
         195                 200                 205

Thr Arg Pro Lys Ala Ala Thr Ser Glu Gly Val Gln Val Lys Arg Val
210                 215                 220

Leu Glu Lys Ser Pro Gly Lys Leu Leu Val Lys Met Pro Phe Gln Thr
225                 230                 235                 240

Ser Pro Gly Gly Lys Ala Glu Gly Gly Gly Ala Thr Thr Ser Thr Gln
                245                 250                 255

Val Met Val Ile Lys Arg Pro Gly Arg Lys Arg Lys Ala Glu Ala Asp
             260                 265                 270

Pro Gln Ala Ile Pro Lys Lys Arg Gly Arg Lys Pro Gly Ser Val Val
         275                 280                 285

Ala Ala Ala Ala Ala Glu Ala Lys Lys Lys Ala Val Lys Glu Ser Ser
         290                 295                 300

Ile Arg Ser Val Gln Glu Thr Val Leu Pro Ile Lys Lys Arg Lys Thr
305                 310                 315                 320

Arg Glu Thr Val Ser Ile Glu Val Lys Glu Val Val Lys Pro Leu Leu
                325                 330                 335

Val Ser Thr Leu Gly Glu Lys Ser Gly Lys Gly Leu Lys Thr Cys Lys
             340                 345                 350

Ser Pro Gly Arg Lys Ser Lys Glu Ser Ser Pro Lys Gly Arg Ser Ser
         355                 360                 365

Ser Ala Ser Ser Pro Pro Lys Lys Glu His His His His His His
         370                 375                 380

Ser Glu Ser Pro Lys Ala Pro Val Pro Leu Leu Pro Pro Leu Pro Pro
385                 390                 395                 400

Pro Pro Pro Glu Pro Glu Ser Ser Glu Asp Pro Thr Ser Pro Pro Glu
                405                 410                 415

Pro Gln Asp Leu Ser Ser Ser Val Cys Lys Glu Glu Lys Met Pro Arg
             420                 425                 430

Gly Gly Ser Leu Glu Ser Asp Gly Cys Pro Lys Glu Pro Ala Lys Thr
         435                 440                 445
```

Gln Pro Ala Val Ala Thr Ala Ala Thr Ala Ala Glu Lys Tyr Lys His
        450                 455                 460

Arg Gly Glu Gly Glu Arg Lys Asp Ile Val Ser Ser Met Pro Arg
465                 470                 475                 480

Pro Asn Arg Glu Glu Pro Val Asp Ser Arg Thr Pro Val Thr Glu Arg
                485                 490                 495

Val Ser

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      HF primer

<400> SEQUENCE: 5
ctcggagaga gggctgtg                                                   18

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      HR1 primer

<400> SEQUENCE: 6
cttgaggggt ttgtccttga                                                 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      HR2 primer

<400> SEQUENCE: 7
cgtttgatca ccatgacctg                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      MF primer

<400> SEQUENCE: 8
aggaggcgag gaggagagac                                                 20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      MR primer

<400> SEQUENCE: 9
ctggctctgc agaatggtg                                                  19

<210> SEQ ID NO 10
<211> LENGTH: 22

```
<212> TYPE: DNA
<213> ORGANISM: Artificial Sequence
<220> FEATURE:
<223> OTHER INFORMATION: Description of Artificial Sequence: Synthetic
      MECP2B-specific primer

<400> SEQUENCE: 10
aggagagact ggaagaaaag tc                                          22

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 11
cttgaggggt ttgtccttga                                             20

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      MECP2A transcript-specific primer

<400> SEQUENCE: 12
ctcaccagtt cctgctttga tgt                                         23

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      MECP2B transcript-specific primer

<400> SEQUENCE: 13
aggagagact ggaggaaaag tc                                          22

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 14
cttaaacttc agtggcttgt ctctg                                       25

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      MECP2A forward primer

<400> SEQUENCE: 15
tatggatcca tggtagctgg gat                                         23

<210> SEQ ID NO 16
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      MECP2B forward primer

<400> SEQUENCE: 16
tatggatccg gaaaatggcc g                                              21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 17
gcgtctagag ctaactctct                                                20

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      MeCP2 N-terminus peptide

<400> SEQUENCE: 18

Met Ala Ala Ala Ala Ala Ala Ala Pro Ser Gly Gly Gly Gly Gly Gly
1               5                   10                  15

Glu Glu Glu Arg Leu
            20

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      X1F primer

<400> SEQUENCE: 19
ccatcacagc caatgacg                                                  18

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      X1R primer

<400> SEQUENCE: 20
aggggagggg tagagaggag                                                20

<210> SEQ ID NO 21
<211> LENGTH: 10171
<212> TYPE: DNA
<213> ORGANISM: Homo sapiens

<400> SEQUENCE: 21
ccggaaaatg gccgccgccg ccgccgccgc gccgagcagg aggcgaggag gagagactgc    60
tccataaaaa tacagactca ccagttcctg ctttgatgtg acatgtgact ccccagaata   120
caccttgctt ctgtagacca gctccaacag gattccatgg tagctgggat gttagggctc   180
```

```
agggaagaaa agtcagaaga ccaggacctc cagggcctca aggacaaacc cctcaagttt      240
aaaaaggtga agaaagataa gaaagaagag aaagagggca agcatgagcc cgtgcagcca      300
tcagcccacc actctgctga gcccgcagag gcaggcaaag cagagacatc agaagggtca      360
ggctccgccc cggctgtgcc ggaagcttct gcctccccca aacagcggcg ctccatcatc      420
cgtgaccggg gacccatgta tgatgacccc accctgcctg aaggctggac acggaagctt      480
aagcaaagga aatctggccg ctctgctggg aagtatgatg tgtatttgat caatccccag      540
ggaaaagcct ttcgctctaa agtggagttg attgcgtact tcgaaaaggt aggcgacaca      600
tccctggacc ctaatgattt tgacttcacg gtaactggga gagggagccc ctccggcga       660 gagcagaaac cacctaagaa gcccaaatct cccaaagctc aggaactggg cagaggccgg      720
ggacgcccca aagggagcgg caccacgaga cccaaggcgg ccacgtcaga gggtgtgcag      780
gtgaaagggg tcctggagaa aagtcctggg aagctccttg tcaagatgcc ttttcaaact      840
tcgccagggg gcaaggctga gggggtgggg gccaccacat ccacccaggt catggtgatc      900
aaacgccccg gcaggaagcg aaaagctgag gccgacccttc aggccattcc caagaaacgg      960
ggccgaaagc cggggagtgt ggtggcagcc gctgccgccg aggccaaaaa gaaagccgtg     1020
aaggagtctt ctatccgatc tgtgcaggag accgtactcc ccatcaagaa gcgcaagacc     1080
cgggagacgg tcagcatcga ggtcaaggaa gtggtgaagc ccctgctggt gtccaccctc     1140
ggtgagaaga gcgggaaagg actgaagacc tgtaagagcc ctgggcggaa aagcaaggag     1200
agcagcccca aggggcgcag cagcagcgcc tcctcacccc caagaaggag caccaccac      1260 catcaccacc actcagagtc cccaaaggcc cccgtgccac tgctcccacc cctgcccca       1320 cctccacctg agcccgagag ctccgaggac cccaccagcc cctgagcc ccaggacttg        1380 agcagcagcg tctgcaaaga ggagaagatg cccagaggag gctcactgga gagcgacggc     1440
tgccccaagg agccagctaa gactcagccc gcggttgcca ccgccgccac ggccgcagaa     1500
aagtacaaac accgaggga gggagagcgc aaagacattg tttcatcctc catgccaagg      1560
ccaaacagag aggagcctgt ggacagccgg acgcccgtga ccgagagagt tagctgactt     1620
tacacggagc ggattgcaaa gcaaaccaac aagaataaag gcagctgttg tctcttctcc     1680
ttatgggtag ggctctgaca aagcttcccg attaactgaa ataaaaaata ttttttttc      1740 tttcagtaaa cttagagttt cgtggcttca gggtgggagt agttggagca ttggggatgt     1800
ttttcttacc gacaagcaca gtcaggttga agacctaacc agggccagaa gtagctttgc     1860
acttttctaa actaggctcc ttcaacaagg cttgctgcag atactactga ccagacaagc     1920
tgttgaccag gcacctcccc tcccgcccaa acctttcccc catgtggtcg ttagagacag     1980
agcgacagag cagttgagag gacactcccg ttttcggtgc catcagtgcc ccgtctacag     2040
ctcccccagc tcccccacc tccccacactc ccaaccacgt tgggacaggg aggtgtgagg     2100
caggagagac agttggattc tttagagaag atggatatga ccagtggcta tggcctgtgc     2160
gatcccaccc gtggtggctc aagtctggcc ccacaccagc cccaatccaa aactggcaag     2220
gacgcttcac aggacaggaa agtggcacct gtctgctcca gctctggcat ggctaggagg     2280
ggggagtccc ttgaactact gggtgtagac tggcctgaac cacaggagag gatgcccag      2340 ggtgaggtgg catggtccat tctcaaggga cgtcctccaa cgggtggcgc tagaggccat     2400
ggaggcagta ggacaaggtg caggcaggct ggcctgggt caggccgggc agagcacagc      2460
ggggtgagag ggattcctaa tcactcagag cagtctgtga cttagtggac aggggagggg     2520
gcaaaggggg aggagaagaa aatgttcttc cagttacttt ccaattctcc tttagggaca     2580
```

```
gcttagaatt atttgcacta ttgagtcttc atgttcccac ttcaaaacaa acagatgctc    2640
tgagagcaaa ctggcttgaa ttggtgacat ttagtccctc aagccaccag atgtgacagt    2700
gttgagaact acctggattt gtatatatac ctgcgcttgt tttaaagtgg gctcagcaca    2760
tagggttccc acgaagctcc gaaactctaa gtgtttgctg caattttata aggacttcct    2820
gattggtttc tcttctcccc ttccatttct gccttttgtt catttcatcc tttcacttct    2880
ttcccttcct ccgtcctcct ccttcctagt tcatcccttc tcttccaggc agccgcggtg    2940
cccaaccaca cttgtcggct ccagtcccca gaactctgcc tgccctttgt cctcctgctg    3000
ccagtaccag ccccaccctg ttttgagccc tgaggaggcc ttgggctctg ctgagtccga    3060
cctggcctgt ctgtgaagag caagagagca gcaaggtctt gctctcctag gtagccccct    3120
cttccctggt aagaaaaagc aaaaggcatt tcccaccctg aacaacgagc cttttcaccc    3180
ttctactcta gagaagtgga ctggaggagc tgggcccgat ttggtagttg aggaaagcac    3240
agaggcctcc tgtggcctgc cagtcatcga gtggcccaac aggggctcca tgccagccga    3300
ccttgacctc actcagaagt ccagagtcta gcgtagtgca gcagggcagt agcggtacca    3360
atgcagaact cccaagaccc gagctgggac cagtacctgg gtccccagcc cttcctctgc    3420
tccccctttt ccctcggagt tcttcttgaa tggcaatgtt ttgcttttgc tcgatgcaga    3480
caggggccca gaacaccaca catttcactg tctgtctggt ccatagctgt ggtgtagggg    3540
cttagaggca tgggcttgct gtgggttttt aattgatcag ttttcatgtg ggatcccatc    3600
tttttaacct ctgttcagga agtccttatc tagctgcata tcttcatcat attggtatat    3660
ccttttctgt gtttacagag atgtctctta tatctaaatc tgtccaactg agaagtacct    3720
tatcaaagta gcaaatgaga cagcagtctt atgcttccag aaacacccac aggcatgtcc    3780
catgtgagct gctgccatga actgtcaagt gtgtgttgtc ttgtgtattt cagttattgt    3840
ccctggcttc cttactatgg tgtaatcatg aaggagtgaa acatcataga aactgtctag    3900
cacttccttg ccagtcttta gtgatcagga accatagttg acagttccaa tcagtagctt    3960
aagaaaaaac cgtgtttgtc tcttctggaa tggttagaag tgagggagtt tgccccgttc    4020
tgtttgtaga gtctcatagt tggactttct agcatatatg tgtccatttc cttatgctgt    4080
aaaagcaagt cctgcaacca aactcccatc agcccaatcc ctgatccctg atcccttcca    4140
cctgctctgc tgatgacccc cccagcttca cttctgactc ttccccagga agggaagggg    4200
ggtcagaaga gagggtgagt cctccagaac tcttcctcca aggacagaag gctcctgccc    4260
ccatagtggc ctcgaactcc tggcactacc aaaggacact tatccacgag agcgcagcat    4320
ccgaccaggt tgtcactgag aagatgttta ttttggtcag ttgggttttt atgtattata    4380
cttagtcaaa tgtaatgtgg cttctggaat cattgtccag agctgcttcc ccgtcacctg    4440
ggcgtcatct ggtcctggta agaggagtgc gtggcccacc aggccccct gtcacccatg    4500 acagttcatt cagggccgat ggggcagtcg tggttgggaa cacagcattt caagcgtcac    4560
tttatttcat tcgggcccca cctgcagctc cctcaaagag gcagttgccc agcctctttc    4620
ccttccagtt tattccagag ctgccagtgg ggcctgaggc tccttagggt tttctctcta    4680 tttcccccctt tcttcctcat tccctcgtct ttcccaaagg catcacgagt cagtcgcctt    4740
tcagcaggca gccttggcgg tttatcgccc tggcaggcag gggccctgca gctctcatgc    4800
tgcccctgcc ttggggtcag gttgacagga ggttggaggg aaagccttaa gctgcaggat    4860
tctcaccagc tgtgtccggc ccagttttgg ggtgtgacct caatttcaat tttgtctgta    4920
```

| | |
|---|---|
| cttgaacatt atgaagatgg gggcctcttt cagtgaattt gtgaacagca gaattgaccg | 4980 |
| acagctttcc agtacccatg gggctaggtc attaaggcca catccacagt ctcccccacc | 5040 |
| cttgttccag ttgttagtta ctacctcctc tcctgacaat actgtatgtc gtcgagctcc | 5100 |
| ccccaggtct acccctcccg gccctgcctg ctggtgggct tgtcatagcc agtgggattg | 5160 |
| ccggtcttga cagctcagtg agctggagat acttggtcac agccaggcgc tagcacagct | 5220 |
| cccttctgtt gatgctgtat tcccatatca aagacacag gggacaccca gaaacgccac | 5280 |
| atcccccaat ccatcagtgc caaactagcc aacggcccca gcttctcagc tcgctggatg | 5340 |
| gcggaagctg ctactcgtga cgccagtgc gggtgcagac aatcttctgt tgggtggcat | 5400 |
| cattccaggc ccgaagcatg aacagtgcac ctgggacagg gagcagcccc aaattgtcac | 5460 |
| ctgcttctct gcccagcttt tcattgctgt gacagtgatg gcgaaagagg gtaataacca | 5520 |
| gacacaaact gccaagttgg gtggagaaag gagtttcttt agctgacaga atctctgaat | 5580 |
| tttaaatcac ttagtaagcg gctcaagccc aggaggagc agagggatac gagcggagtc | 5640 |
| ccctgcgcgg gaccatctgg aattggttta gcccaagtgg agcctgacag ccagaactct | 5700 |
| gtgtcccccg tctaaccaca gctccttttc cagagcattc cagtcaggct ctctgggctg | 5760 |
| actgggccag gggaggttac aggtaccagt tcttaagaa gatctttggg catatacatt | 5820 |
| tttagcctgt gtcattgccc caaatggatt cctgtttcaa gttcacacct gcagattcta | 5880 |
| ggacctgtgt cctagacttc agggagtcag ctgtttctag agttcctacc atggagtggg | 5940 |
| tctggaggac ctgcccggtg gggggcaga gccctgctcc ctccgggtct tcctactctt | 6000 |
| ctctctgctc tgacgggatt tgttgattct ctccattttg gtgtctttct cttttagata | 6060 |
| ttgtatcaat ctttagaaaa ggcatagtct acttgttata aatcgttagg atactgcctc | 6120 |
| ccccaggtc taaaattaca tattagaggg gaaaagctga acactgaagt cagttctcaa | 6180 |
| caatttagaa ggaaaaccta gaaaacattt ggcagaaaat tacatttcga tgttttttgaa | 6240 |
| tgaatacgag caagctttta caacagtgct gatctaaaaa tacttagcac ttggcctgag | 6300 |
| atgcctggtg agcattacag gcaagggggaa tctggaggta gccgacctga ggacatggct | 6360 |
| tctgaacctg tcttttggga gtggtatgga aggtggagcg ttcaccagtg acctggaagg | 6420 |
| cccagcacca ccctccttcc cactcttctc atcttgacag agcctgcccc agcgctgacg | 6480 |
| tgtcaggaaa acacccaggg aactaggaag gcacttctgc ctgaggggca gcctgccttg | 6540 |
| cccactcctg ctctgctcgc tcggatcag ctgagccttc tgagctggcc tctcactgcc | 6600 |
| tccccaaggc cccctgcctg ccctgtcagg aggcagaagg aagcaggtgt gagggcagtg | 6660 |
| caaggaggga gcacaacccc cagctcccgc tccgggctcc gacttgtgca caggcagagc | 6720 |
| ccagaccctg gaggaaatcc tacctttgaa ttcaagaaca tttgggggaat ttggaaatct | 6780 |
| ctttgcccccc aaacccccat tctgtcctac ctttaatcag gtcctgctca gcagtgagag | 6840 |
| cagatgaggt gaaaaggcca agaggtttgg ctcctgccca ctgatagccc ctctccccgc | 6900 |
| agtgtttgtg tgtcaagtgg caaagctgtt cttcctggtg accctgatta tatccagtaa | 6960 |
| cacatagact gtgcgcatag gcctgctttg tctcctctat cctgggcttt tgttttgctt | 7020 |
| tttagttttg ctttttagttt ttctgtccct tttatttaac gcaccgacta gacacacaaa | 7080 |
| gcagttgaat ttttatatat atatctgtat attgcacaat tataaactca ttttgcttgt | 7140 |
| ggctccacac acacaaaaaa agacctgtta aaattatacc tgttgcttaa ttacaatatt | 7200 |
| tctgataacc atagcatagg acaagggaaa ataaaaaaag aaaaaaaga aaaaaaacg | 7260 |
| acaaatctgt ctgctggtca cttcttctgt ccaagcagat tcgtggtctt ttcctcgctt | 7320 |

```
ctttcaaggg ctttcctgtg ccaggtgaag gaggctccag gcagcaccca ggttttgcac    7380
tcttgtttct cccgtgcttg tgaaagaggt cccaaggttc tgggtgcagg agcgctccct    7440
tgacctgctg aagtccggaa cgtagtcggc acagcctggt cgccttccac ctctgggagc    7500
tggagtccac tggggtggcc tgactccccc agtccccttc ccgtgacctg gtcagggtga    7560
gcccatgtgg agtcagcctc gcaggcctcc ctgccagtag ggtccgagtg tgtttcatcc    7620
ttcccactct gtcgagcctg ggggctggag cggagacggg aggcctggcc tgtctcggaa    7680
cctgtgagct gcaccaggta gaacgccagg gaccccagaa tcatgtgcgt cagtccaagg    7740
ggtcccctcc aggagtagtg aagactccag aaatgtccct ttcttctccc ccatcctacg    7800
agtaattgca tttgcttttg taattcttaa tgagcaatat ctgctagaga gtttagctgt    7860
aacagttctt tttgatcatc ttttttttaat aattagaaac accaaaaaaa tccagaaact    7920
tgttcttcca aagcagagag cattataatc accagggcca aaagcttccc tccctgctgt    7980
cattgcttct tctgaggcct gaatccaaaa gaaaaacagc cataggccct ttcagtggcc    8040
gggctacccg tgagcccttc ggaggaccag ggctggggca gcctctgggc ccacatccgg    8100
ggccagctcc ggcgtgtgtt cagtgttagc agtgggtcat gatgctcttt cccacccagc    8160
ctgggatagg ggcagaggag gcgaggaggc cgttgccgct gatgtttggc cgtgaacagg    8220
tgggtgtctg cgtgcgtcca cgtgcgtgtt ttctgactga catgaaatcg acgcccgagt    8280
tagcctcacc cggtgacctc tagccctgcc cggatggagc ggggcccacc cggttcagtg    8340
tttctgggga gctggacagt ggagtgcaaa aggcttgcag aacttgaagc ctgctccttc    8400
ccttgctacc acggcctcct ttccgtttga tttgtcactg cttcaatcaa taacagccgc    8460
tccagagtca gtagtcaatg aatatatgac caaatatcac caggactgtt actcaatgtg    8520
tgccgagccc ttgcccatgc tgggctcccg tgtatctgga cactgtaacg tgtgctgtgt    8580
ttgctcccct tccccttcct tctttgccct ttacttgtct ttctggggtt tttctgtttg    8640
ggtttggttt ggttttattt tctccttttg tgttccaaac atgaggttct ctctactggt    8700
cctcttaact gtggtgttga ggcttatatt tgtgtaattt ttggtgggtg aaaggaattt    8760
tgctaagtaa atctcttctg tgtttgaact gaagtctgta ttgtaactat gtttaaagta    8820
attgttccag agacaaatat ttctagacac tttttcttta caaacaaaag cattcggagg    8880
gagggggatg gtgactgaga tgagagggga gagctgaaca gatgaccct gcccagatca    8940 gccagaagcc acccaaagca gtggagccca ggagtcccac tccaagccag caagccgaat    9000
agctgatgtg ttgccacttt ccaagtcact gcaaaaccag gttttgttcc gcccagtgga    9060
ttcttgtttt gcttcccctc cccccgagat tattaccacc atcccgtgct tttaaggaaa    9120
ggcaagattg atgtttcctt gaggggagcc aggaggggat gtgtgtgtgc agagctgaag    9180
agctggggag aatgggctg gcccacccca agcaggaggc tgggacgctc tgctgtgggc    9240
acaggtcagg ctaatgttgg cagatgcagc tcttcctgga caggccaggt ggtgggcatt    9300
ctctctccaa ggtgtgcccc gtgggcatta ctgtttaaga cacttccgtc acatcccacc    9360
ccatcctcca gggctcaaca ctgtgacatc tctattcccc accctcccct tcccagggca    9420
ataaaatgac catggagggg gcttgcactc tcttggctgt cacccgatcg ccagcaaaac    9480
ttagatgtga gaaacccct tccattcca tggcgaaaac atctccttag aaaagccatt    9540
accctcatta ggcatggttt tgggctccca aacacctga cagcccctcc ctcctctgag    9600
aggcggagag tgctgactgt agtgaccatt gcatgccggg tgcagcatct ggaagagcta    9660
```

| | |
|---|---|
| ggcagggtgt ctgcccctc ctgagttgaa gtcatgctcc cctgtgccag cccagaggcc | 9720 |
| gagagctatg gacagcattg ccagtaacac aggccaccct gtgcagaagg gagctggctc | 9780 |
| cagcctggaa acctgtctga ggttgggaga ggtgcacttg gggcacaggg agaggccggg | 9840 |
| acacacttag ctggagatgt ctctaaaagc cctgtatcgt attcaccttc agttttgtg | 9900 |
| ttttgggaca attactttag aaataagta ggtcgtttta aaacaaaaa ttattgattg | 9960 |
| cttttttgta gtgttcagaa aaaggttct ttgtgtatag ccaaatgact gaaagcactg | 10020 |
| atatatttaa aaacaaaagg caatttatta aggaaatttg taccatttca gtaaacctgt | 10080 |
| ctgaatgtac ctgtatacgt ttcaaaaaca cccccccccc actgaatccc tgtaacctat | 10140 |
| ttattatata aagagtttgc cttataaatt t | 10171 |

<210> SEQ ID NO 22
<211> LENGTH: 10113
<212> TYPE: DNA
<213> ORGANISM: Homo sapiens

<400> SEQUENCE: 22

| | |
|---|---|
| gctccataaa aatacagact caccagttcc tgctttgatg tgacatgtga ctccccagaa | 60 |
| tacaccttgc ttctgtagac cagctccaac aggattccat ggtagctggg atgttagggc | 120 |
| tcagggaaga aaagtcagaa gaccaggacc tccagggcct caaggacaaa cccctcaagt | 180 |
| ttaaaaaggt gaagaaagat aagaagaag agaagagg caagcatgag cccgtgcagc | 240 |
| catcagccca ccactctgct gagcccgcag aggcaggcaa agcagagaca tcagaagggt | 300 |
| caggctccgc cccggctgtg ccggaagctt ctgcctcccc caaacagcgg cgctccatca | 360 |
| tccgtgaccg gggacccatg tatgatgacc ccaccctgcc tgaaggctgg acacggaagc | 420 |
| ttaagcaaag gaaatctggc cgctctgctg ggaagtatga tgtgtatttg atcaatcccc | 480 |
| agggaaaagc ctttcgctct aaagtggagt tgattgcgta cttcgaaaag gtaggcgaca | 540 |
| catccctgga ccctaatgat tttgacttca cggtaactgg gagagggagc ccctcccggc | 600 |
| gagagcagaa accacctaag aagcccaaat ctcccaaagc tccaggaact ggcagaggcc | 660 |
| ggggacgccc caaggggagc ggcaccacga gaccccaaggc ggccacgtca gagggtgtgc | 720 |
| aggtgaaaag ggtcctggag aaaagtcctg ggaagctcct tgtcaagatg ccttttcaaa | 780 |
| cttcgccagg gggcaaggct gaggggggtg gggccaccac atccacccag gtcatggtga | 840 |
| tcaaacgccc cggcaggaag cgaaaagctg aggccgaccc tcaggccatt cccaagaaac | 900 |
| ggggccgaaa gccggggagt gtggtggcag ccgctgccgc cgaggccaaa agaaaagccg | 960 |
| tgaaggagtc ttctatccga tctgtgcagg agaccgtact cccatcaag aagcgcaaga | 1020 |
| cccgggagac ggtcagcatc gaggtcaagg aagtggtgaa gccctgctg gtgtccaccc | 1080 |
| tcggtgagaa gagcgggaaa ggactgaaga cctgtaagag ccctgggcgg aaaagcaagg | 1140 |
| agagcagccc caaggggcgc agcagcagcg cctcctcacc cccaagaag gagcaccacc | 1200 |
| accatcacca ccactcagag tccccaaagg ccccgtgcc actgctccca ccctgcccc | 1260 |
| cacctccacc tgagcccgag agctccgagg accccaccag ccccctgag cccaggact | 1320 |
| tgagcagcag cgtctgcaaa gaggagaaga tgccagagg aggctcactg gagagcgacg | 1380 |
| gctgccccaa ggagccagct aagactcagc ccgcggttgc caccgccgcc acggccgcag | 1440 |
| aaaagtacaa acaccgaggg gagggagagc gcaaagacat tgtttcatcc tccatgccaa | 1500 |
| ggccaaacag agaggagcct gtggacagcc ggacgcccgt gaccgagaga gttagctgac | 1560 |
| tttacacgga gcggattgca aagcaaacca acaagaataa aggcagctgt tgtctcttct | 1620 |

```
ccttatgggt agggctctga caaagcttcc cgattaactg aaataaaaaa tatttttttt    1680
tctttcagta aacttagagt ttcgtggctt cagggtggga gtagttggag cattggggat    1740
gttttcttta ccgacaagca cagtcaggtt gaagacctaa ccagggccag aagtagcttt    1800
gcacttttct aaactaggct ccttcaacaa ggcttgctgc agatactact gaccagacaa    1860
gctgttgacc aggcacctcc cctcccgccc aaacctttcc cccatgtggt cgttagagac    1920
agagcgacag agcagttgag aggacactcc cgttttcggt gccatcagtg ccccgtctac    1980
agctccccca gctccccca cctcccccac tcccaaccac gttgggacag ggaggtgtga    2040
ggcaggagag acagttggat tctttagaga agatggatat gaccagtggc tatggcctgt    2100
gcgatcccac ccgtggtggc tcaagtctgg ccccacacca gccccaatcc aaaactggca    2160
aggacgcttc acaggacagg aaagtggcac ctgtctgctc cagctctggc atggctagga    2220
ggggggagtc ccttgaacta ctgggtgtag actggcctga accacaggag aggatggccc    2280
agggtgaggt ggcatggtcc attctcaagg gacgtcctcc aacgggtggc gctagaggcc    2340
atggaggcag taggacaagg tgcaggcagg ctggcctggg gtcaggccgg gcagagcaca    2400
gcggggtgag agggattcct aatcactcag agcagtctgt gacttagtgg acaggggagg    2460
gggcaaaggg ggaggagaag aaaatgttct tccagttact ttccaattct cctttaggga    2520
cagcttagaa ttatttgcac tattgagtct tcatgttccc acttcaaaac aaacagatgc    2580
tctgagagca aactggcttg aattggtgac atttagtccc tcaagccacc agatgtgaca    2640
gtgttgagaa ctacctggat ttgtatatat acctgcgctt gttttaaagt gggctcagca    2700
catagggttc ccacgaagct ccgaaactct aagtgtttgc tgcaattttta taaggacttc    2760 ctgattggtt tctcttctcc ccttccattt ctgcctttg ttcatttcat cctttcactt    2820
cttccccttc ctccgtcctc ctccttccta gttcatccct tctcttccag gcagccgcgg    2880
tgcccaacca cacttgtcgg ctccagtccc cagaactctg cctgcccttt gtcctcctgc    2940
tgccagtacc agccccaccc tgttttgagc cctgaggagg ccttgggctc tgctgagtcc    3000
gacctggcct gtctgtgaag agcaagagag cagcaaggtc ttgctctcct aggtagcccc    3060
ctcttccctg gtaagaaaaa gcaaaaggca tttcccaccc tgaacaacga gcctttttcac   3120 ccttctactc tagagaagtg gactggagga gctgggcccg atttggtagt tgaggaaagc    3180
acagaggcct cctgtggcct gccagtcatc gagtggccca cagggggctc catgccagcc    3240
gaccttgacc tcactcagaa gtccagagtc tagcgtagtg cagcagggca gtagcggtac    3300
caatgcagaa ctcccaagac ccgagctggg accagtacct gggtccccag cccttcctct    3360 gctcccccttt tccctcgga gttcttcttg aatggcaatg ttttgctttt gctcgatgca    3420 gacaggggc cagaacacca cacatttcac tgtctgtctg gtccatagct gtggtgtagg    3480
ggcttagagg catgggcttg ctgtgggttt ttaattgatc agttttcatg tgggatccca    3540
tctttttaac ctctgttcag gaagtcctta tctagctgca tatcttcatc atattggtat    3600
atccttttct gtgtttacag agatgtctct tatatctaaa tctgtccaac tgagaagtac    3660
cttatcaaag tagcaaatga gacagcagtc ttatgcttcc agaaacaccc acaggcatgt    3720
cccatgtgag ctgctgccat gaactgtcaa gtgtgtgttg tcttgtgtat ttcagttatt    3780
gtccctggct tccttactat ggtgtaatca tgaaggagtg aaacatcata gaaactgtct    3840
agcacttcct tgccagtctt tagtgatcag gaaccatagt tgacagttcc aatcagtagc    3900
ttaagaaaaa accgtgtttg tctcttctgg aatggttaga agtgagggag tttgccccgt    3960
```

```
tctgtttgta gagtctcata gttggacttt ctagcatata tgtgtccatt tccttatgct    4020
gtaaaagcaa gtcctgcaac caaactccca tcagcccaat ccctgatccc tgatcccttc    4080
cacctgctct gctgatgacc cccccagctt cacttctgac tcttccccag gaagggaagg    4140
ggggtcagaa gagagggtga gtcctccaga actcttcctc caaggacaga aggctcctgc    4200
ccccatagtg gcctcgaact cctggcacta ccaaaggaca cttatccacg agagcgcagc    4260
atccgaccag gttgtcactg agaagatgtt tattttggtc agttgggttt ttatgtatta    4320
tacttagtca aatgtaatgt ggcttctgga atcattgtcc agagctgctt ccccgtcacc    4380
tgggcgtcat ctggtcctgg taagaggagt gcgtggccca ccaggccccc ctgtcaccca    4440
tgacagttca ttcagggccg atgggcagt cgtggttggg aacacagcat ttcaagcgtc    4500
actttatttc attcgggccc cacctgcagc tccctcaaag aggcagttgc ccagcctctt    4560
tcccttccag tttattccag agctgccagt ggggcctgag gctccttagg gttttctctc    4620
tatttccccc tttcttcctc attccctcgt cttttcccaaa ggcatcacga gtcagtcgcc    4680
tttcagcagg cagccttggc ggtttatcgc cctggcaggc aggggccctg cagctctcat    4740
gctgcccctg ccttggggtc aggttgacag gaggttggag ggaaagcctt aagctgcagg    4800
attctcacca gctgtgtccg gcccagtttt ggggtgtgac ctcaatttca attttgtctg    4860
tacttgaaca ttatgaagat gggggcctct ttcagtgaat ttgtgaacag cagaattgac    4920
cgacagcttt ccagtaccca tggggctagg tcattaaggc cacatccaca gtctccccca    4980
cccttgttcc agttgttagt tactacctcc tctcctgaca atactgtatg tcgtcgagct    5040
cccccaggt ctaccctcc cggccctgcc tgctggtggg cttgtcatag ccagtgggat    5100
tgccggtctt gacagctcag tgagctggag atacttggtc acagccaggc gctagcacag    5160
ctcccttctg ttgatgctgt attcccatat caaaagacac aggggacacc cagaaacgcc    5220
acatccccca atccatcagt gccaaactag ccaacggccc cagcttctca gctcgctgga    5280
tggcggaagc tgctactcgt gagcgccagt gcgggtgcag acaatcttct gttgggtggc    5340
atcattccag gcccgaagca tgaacagtgc acctgggaca gggagcagcc ccaaattgtc    5400
acctgcttct ctgcccagct tttcattgct gtgacagtga tggcgaaaga gggtaataac    5460
cagacacaaa ctgccaagtt gggtggagaa aggagtttct ttagctgaca gaatctctga    5520
attttaaatc acttagtaag cggctcaagc ccaggaggga gcagagggat acgagcggag    5580
tcccctgcgc gggaccatct ggaattggtt tagcccaagt ggagcctgac agccagaact    5640
ctgtgtcccc cgtctaacca cagctccttt tccagagcat tccagtcagg ctctctgggc    5700
tgactgggcc aggggaggtt acaggtacca gttctttaag aagatctttg gcatataca    5760
ttttagcct gtgtcattgc cccaaatgga ttcctgtttc aagttcacac ctgcagattc    5820
taggacctgt gtcctagact tcagggagtc agctgtttct agagttccta ccatggagtg    5880
ggtctggagg acctgcccgg tgggggggca gagccctgct ccctccgggt cttcctactc    5940
ttctctctgc tctgacggga tttgttgatt ctctccatttt tggtgtcttt ctcttttaga    6000
tattgtatca atctttagaa aaggcatagt ctacttgtta taaatcgtta ggatactgcc    6060
tcccccaggg tctaaaatta catattagag gggaaaagct gaacactgaa gtcagttctc    6120
aacaatttag aaggaaaacc tagaaaacat ttggcagaaa attacatttc gatgttttg    6180
aatgaatacg agcaagcttt tacaacagtg ctgatctaaa aatacttagc acttggcctg    6240
agatgcctgg tgagcattac aggcaagggg aatctggagg tagccgacct gaggacatgg    6300
cttctgaacc tgtcttttgg gagtggtatg gaaggtggag cgttcaccag tgacctggaa    6360
```

```
ggcccagcac caccctcctt cccactcttc tcatcttgac agagcctgcc ccagcgctga   6420
cgtgtcagga aaacacccag ggaactagga aggcacttct gcctgagggg cagcctgcct   6480
tgcccactcc tgctctgctc gcctcggatc agctgagcct tctgagctgg cctctcactg   6540
cctccccaag gcccctgcc tgccctgtca ggaggcagaa ggaagcaggt gtgagggcag    6600
tgcaaggagg gagcacaacc cccagctccc gctccgggct ccgacttgtg cacaggcaga   6660
gcccagaccc tggaggaaat cctacctttg aattcaagaa catttgggga atttggaaat   6720
ctctttgccc ccaaaccccc attctgtcct acctttaatc aggtcctgct cagcagtgag   6780
agcagatgag gtgaaaaggc caagaggttt ggctcctgcc cactgatagc ccctctcccc   6840
gcagtgtttg tgtgtcaagt ggcaaagctg ttcttcctgg tgaccctgat tatatccagt   6900
aacacataga ctgtgcgcat aggcctgctt tgtctcctct atcctgggct tttgttttgc   6960
tttttagttt tgcttttagt ttttctgtcc cttttattta acgcaccgac tagacacaca   7020
aagcagttga atttttatat atatatctgt atattgcaca attataaact cattttgctt   7080
gtggctccac acacacaaaa aaagacctgt taaaattata cctgttgctt aattacaata   7140
tttctgataa ccatagcata ggacaaggga aaataaaaaa agaaaaaaaa gaaaaaaaa    7200 cgacaaatct gtctgctggt cacttcttct gtccaagcag attcgtggtc ttttcctcgc   7260
ttctttcaag ggctttcctg tgccaggtga aggaggctcc aggcagcacc caggttttgc   7320
actcttgttt ctcccgtgct tgtgaaagag gtcccaaggt tctgggtgca ggagcgctcc   7380
cttgacctgc tgaagtccgg aacgtagtcg gcacagcctg gtcgccttcc acctctggga   7440
gctggagtcc actggggtgg cctgactccc ccagtcccct tcccgtgacc tggtcagggt   7500
gagcccatgt ggagtcagcc tcgcaggcct ccctgccagt agggtccgag tgtgtttcat   7560
ccttcccact ctgtcgagcc tgggggctgg agcggagacg ggaggcctgg cctgtctcgg   7620
aacctgtgag ctgcaccagg tagaacgcca gggaccccag aatcatgtgc gtcagtccaa   7680
ggggtcccct ccaggagtag tgaagactcc agaaatgtcc ctttcttctc ccccatccta   7740
cgagtaattg catttgcttt tgtaattctt aatgagcaat atctgctaga gagtttagct   7800
gtaacagttc ttttttgatca tcttttttta ataattagaa acaccaaaaa aatccagaaa   7860
cttgttcttc caaagcagag agcattataa tcaccagggc caaaagcttc cctccctgct   7920
gtcattgctt cttctgaggc ctgaatccaa agaaaaaca gccataggcc ctttcagtgg    7980
ccgggctacc cgtgagccct tcggaggacc agggctgggg cagcctctgg gcccacatcc   8040
ggggccagct ccggcgtgtg ttcagtgtta gcagtgggtc atgatgctct ttcccaccca   8100
gcctgggata ggggcagagg aggcgaggag gccgttgccg ctgatgtttg gccgtgaaca   8160
ggtgggtgtc tgcgtgcgtc cacgtgcgtg ttttctgact gacatgaaat cgacgcccga   8220
gttagcctca cccggtgacc tctagccctg cccggatgga gcggggccca cccggttcag   8280
tgtttctggg gagctggaca gtggagtgca aaaggcttgc agaacttgaa gcctgctcct   8340
tcccttgcta ccacggcctc ctttccgttt gatttgtcac tgcttcaatc aataacagcc   8400
gctccagagt cagtagtcaa tgaatatatg accaaatatc accaggactg ttactcaatg   8460
tgtgccgagc ccttgcccat gctgggctcc cgtgtatctg gacactgtaa cgtgtgctgt   8520
gtttgctccc cttcccccttc ctttctttgcc ctttacttgt ctttctgggg ttttctgtt   8580 tgggtttggt ttggttttta tttctccttt tgtgttccaa acatgaggtt ctctctactg   8640
gtcctcttaa ctgtggtgtt gaggcttata tttgtgtaat ttttggtggg tgaaaggaat   8700
```

```
tttgctaagt aaatctcttc tgtgtttgaa ctgaagtctg tattgtaact atgtttaaag    8760
taattgttcc agagacaaat atttctagac acttttttctt tacaaacaaa agcattcgga    8820
gggaggggga tggtgactga gatgagaggg gagagctgaa cagatgaccc ctgcccagat    8880
cagccagaag ccacccaaag cagtggagcc caggagtccc actccaagcc agcaagccga    8940
atagctgatg tgttgccact ttccaagtca ctgcaaaacc aggttttgtt ccgcccagtg    9000
gattcttgtt ttgcttcccc tccccccgag attattacca ccatcccgtg cttttaagga    9060
aaggcaagat tgatgtttcc ttgaggggag ccaggagggg atgtgtgtgt gcagagctga    9120
agagctgggg agaatggggc tgggcccacc caagcaggag gctggacgc tctgctgtgg    9180 gcacaggtca ggctaatgtt ggcagatgca gctcttcctg gacaggccag gtggtgggca    9240
ttctctctcc aaggtgtgcc ccgtgggcat tactgtttaa gacacttccg tcacatccca    9300
ccccatcctc cagggctcaa cactgtgaca tctctattcc ccaccctccc cttcccaggg    9360
caataaaatg accatggagg gggcttgcac tctcttggct gtcacccgat cgccagcaaa    9420
acttagatgt gagaaaaccc cttcccattc catggcgaaa acatctcctt agaaaagcca    9480
ttaccctcat taggcatggt tttgggctcc caaaacacct gacagcccct ccctcctctg    9540
agaggcggag agtgctgact gtagtgacca ttgcatgccg ggtgcagcat ctggaagagc    9600
taggcagggt gtctgccccc tcctgagttg aagtcatgct cccctgtgcc agcccagagg    9660
ccgagagcta tggacagcat tgccagtaac acaggccacc ctgtgcagaa gggagctggc    9720
tccagcctgg aaacctgtct gaggttggga gaggtgcact tggggcacag ggagaggccg    9780
ggacacactt agctggagat gtctctaaaa gccctgtatc gtattcacct tcagttttttg    9840 tgttttggga caattacttt agaaaataag taggtcgttt taaaaacaaa aattattgat    9900 tgctttttttg tagtgttcag aaaaaaggtt ctttgtgtat agccaaatga ctgaaagcac    9960
tgatatattt aaaaacaaaa ggcaatttat taaggaaatt tgtaccattt cagtaaacct   10020
gtctgaatgt acctgtatac gtttcaaaaa cacccccccc ccactgaatc cctgtaacct   10080
atttattata taaagagttt gccttataaa ttt                                10113
```

<210> SEQ ID NO 23
<211> LENGTH: 10182
<212> TYPE: DNA
<213> ORGANISM: Homo sapiens

<400> SEQUENCE: 23

```
ccggaaattg gccgccgccg ccgccgccgc gccgagcgga ggaggaggag gaggcgagga      60
ggagagactg ctccataaaa atacagactc accagttcct gctttgatgt gacatgtgac    120
tccccagaat acaccttgct tctgtagacc agctccaaca ggattccatg gtagctggga    180
tgttagggct cagggaagaa aagtcagaag accaggacct ccagggcctc aaggacaaac    240
ccctcaagtt taaaaggtg aagaaagata agaaagaaga gaaagagggc aagcatgagc    300
ccgtgcagcc atcagcccac cactctgctg agcccgcaga ggcaggcaaa gcagagacat    360
cagaagggtc aggctccgcc ccggctgtgc cggaagcttc tgcctccccc aaacagcggc    420
gctccatcat ccgtgaccgg ggacccatgt atgatgaccc caccctgcct gaaggctgga    480
cacggaagct taagcaaagg aaatctggcc gctctgctgg aagtatgat gtgtatttga    540 tcaatcccca gggaaaagcc tttgctctca agtggagtt gattgcgtac ttcgaaaagg    600 taggcgcacac atccctggac cctaatgatt ttgacttcac ggtaactggg agagggagcc    660
cctcccggcg agagcagaaa ccacctaaga agcccaaatc tcccaaagct ccaggaactg    720
```

```
gcagaggccg gggacgcccc aaagggagcg gcaccacgag acccaaggcg gccacgtcag    780
agggtgtgca ggtgaaaagg gtcctggaga aaagtcctgg gaagctcctt gtcaagatgc    840
cttttcaaac ttcgccaggg ggcaaggctg aggggggtgg ggccaccaca tccacccagg    900
tcatggtgat caaacgcccc ggcaggaagc gaaaagctga ggccgaccct caggccattc    960
ccaagaaacg gggccgaaag ccggggagtg tggtggcagc cgctgccgcc gaggccaaaa   1020
agaaagccgt gaaggagtct tctatccgat ctgtgcagga gaccgtactc cccatcaaga   1080
agcgcaagac ccgggagacg gtcagcatcg aggtcaagga agtggtgaag cccctgctgg   1140
tgtccaccct cggtgagaag agcgggaaag gactgaagac ctgtaagagc cctgggcgga   1200
aaagcaagga gagcagcccc aaggggcgca gcagcagcgc ctcctcaccc cccaagaagg   1260
agcaccacca ccatcaccac cactcagagt ccccaaaggc cccgtgcca ctgctcccac   1320 ccctgccccc acctccacct gagcccgaga gctccgagga cccaccagc ccccctgagc   1380 cccaggactt gagcagcagc gtctgcaaag aggagaagat gccagagga ggctcactgg   1440 agagcgacgg ctgccccaag gagccagcta agactcagcc cgcggttgcc accgccgcca   1500
cggccgcaga aaagtacaaa caccgagggg agggagagcg caaagacatt gtttcatcct   1560
ccatgccaag gccaaacaga gaggagcctg tggacagccg gacgcccgtg accgagagag   1620
ttagctgact ttacacggag cggattgcaa agcaaaccaa caagaataaa ggcagctgtt   1680
gtctcttctc cttatgggta gggctctgac aaagcttccc gattaactga aataaaaaat   1740 atttttttt ctttcagtaa acttagagtt tcgtggcttc agggtgggag tagttggagc   1800
attggggatg ttttttcttac cgacaagcac agtcaggttg aagacctaac cagggccaga   1860
agtagctttg cacttttcta aactaggctc cttcaacaag gcttgctgca gatactactg   1920
accagacaag ctgttgacca ggcacctccc ctcccgccca aaccttcccc ccatgtggtc   1980
gttagagaca gagcgacaga gcagttgaga ggacactccc gttttcggtg ccatcagtgc   2040
cccgtctaca gctccccag ctccccccac ctccccact cccaaccacg ttgggacagg   2100
gaggtgtgag gcaggagaga cagttggatt ctttagagaa gatggatatg accagtggct   2160
atggcctgtg cgatcccacc cgtggtggct caagtctggc cccacaccag ccccaatcca   2220
aaactggcaa ggacgcttca caggacagga aagtggcacc tgtctgctcc agctctggca   2280
tggctaggag ggggagtcc cttgaactac tgggtgtaga ctggcctgaa ccacaggaga   2340
ggatggccca gggtgaggtg gcatggtcca ttctcaaggg acgtcctcca acgggtggcg   2400
ctagaggcca tggaggcagt aggacaaggt gcagcaggc tggcctgggg tcaggccggg   2460
cagagcacag cggggtgaga gggattccta atcactcaga gcagtctgtg acttagtgga   2520
caggggaggg ggcaaagggg gaggagaaga aaatgttctt ccagttactt tccaattctc   2580
ctttagggac agcttagaat tatttgcact attgagtctt catgttccca cttcaaaaca   2640
aacagatgct ctgagagcaa actggcttga attggtgaca tttagtccct caagccacca   2700
gatgtgacag tgttgagaac tacctggatt tgtatatata cctgcgcttg ttttaaagtg   2760
ggctcagcac atagggttcc cacgaagctc cgaaactcta agtgtttgct gcaattttat   2820
aaggacttcc tgattggttt ctcttctccc cttccatttc tgcctttgt tcatttcatc   2880 ctttcacttc tttcccttcc tccgtcctcc tccttcctag ttcatcccctt ctcttccagg   2940 cagccgcggt gccaaccac acttgtcggc tccagtcccc agaactctgc ctgccctttg   3000
tcctcctgct gccagtacca gccccaccct gttttgagcc ctgaggaggc cttgggctct   3060
```

```
gctgagtccg acctggcctg tctgtgaaga gcaagagagc agcaaggtct tgctctccta    3120
ggtagccccc tcttccctgg taagaaaaag caaaaggcat ttcccaccct gaacaacgag    3180
ccttttcacc cttctactct agagaagtgg actggaggag ctgggcccga tttggtagtt    3240
gaggaaagca cagaggcctc ctgtggcctg ccagtcatcg agtggcccaa caggggctcc    3300
atgccagccg accttgacct cactcagaag tccagagtct agcgtagtgc agcagggcag    3360
tagcggtacc aatgcagaac tcccaagacc cgagctggga ccagtacctg gtccccagc    3420
ccttcctctg ctcccccttt tccctcggag ttcttcttga atggcaatgt tttgcttttg    3480
ctcgatgcag acaggggggcc agaacaccac acatttcact gtctgtctgg tccatagctg    3540
tggtgtaggg gcttagaggc atgggcttgc tgtgggtttt taattgatca gttttcatgt    3600
gggatcccat cttttttaacc tctgttcagg aagtccttat ctagctgcat atcttcatca    3660
tattggtata tccttttctg tgtttacaga gatgtctctt atatctaaat ctgtccaact    3720
gagaagtacc ttatcaaagt agcaaatgag acagcagtct tatgcttcca gaaacaccca    3780
caggcatgtc ccatgtgagc tgctgccatg aactgtcaag tgtgtgttgt cttgtgtatt    3840
tcagttattg ccctggctt ccttactatg gtgtaatcat gaaggagtga aacatcatag    3900
aaactgtcta gcacttcctt gccagtcttt agtgatcagg aaccatagtt gacagttcca    3960
atcagtagct taagaaaaaa ccgtgtttgt ctcttctgga atggttagaa gtgagggagt    4020
ttgccccgtt ctgtttgtag agtctctag ttggactttc tagcatatat gtgtccattt    4080
ccttatgctg taaaagcaag tcctgcaacc aaactcccat cagcccaatc cctgatccct    4140
gatcccttcc acctgctctg ctgatgaccc ccccagcttc acttctgact cttccccagg    4200
aagggaaggg gggtcagaag agagggtgag tcctccagaa ctcttcctcc aaggacagaa    4260
ggctcctgcc cccatagtgg cctcgaactc ctggcactac caaaggacac ttatccacga    4320
gagcgcagca tccgaccagg ttgtcactga aagatgttt attttggtca gttgggtttt    4380
tatgtattat acttagtcaa atgtaatgtg gcttctggaa tcattgtcca gagctgcttc    4440
cccgtcacct gggcgtcatc tggtcctggt aagaggagtg cgtggcccac caggcccccc    4500
tgtcacccat gacagttcat tcagggccga tggggcagtc gtggttggga acacagcatt    4560
tcaagcgtca ctttatttca ttcgggcccc acctgcagct ccctcaaaga ggcagttgcc    4620
cagcctcttt cccttccagt ttattccaga gctgccagtg gggcctgagg ctccttaggg    4680
ttttctctct atttccccct tcttcctca ttccctcgtc tttcccaaag gcatcacgag    4740
tcagtcgcct ttcagcaggc agccttggcg gtttatcgcc ctggcaggca ggggccctgc    4800
agctctcatg ctgcccctgc cttggggtca ggttgacagg aggttggagg gaaagcctta    4860
agctgcagga ttctcaccag ctgtgtccgg cccagttttg gggtgtgacc tcaatttcaa    4920
ttttgtctgt acttgaacat tatgaagatg ggggcctctt tcagtgaatt tgtgaacagc    4980
agaattgacc gacagctttc cagtacccat ggggctaggt cattaaggcc acatccacag    5040
tctcccccac ccttgttcca gttgttagtt actacctcct ctcctgacaa tactgtatgt    5100
cgtcgagctc cccccaggtc tacccctccc ggccctgcct gctggtgggc тtgtcataгc    5160
cagtgggatt gccggtcttg acagctcagt gagctggaga tacttggtca cagccaggcg    5220
ctagcacagc tcccttctgt tgatgctgta ttcccatatc aaaagacaca ggggacaccc    5280
agaaacgcca catcccccaa tccatcagtg ccaaactagc caacggcccc agcttctcag    5340
ctcgctggat ggcggaagct gctactcgtg agcgccagtg cgggtgcaga caatcttctg    5400
ttgggtggca tcattccagg cccgaagcat gaacagtgca cctgggacag ggagcagccc    5460
```

| | |
|---|---|
| caaattgtca cctgcttctc tgcccagctt ttcattgctg tgacagtgat ggcgaaagag | 5520 |
| ggtaataacc agacacaaac tgccaagttg ggtggagaaa ggagtttctt tagctgacag | 5580 |
| aatctctgaa ttttaaatca cttagtaagc ggctcaagcc caggagggag cagagggata | 5640 |
| cgagcggagt cccctgcgcg ggaccatctg gaattggttt agcccaagtg gagcctgaca | 5700 |
| gccagaactc tgtgtccccc gtctaaccac agctccttt ccagagcatt ccagtcaggc | 5760 |
| tctctgggct gactgggcca ggggaggtta caggtaccag ttctttaaga agatctttgg | 5820 |
| gcatatacat ttttagcctg tgtcattgcc ccaaatggat tcctgtttca agttcacacc | 5880 |
| tgcagattct aggacctgtg tcctagactt cagggagtca gctgtttcta gagttcctac | 5940 |
| catggagtgg gtctggagga cctgcccggt ggggggcag agccctgctc cctccgggtc | 6000 |
| ttcctactct tctctctgct ctgacgggat ttgttgattc tctccatttt ggtgtctttc | 6060 |
| tcttttagat attgtatcaa tctttagaaa aggcatagtc tacttgttat aaatcgttag | 6120 |
| gatactgcct cccccagggt ctaaaattac atattagagg ggaaaagctg aacactgaag | 6180 |
| tcagttctca acaatttaga aggaaaacct agaaaacatt tggcagaaaa ttacatttcg | 6240 |
| atgttttga atgaatacga gcaagctttt acaacagtgc tgatctaaaa atacttagca | 6300 |
| cttggcctga gatgcctggt gagcattaca ggcaagggga atctggaggt agccgacctg | 6360 |
| aggacatggc ttctgaacct gtcttttggg agtggtatgg aaggtggagc gttcaccagt | 6420 |
| gacctggaag gcccagcacc accctccttc ccactcttct catcttgaca gagcctgccc | 6480 |
| cagcgctgac gtgtcaggaa aacacccagg gaactaggaa ggcacttctg cctgaggggc | 6540 |
| agcctgcctt gcccactcct gctctgctcg cctcggatca gctgagcctt ctgagctggc | 6600 |
| ctctcactgc ctccccaagg cccctgcct gccctgtcag gaggcagaag gaagcaggtg | 6660 |
| tgagggcagt gcaaggaggg agcacaaccc ccagctcccg ctccgggctc cgacttgtgc | 6720 |
| acaggcagag cccagaccct ggaggaaatc ctacctttga attcaagaac atttggggaa | 6780 |
| tttggaaatc tctttgcccc caaaccccca ttctgtccta cctttaatca ggtcctgctc | 6840 |
| agcagtgaga gcagatgagg tgaaaaggcc aagaggtttg gctcctgccc actgatagcc | 6900 |
| cctctccccg cagtgtttgt gtgtcaagtg gcaaagctgt tcttcctggt gaccctgatt | 6960 |
| atatccagta acacatagac tgtgcgcata ggcctgcttt gtctcctcta tcctgggctt | 7020 |
| ttgttttgct ttttagttt gcttttagtt ttctgtccc ttttatttaa cgcaccgact | 7080 |
| agacacacaa agcagttgaa tttttatata tatatctgta tattgcacaa ttataaactc | 7140 |
| attttgcttg tggctccaca cacacaaaaa aagacctgtt aaaattatac ctgttgctta | 7200 |
| attacaatat ttctgataac catagcatag gacaagggaa aataaaaaaa gaaaaaaaag | 7260 |
| aaaaaaaaac gacaaatctg tctgctggtc acttcttctg tccaagcaga ttcgtggtct | 7320 |
| tttcctcgct tctttcaagg gctttcctgt gccaggtgaa ggaggctcca ggcagcaccc | 7380 |
| aggttttgca ctcttgtttc tcccgtgctt gtgaaagagg tcccaaggtt ctgggtgcag | 7440 |
| gagcgctccc ttgacctgct gaagtccgga acgtagtcgg cacagcctgg tcgccttcca | 7500 |
| cctctgggag ctggagtcca ctggggtggc ctgactcccc cagtccccctt cccgtgacct | 7560 |
| ggtcagggtg agcccatgtg gagtcagcct cgcaggcctc cctgccagta gggtccgagt | 7620 |
| gtgtttcatc cttcccactc tgtcgagcct gggggctgga gcggagacgg gaggcctggc | 7680 |
| ctgtctcgga acctgtgagc tgcaccaggt agaacgccag ggaccccaga atcatgtgcg | 7740 |
| tcagtccaag gggtcccctc caggagtagt gaagactcca gaaatgtccc tttcttctcc | 7800 |

```
cccatcctac gagtaattgc atttgctttt gtaattctta atgagcaata tctgctagag   7860
agtttagctg taacagttct ttttgatcat cttttttaa taattagaaa caccaaaaaa    7920
atccagaaac ttgttcttcc aaagcagaga gcattataat caccagggcc aaaagcttcc   7980
ctccctgctg tcattgcttc ttctgaggcc tgaatccaaa agaaaaacag cataggccc    8040
tttcagtggc cgggctaccc gtgagccctt cggaggacca gggctggggc agcctctggg   8100
cccacatccg gggccagctc cggcgtgtgt tcagtgttag cagtgggtca tgatgctctt   8160
tcccacccag cctgggatag gggcagagga ggcgaggagg ccgttgccgc tgatgtttgg   8220
ccgtgaacag gtgggtgtct gcgtgcgtcc acgtgcgtgt tttctgactg acatgaaatc   8280
gacgcccgag ttagcctcac ccggtgacct ctagccctgc ccggatggag cggggcccac   8340
ccggttcagt gtttctgggg agctggacag tggagtgcaa aaggcttgca gaacttgaag   8400
cctgctcctt cccttgctac cacggcctcc tttccgtttg atttgtcact gcttcaatca   8460
ataacagccg ctccagagtc agtagtcaat gaatatatga ccaaatatca ccaggactgt   8520
tactcaatgt gtgccgagcc cttgcccatg ctgggctccc gtgtatctgg acactgtaac   8580
gtgtgctgtg tttgctcccc ttccccttcc ttctttgccc tttacttgtc tttctggggt   8640
ttttctgttt gggtttggtt tggttttat ttctcctttt gtgttccaaa catgaggttc    8700
tctctactgg tcctcttaac tgtggtgttg aggcttatat ttgtgtaatt tttggtgggt   8760
gaaaggaatt ttgctaagta aatctcttct gtgtttgaac tgaagtctgt attgtaacta   8820
tgttaaagt aattgttcca gagacaaata tttctagaca cttttctttt acaaacaaaa    8880
gcattcggag ggagggggat ggtgactgag atgagagggg agagctgaac agatgacccc   8940
tgcccagatc agccagaagc cacccaaagc agtggagccc aggagtccca ctccaagcca   9000
gcaagccgaa tagctgatgt gttgccactt tccaagtcac tgcaaaacca ggttttgttc   9060
cgcccagtgg attcttgttt tgcttcccct cccccgaga ttattaccac catcccgtgc    9120
ttttaaggaa aggcaagatt gatgtttcct tgaggggagc caggagggga tgtgtgtgtg   9180
cagagctgaa gagctgggga gaatgggggct gggcccaccc aagcaggagg ctgggacgct  9240
ctgctgtggg cacaggtcag gctaatgttg gcagatgcag ctcttcctgg acaggccagg   9300
tggtgggcat tctctctcca aggtgtgccc cgtgggcatt actgtttaag cacttccgt    9360
cacatcccac cccatcctcc agggctcaac actgtgacat ctctattccc cacccctcccc  9420
tcccagggc aataaaatga ccatggaggg ggcttgcact ctcttggctg tcaccgatc     9480
gccagcaaaa cttagatgtg agaaaacccc ttcccattcc atggcgaaaa catctcctta   9540
gaaaagccat taccctcatt aggcatggtt ttgggctccc aaaacacctg acagcccctc   9600
cctcctctga gaggcggaga gtgctgactg tagtgaccat tgcatgccgg gtgcagcatc   9660
tggaagagct aggcagggtg tctgccccct cctgagttga agtcatgctc ccctgtgcca   9720
gcccagaggc cgagagctat ggacagcatt gccagtaaca caggccaccc tgtgcagaag   9780
ggagctggct ccagcctgga aacctgtctg aggttgggag aggtgcactt ggggcacagg   9840
gagaggccgg gacacactta gctggagatg tctctaaaag ccctgtatcg tattcacctt   9900
cagtttttgt gttttgggac aattacttta gaaataagt aggtcgtttt aaaaacaaaa    9960
attattgatt gcttttttgt agtgttcaga aaaaggttc tttgtgtata gccaaatgac    10020
tgaaagcact gatatattta aaacaaaag gcaatttatt aaggaaattt gtaccatttc    10080
agtaaacctg tctgaatgta cctgtatacg tttcaaaaac ccccccccc cactgaatcc    10140
ctgtaaccta tttattatat aaagagtttg ccttataaat tt                      10182
```

<210> SEQ ID NO 24
<211> LENGTH: 10180
<212> TYPE: DNA
<213> ORGANISM: Homo sapiens

<400> SEQUENCE: 24

| | | | | | |
|---|---|---|---|---|---|
| ccggaaaatg | gccgccgccg | ccgccgccgc | gccgagcgga | ggaggaggag | gaggcgagga | 60 |
| ggagagacct | ccataaaaat | acagactcac | cagttcctgc | tttgatgtga | catgtgactc | 120 |
| cccagaatac | accttgcttc | tgtagaccag | ctccaacagg | attccatggt | agctgggatg | 180 |
| ttagggctca | gggaagaaaa | gtcagaagac | caggacctcc | agggcctcaa | ggacaaaccc | 240 |
| ctcaagttta | aaaaggtgaa | gaaagataag | aaagaagaga | agagggcaa | gcatgagccc | 300 |
| gtgcagccat | cagcccacca | ctctgctgag | cccgcagagg | caggcaaagc | agagacatca | 360 |
| gaagggtcag | gctccgcccc | ggctgtgccg | gaagcttctg | cctcccccaa | acagcggcgc | 420 |
| tccatcatcc | gtgaccgggg | acccatgtat | gatgacccca | ccctgcctga | aggctggaca | 480 |
| cggaagctta | agcaaaggaa | atctggccgc | tctgctggga | agtatgatgt | gtatttgatc | 540 |
| aatccccagg | gaaaagcctt | tcgctctaaa | gtggagttga | ttgcgtactt | cgaaaaggta | 600 |
| ggcgacacat | ccctggaccc | taatgatttt | gacttcacgg | taactgggag | agggagcccc | 660 |
| tcccggcgag | agcagaaacc | acctaagaag | cccaaatctc | ccaaagctcc | aggaactggc | 720 |
| agaggccggg | gacgccccaa | agggagcggc | accacgagac | ccaaggcggc | cacgtcagag | 780 |
| ggtgtgcagg | tgaaaagggt | cctggagaaa | agtcctggga | agctccttgt | caagatgcct | 840 |
| tttcaaactt | cgccaggggg | caaggctgag | ggggtgggg | ccaccacatc | cacccaggtc | 900 |
| atggtgatca | acgccccgg | caggaagcga | aaagctgagg | ccgaccctca | ggccattccc | 960 |
| aagaaacggg | gccgaaagcc | ggggagtgtg | gtggcagccg | ctgccgccga | ggccaaaaag | 1020 |
| aaagccgtga | aggagtcttc | tatccgatct | gtgcaggaga | ccgtactccc | catcaagaag | 1080 |
| cgcaagaccc | gggagacggt | cagcatcgag | gtcaaggaag | tggtgaagcc | cctgctggtg | 1140 |
| tccaccctcg | gtgagaagag | cgggaaagga | ctgaagacct | gtaagagccc | tgggcggaaa | 1200 |
| agcaaggaga | gcagccccaa | ggggcgcagc | agcagcgcct | cctcaccccc | caagaaggag | 1260 |
| caccaccacc | atcaccacca | ctcagagtcc | ccaaaggccc | ccgtgccact | gctcccaccc | 1320 |
| ctgccccac | ctccacctga | gcccgagagc | tccgaggacc | ccaccagccc | cctgagccc | 1380 |
| caggacttga | gcagcagcgt | ctgcaaagag | gagaagatgc | ccagaggagg | ctcactggag | 1440 |
| agcgacggct | gccccaagga | gccagctaag | actcagcccg | cggttgccac | cgccgccacg | 1500 |
| gccgcagaaa | agtacaaaca | ccgaggggag | ggagagcgca | aagacattgt | tcatcctcc | 1560 |
| atgccaaggc | caaacagaga | ggagcctgtg | gacagccgga | cgcccgtgac | cgagagagtt | 1620 |
| agctgacttt | acacggagcg | gattgcaaag | caaaccaaca | agaataaagg | cagctgttgt | 1680 |
| ctcttctcct | tatgggtagg | gctctgacaa | agcttcccga | ttaactgaaa | taaaaaatat | 1740 |
| ttttttttct | ttcagtaaac | ttagagtttc | gtggcttcag | ggtgggagta | gttggagcat | 1800 |
| tgggatgtt | tttcttaccg | acaagcacag | tcaggttgaa | gacctaacca | gggccagaag | 1860 |
| tagctttgca | cttttctaaa | ctaggctcct | tcaacaaggc | ttgctgcaga | tactactgac | 1920 |
| cagacaagct | gttgaccagg | cacctcccct | cccgcccaaa | cctttccccc | atgtggtcgt | 1980 |
| tagagacaga | gcgacagagc | agttgagagg | acactcccgt | tttcggtgcc | atcagtgccc | 2040 |
| cgtctacagc | tcccccagct | cccccacct | cccccactcc | caaccacgtt | gggacaggga | 2100 |

```
ggtgtgaggc aggagagaca gttggattct ttagagaaga tggatatgac cagtggctat    2160
ggcctgtgcg atcccacccg tggtggctca agtctggccc cacaccagcc ccaatccaaa    2220
actggcaagg acgcttcaca ggacaggaaa gtggcacctg tctgctccag ctctggcatg    2280
gctaggaggg gggagtccct tgaactactg ggtgtagact ggcctgaacc acaggagagg    2340
atggcccagg gtgaggtggc atggtccatt ctcaagggac gtcctccaac gggtggcgct    2400
agaggccatg gaggcagtag gacaaggtgc aggcaggctg gcctgggtc aggccgggca    2460 gagcacagcg gggtgagagg gattcctaat cactcagagc agtctgtgac ttagtggaca    2520
ggggaggggg caaaggggga ggagaagaaa atgttcttcc agttactttc caattctcct    2580
ttagggacag cttagaatta tttgcactat tgagtcttca tgttcccact tcaaaacaaa    2640
cagatgctct gagagcaaac tggcttgaat tggtgacatt tagtccctca agccaccaga    2700
tgtgacagtg ttgagaacta cctggatttg tatatatacc tgcgcttgtt ttaaagtggg    2760
ctcagcacat agggttccca cgaagctccg aaactctaag tgtttgctgc aattttataa    2820
ggacttcctg attggtttct cttctcccct tccatttctg cctttttgttc atttcatcct    2880 ttcacttctt tcccttcctc cgtcctcctc cttcctagtt catcccttct cttccaggca    2940
gccgcggtgc ccaaccacac ttgtcggctc cagtccccag aactctgcct gcccttttgtc    3000 ctcctgctgc cagtaccagc cccacccctgt tttgagccct gaggaggcct tgggctctgc    3060
tgagtccgac ctggcctgtc tgtgaagagc aagagagcag caaggtcttg ctctcctagg    3120
tagccccctc ttccctggta agaaaaagca aaaggcattt cccaccctga caacgagcc    3180 ttttcaccct tctactctag agaagtggac tggaggagct gggcccgatt tggtagttga    3240
ggaaagcaca gaggcctcct gtggcctgcc agtcatcgag tggcccaaca ggggctccat    3300
gccagccgac cttgacctca ctcagaagtc cagagtctag cgtagtgcag cagggcagta    3360
gcggtaccaa tgcagaactc ccaagacccg agctgggacc agtacctggg tccccagccc    3420
ttcctctgct cccccttttc cctcggagtt cttcttgaat ggcaatgttt tgcttttgct    3480
cgatgcagac agggggccag aacaccacac atttcactgt ctgtctggtc catagctgtg    3540
gtgtaggggc ttagaggcat gggcttgctg tgggttttta attgatcagt tttcatgtgg    3600
gatcccatct tttaaacctc tgttcaggaa gtccttatct agctgcatat cttcatcata    3660
ttggtatatc cttttctgtg tttacagaga tgtctcttat atctaaatct gtccaactga    3720
gaagtacctt atcaaagtag caaatgagac agcagtctta tgcttccaga aacacccaca    3780
ggcatgtccc atgtgagctg ctgccatgaa ctgtcaagtg tgtgttgtct tgtgtatttc    3840
agttattgtc cctggcttcc ttactatggt gtaatcatga aggagtgaaa catcatagaa    3900
actgtctagc acttccttgc cagtctttag tgatcaggaa ccatagttga cagttccaat    3960
cagtagctta agaaaaaacc gtgtttgtct cttctggaat ggttagaagt gagggagttt    4020
gccccgttct gtttgtagag tctcatagtt ggactttcta gcatatatgt gtccatttcc    4080
ttatgctgta aaagcaagtc ctgcaaccaa actcccatca gcccaatccc tgatccctga    4140
tcccttccac ctgctctgct gatgaccccc ccagcttcac ttctgactct tccccaggaa    4200
gggaaggggg gtcagaagag agggtgagtc ctccagaact cttcctccaa ggacagaagg    4260
ctcctgcccc catagtggcc tcgaactcct ggcactacca aaggacactt atccacgaga    4320
gcgcagcatc cgaccaggtt gtcactgaga agatgtttat tttggtcagt tgggttttta    4380
tgtattatac ttagtcaaat gtaatgtggc ttctggaatc attgtccaga gctgcttccc    4440
cgtcacctgg gcgtcatctg gtcctggtaa gaggagtgcg tggcccacca ggccccctg    4500
```

```
tcacccatga cagttcattc agggccgatg gggcagtcgt ggttgggaac acagcatttc    4560
aagcgtcact ttatttcatt cgggcccac ctgcagctcc ctcaaagagg cagttgccca    4620
gcctctttcc cttccagttt attccagagc tgccagtggg gcctgaggct ccttagggtt    4680
ttctctctat ttcccccttt cttcctcatt ccctcgtctt tcccaaaggc atcacgagtc    4740
agtcgccttt cagcaggcag ccttggcggt ttatcgccct ggcaggcagg ggccctgcag    4800
ctctcatgct gccctgcct tggggtcagg ttgacaggag gttggaggga aagccttaag    4860
ctgcaggatt ctcaccagct gtgtccggcc cagttttggg gtgtgacctc aatttcaatt    4920
ttgtctgtac ttgaacatta tgaagatggg ggcctctttc agtgaatttg tgaacagcag    4980
aattgaccga cagctttcca gtacccatgg ggctaggtca ttaaggccac atccacagtc    5040
tcccccaccc ttgttccagt tgttagttac tacctcctct cctgacaata ctgtatgtcg    5100
tcgagctccc cccaggtcta cccctcccgg ccctgcctgc tggtgggctt gtcatagcca    5160
gtgggattgc cggtcttgac agctcagtga gctggagata cttggtcaca gccaggcgct    5220
agcacagctc ccttctgttg atgctgtatt cccatatcaa aagacacagg ggacacccag    5280
aaacgccaca tcccccaatc catcagtgcc aaactagcca acggcccag cttctcagct    5340 cgctggatgg cggaagctgc tactcgtgag cgccagtgcg ggtgcagaca atcttctgtt    5400
gggtggcatc attccaggcc cgaagcatga acagtgcacc tgggacaggg agcagcccca    5460
aattgtcacc tgcttctctg cccagctttt cattgctgtg acagtgatgg cgaaagaggg    5520
taataaccag acacaaactg ccaagttggg tggagaaagg agtttctta gctgacagaa    5580 tctctgaatt ttaaatcact tagtaagcgg ctcaagccca ggagggagca gagggatacg    5640
agcggagtcc cctgcgcggg accatctgga attggtttag cccaagtgga gcctgacagc    5700
cagaactctg tgtcccccgt ctaaccacag ctccttttcc agagcattcc agtcaggctc    5760
tctgggctga ctgggccagg ggaggttaca ggtaccagtt ctttaagaag atctttgggc    5820
atatacattt ttagcctgtg tcattgcccc aaatggattc ctgtttcaag ttcacacctg    5880
cagattctag gacctgtgtc ctagacttca gggagtcagc tgtttctaga gttcctacca    5940
tggagtgggt ctggaggacc tgcccggtgg ggggcagag ccctgctccc tccgggtctt    6000
cctactcttc tctctgctct gacgggattt gttgattctc tccattttgg tgtctttctc    6060
ttttagatat tgtatcaatc tttagaaaag gcatagtcta cttgttataa atcgttagga    6120
tactgcctcc cccagggtct aaaattacat attagagggg aaaagctgaa cactgaagtc    6180
agttctcaac aatttagaag gaaacctag aaaacatttg gcagaaaatt acatttcgat    6240
gtttttgaat gaatacgagc aagcttttac aacagtgctg atctaaaaat acttagcact    6300
tggcctgaga tgcctggtga gcattacagg caagggaat ctggaggtag ccgacctgag    6360
gacatggctt ctgaacctgt cttttgggag tggtatggaa ggtggagcgt tcaccagtga    6420
cctggaaggc ccagcaccac cctccttccc actcttctca tcttgacaga gcctgcccca    6480
gcgctgacgt gtcaggaaaa cacccaggga actaggaagg cacttctgcc tgagggcag    6540 cctgccttgc ccactcctgc tctgctcgcc tcggatcagc tgagccttct gagctggcct    6600
ctcactgcct cccaaggcc ccctgcctgc cctgtcagga ggcagaagga agcaggtgtg    6660
agggcagtgc aaggagggag cacaaccccc agctcccgct ccgggctccg acttgtgcac    6720
aggcagagcc cagaccctgg aggaaatcct acctttgaat tcaagaacat ttggggaatt    6780
tggaaatctc tttgcccca aaccccccatt ctgtcctacc tttaatcagg tcctgctcag    6840
```

```
cagtgagagc agatgaggtg aaaaggccaa gaggtttggc tcctgcccac tgatagcccc    6900
tctccccgca gtgtttgtgt gtcaagtggc aaagctgttc ttcctggtga ccctgattat    6960
atccagtaac acatagactg tgcgcatagg cctgctttgt ctcctctatc ctgggctttt    7020
gttttgcttt ttagttttgc ttttagtttt tctgtcccct ttatttaacg caccgactag    7080
acacacaaag cagttgaatt tttatatata tatctgtata ttgcacaatt ataaactcat    7140
tttgcttgtg gctccacaca cacaaaaaaa gacctgttaa aattatacct gttgcttaat    7200
tacaatattt ctgataacca tagcatagga caagggaaaa taaaaaaaga aaaaaagaa    7260
aaaaaacga caaatctgtc tgctggtcac ttcttctgtc caagcagatt cgtggtcttt    7320
tcctcgcttc tttcaagggc tttcctgtgc caggtgaagg aggctccagg cagcacccag    7380
gttttgcact cttgtttctc ccgtgcttgt gaaagaggtc ccaaggttct gggtgcagga    7440
gcgctccctt gacctgctga agtccggaac gtagtcggca cagcctggtc gccttccacc    7500
tctgggagct ggagtccact ggggtggcct gactccccca gtccccttcc cgtgacctgg    7560
tcagggtgag cccatgtgga gtcagcctcg caggcctccc tgccagtagg gtccgagtgt    7620
gtttcatcct tcccactctg tcgagcctgg gggctggagc ggagacggga ggcctggcct    7680
gtctcggaac ctgtgagctg caccaggtag aacgccaggg accccagaat catgtgcgtc    7740
agtccaaggg gtcccctcca ggagtagtga agactccaga aatgtccctt tcttctcccc    7800
catcctacga gtaattgcat ttgcttttgt aattcttaat gagcaatatc tgctagagag    7860
tttagctgta acagttcttt ttgatcatct тттттттaaтa attagaaaca ccaaaaaaat    7920
ccagaaactt gttcttccaa agcagagagc attataatca ccagggccaa aagcttccct    7980
ccctgctgtc attgcttctt ctgaggcctg aatccaaaag aaaaacagcc ataggccctt    8040
tcagtggccg ggctacccgt gagcccttcg gaggaccagg gctggggcag cctctgggcc    8100
cacatccggg gccagctccg gcgtgtgttc agtgttagca gtgggtcatg atgctctttc    8160
ccacccagcc tgggataggg gcagaggagg cgaggaggcc gttgccgctg atgtttggcc    8220
gtgaacaggt gggtgtctgc gtgcgtccac gtgcgtgttt tctgactgac atgaaatcga    8280
cgcccgagtt agcctcaccc ggtgacctct agccctgccc ggatggagcg gggcccaccc    8340
ggttcagtgt ttctggggag ctggacagtg gagtgcaaaa ggcttgcaga acttgaagcc    8400
tgctccttcc cttgctacca cggcctcctt tccgtttgat tgtcactgc ttcaatcaat    8460
aacagccgct ccagagtcag tagtcaatga atatatgacc aaatatcacc aggactgtta    8520
ctcaatgtgt gccgagccct tgcccatgct gggctccgt gtatctggac actgtaacgt    8580
gtgctgtgtt tgctcccctt ccccttcctt ctttgccctt tacttgtctt tctggggttt    8640
ttctgtttgg gtttggtttg gtttttattt tccttttgt gttccaaaca tgaggttctc    8700
tctactggtc ctcttaactg tggtgttgag gcttatattt gtgtaatttt tggtgggtga    8760
aaggaatttt gctaagtaaa tctcttctgt gттттgaacтg aagtctgtat tgtaactatg    8820
ттт aaagtaa ttgttccaga gacaaatatt tctagacact tttt ctttac aaacaaaagc    8880
attcggaggg aggggatggg tgactgagat gagaggggag agctgaacag atgacccctg    8940
cccagatcag ccagaagcca cccaaagcag tggagcccag gagtcccact ccaagccagc    9000
aagccgaata gctgatgtgt tgccactttc caagtcactg caaaaccagg ttttgttccg    9060
cccagtggat tcttgtttt g cttcccctcc ccccgagatt attaccaca tcccgtgctt    9120
ttaaggaaag gcaagattga tgtttccttg aggggagcca ggaggggatg tgtgtgtgca    9180
gagctgaaga gctggggaga atggggctgg gcccacccaa gcaggaggct gggacgctct    9240
```

-continued

```
gctgtgggca caggtcaggc taatgttggc agatgcagct cttcctggac aggccaggtg   9300
gtgggcattc tctctccaag gtgtgccccg tgggcattac tgtttaagac acttccgtca   9360
catcccaccc catcctccag ggctcaacac tgtgacatct ctattcccca ccctcccctt   9420
cccagggcaa taaaatgacc atggaggggg cttgcactct cttggctgtc acccgatcgc   9480
cagcaaaact tagatgtgag aaaacccctt cccattccat ggcgaaaaca tctccttaga   9540
aaagccatta ccctcattag gcatggtttt gggctcccaa acacctgac agcccctccc    9600 tcctctgaga ggcggagagt gctgactgta gtgaccattg catgccgggt gcagcatctg   9660
gaagagctag gcagggtgtc tgcccccttc tgagttgaag tcatgctccc ctgtgccagc    9720
ccagaggccg agagctatgg acagcattgc cagtaacaca ggccaccctg tgcagaaggg   9780
agctggctcc agcctggaaa cctgtctgag gttgggagag gtgcacttgg ggcacaggga   9840
gaggccggga cacacttagc tggagatgtc tctaaaagcc ctgtatcgta ttcaccttca   9900 gttttttgtgt tttgggacaa ttactttaga aataagtag gtcgttttaa aaacaaaaat    9960
tattgattgc ttttttgtag tgttcagaaa aaaggttctt tgtgtatagc caaatgactg  10020
aaagcactga tatatttaaa aacaaaaggc aatttattaa ggaaatttgt accatttcag  10080
taaacctgtc tgaatgtacc tgtatacgtt tcaaaaacac ccccccccca ctgaatccct  10140
gtaacctatt tattatataa agagtttgcc ttataaattt                          10180
```

<210> SEQ ID NO 25
<211> LENGTH: 10191
<212> TYPE: DNA
<213> ORGANISM: Homo sapiens

<400> SEQUENCE: 25

```
ccggaaaatg gccgccgccg ccgccgccgc cgccgccgcg ccgagcggag gaggaggagg     60
aggcgaggag gagagactgc tccataaaaa tacagactca ccagttcctg ctttgatgtg    120
acatgtgact ccccagaata caccttgctt ctgtagacca gctccaacag gattccatgg    180
tagctgggat gttagggctc agggaagaaa agtcagaaga ccaggacctc cagggcctca    240
aggacaaacc cctcaagttt aaaaaggtga agaaagataa gaaagaagag aaagagggca    300
agcatgagcc cgtgcagcca tcagcccacc actctgctga gcccgcagag gcaggcaaag    360
cagagacatc agaagggtca ggctccgccc cggctgtgcc ggaagcttct gcctccccca    420
aacagcggcg ctccatcatc cgtgaccggg gacccatgta tgatgacccc accctgcctg    480
aaggctggac acgaagcttt aagcaaagga aatctggccg ctctgctggg aagtatgatg    540
tgtatttgat caatccccag ggaaaagcct ttcgctctaa agtggagttg attgcgtact    600
tcgaaaaggt aggcgacaca tccctggacc ctaatgattt tgacttcacg gtaactggga    660
gaggagcccc ctcccggcga gagcagaaac cacctaagaa gcccaaatct cccaaagctc    720
caggaactgg cagaggccgg ggacgcccca aggagcgg caccacgaga cccaaggcgg      780
ccacgtcaga gggtgtgcag gtgaaaaggg tcctggagaa aagtcctggg aagctccttg    840
tcaagatgcc ttttcaaact tcgccagggg gcaaggctga gggggtggg gccaccacat     900 ccacccaggt catggtgatc aaacgccccg gcaggaagcg aaaagctgag gccgacccctc   960 aggccattcc caagaaacgg ggccgaaagc cggggagtgt ggtggcagcc gctgccgccg   1020
aggccaaaaa gaaagccgtg aaggagtctt ctatccgatc tgtgcaggag accgtactcc   1080
ccatcaagaa gcgcaagacc cgggagacgg tcagcatcga ggtcaaggaa gtggtgaagc   1140
```

```
ccctgctggt gtccaccctc ggtgagaaga gcgggaaagg actgaagacc tgtaagagcc    1200
ctgggcggaa aagcaaggag agcagcccca aggggcgcag cagcagcgcc tcctcacccc    1260
ccaagaagga gcaccaccac catcaccacc actcagagtc cccaaaggcc cccgtgccac    1320
tgctcccacc cctgccccca cctccacctg agcccgagag ctccgaggac cccaccagcc    1380
cccctgagcc ccaggacttg agcagcagcg tctgcaaaga ggagaagatg cccagaggag    1440
gctcactgga gagcgacggc tgccccaagg agccagctaa gactcagccc gcggttgcca    1500
ccgccgccac ggccgcagaa aagtacaaac accgagggga gggagagcgc aaagacattg    1560
tttcatcctc catgccaagg ccaaacagag aggagcctgt ggacagccgg acgcccgtga    1620
ccgagagagt tagctgactt tacacggagc ggattgcaaa gcaaaccaac aagaataaag    1680
gcagctgttg tctcttctcc ttatgggtag ggctctgaca aagcttcccg attaactgaa    1740
ataaaaaata tttttttttc tttcagtaaa cttagagttt cgtggcttca gggtgggagt    1800
agttggagca ttggggatgt ttttcttacc gacaagcaca gtcaggttga agacctaacc    1860
agggccagaa gtagctttgc acttttctaa actaggctcc ttcaacaagg cttgctgcag    1920
atactactga ccagacaagc tgttgaccag gcacctcccc tcccgcccaa acctttcccc    1980
catgtggtcg ttagagacag agcgacagag cagttgagag gacactcccg ttttcggtgc    2040
catcagtgcc ccgtctacag ctcccccagc tcccccaccc tcccccactc ccaaccacgt    2100
tgggacaggg aggtgtgagg caggagagac agttggattc tttagagaag atggatatga    2160
ccagtggcta tggcctgtgc gatcccaccc gtggtggctc aagtctggcc ccacaccagc    2220
cccaatccaa aactggcaag gacgcttcac aggacaggaa agtggcacct gtctgctcca    2280
gctctggcat ggctaggagg ggggagtccc ttgaactact gggtgtagac tggcctgaac    2340
cacaggagag gatggcccag ggtgaggtgg catggtccat tctcaaggga cgtcctccaa    2400
cgggtggcgc tagaggccat ggaggcagta ggacaaggtg caggcaggct ggcctggggt    2460
caggccgggg agagcacagc ggggtgagag ggattcctaa tcactcagag cagtctgtga    2520
cttagtggac aggggagggg gcaaagggg g aggagaagaa aatgttcttc cagttacttt    2580
ccaattctcc tttagggaca gcttagaatt atttgcacta ttgagtcttc atgttcccac    2640
ttcaaaacaa acagatgctc tgagagcaaa ctggcttgaa ttggtgacat ttagtccctc    2700
aagccaccag atgtgacagt gttgagaact acctggattt gtatatatac ctgcgcttgt    2760
tttaaagtgg gctcagcaca tagggttccc acgaagctcc gaaactctaa gtgtttgctg    2820
caattttata aggacttcct gattggtttc tcttctcccc ttccattttct gccttttgtt    2880 catttcatcc tttcacttct ttcccttcct ccgtcctcct ccttcctagt tcatcccttc    2940
tcttccaggc agccgcggtg cccaaccaca cttgtcggct ccagtcccca gaactctgcc    3000 tgcccttttgt cctcctgctg ccagtaccag ccccacccctg ttttgagccc tgaggaggcc    3060
ttgggctctg ctgagtccga cctggcctgt ctgtgaagag caagagagca gcaaggtctt    3120
gctctcctag gtagccccct cttccctggt aagaaaaagc aaaaggcatt cccaccctg    3180 aacaacgagc cttttcaccc ttctactcta gagaagtgga ctggaggagc tgggcccgat    3240
ttggtagttg aggaaagcac agaggcctcc tgtggcctgc cagtcatcga gtggcccaac    3300 agggggctcca tgccagccga ccttgacctc actcagaagt ccagagtcta gcgtagtgca    3360
gcagggcagt agcggtacca atgcagaact cccaagaccc gagctgggac cagtacctgg    3420
gtccccagcc cttcctctgc tcccccttttt ccctcggagt tcttcttgaa tggcaatgtt    3480
ttgcttttgc tcgatgcaga cagggggcca gaacaccaca catttcactg tctgtctggt    3540
```

```
ccatagctgt ggtgtagggg cttagaggca tgggcttgct gtgggttttt aattgatcag    3600
ttttcatgtg ggatcccatc tttttaacct ctgttcagga agtccttatc tagctgcata    3660
tcttcatcat attggtatat ccttttctgt gtttacagag atgtctctta tatctaaatc    3720
tgtccaactg agaagtacct tatcaaagta gcaaatgaga cagcagtctt atgcttccag    3780
aaacacccac aggcatgtcc catgtgagct gctgccatga actgtcaagt gtgtgttgtc    3840
ttgtgtattt cagttattgt ccctggcttc cttactatgg tgtaatcatg aaggagtgaa    3900
acatcataga aactgtctag cacttccttg ccagtcttta gtgatcagga accatagttg    3960
acagttccaa tcagtagctt aagaaaaaac cgtgtttgtc tcttctggaa tggttagaag    4020
tgagggagtt tgccccgttc tgtttgtaga gtctcatagt tggactttct agcatatatg    4080
tgtccatttc cttatgctgt aaaagcaagt cctgcaacca aactcccatc agcccaatcc    4140
ctgatccctg atcccttcca cctgctctgc tgatgacccc cccagcttca cttctgactc    4200
ttccccagga agggaagggg ggtcagaaga gagggtgagt cctccagaac tcttcctcca    4260
aggacagaag gctcctgccc ccatagtggc ctcgaactcc tggcactacc aaaggacact    4320
tatccacgag agcgcagcat ccgaccaggt tgtcactgag aagatgttta ttttggtcag    4380
ttgggttttt atgtattata cttagtcaaa tgtaatgtgg cttctggaat cattgtccag    4440
agctgcttcc ccgtcacctg ggcgtcatct ggtcctggta agaggagtgc gtggcccacc    4500 aggccccct gtcacccatg acagttcatt cagggccgat ggggcagtcg tggttgggaa    4560
cacagcattt caagcgtcac tttatttcat tcgggcccca cctgcagctc cctcaaagag    4620
gcagttgccc agcctctttc ccttccagtt tattccagag ctgccagtgg ggcctgaggc    4680
tccttagggt tttctctcta tttccccctt tcttcctcat tccctcgtct ttcccaaagg    4740
catcacgagt cagtcgcctt tcagcaggca gccttggcgg tttatcgccc tggcaggcag    4800
gggccctgca gctctcatgc tgcccctgcc ttggggtcag gttgacagga ggttggaggg    4860
aaagccttaa gctgcaggat tctcaccagc tgtgtccggc ccagttttgg ggtgtgacct    4920
caatttcaat tttgtctgta cttgaacatt atgaagatgg gggcctcttt cagtgaattt    4980
gtgaacagca gaattgaccg acagctttcc agtacccatg gggctaggtc attaaggcca    5040
catccacagt ctccccccacc cttgttccag ttgttagtta ctacctcctc tcctgacaat    5100
actgtatgtc gtcgagctcc ccccaggtct acccctcccg gccctgcctg ctggtgggct    5160
tgtcatagcc agtgggattg ccggtcttga cagctcagtg agctggagat acttggtcac    5220
agccaggcgc tagcacagct cccttctgtt gatgctgtat tcccatatca aaagacacag    5280
gggacaccca gaaacgccac atcccccaat ccatcagtgc caaactagcc aacggcccca    5340
gcttctcagc tcgctggatg gcggaagctg ctactcgtga gcgccagtgc gggtgcagac    5400
aatcttctgt tgggtggcat cattccaggc ccgaagcatg aacagtgcac ctgggacagg    5460
gagcagcccc aaattgtcac ctgcttctct gcccagcttt tcattgctgt gacagtgatg    5520
gcgaaagagg gtaataacca gacacaaact gccaagttgg gtggagaaag gagtttcttt    5580
agctgacaga atctctgaat tttaaatcac ttagtaagcg gctcaagccc aggagggagc    5640
agagggatac gagcggagtc ccctgcgcgg gaccatctgg aattggttta gcccaagtgg    5700
agcctgacag ccagaactct gtgtcccccg tctaaccaca gctccttttc cagagcattc    5760
cagtcaggct ctctgggctg actgggccag gggaggttac aggtaccagt tctttaagaa    5820
gatctttggg catatacatt tttagcctgt gtcattgccc caaatggatt cctgtttcaa    5880
```

```
gttcacacct gcagattcta ggacctgtgt cctagacttc agggagtcag ctgtttctag    5940
agttcctacc atggagtggg tctggaggac ctgcccggtg ggggggcaga gccctgctcc    6000
ctccgggtct tcctactctt ctctctgctc tgacgggatt tgttgattct ctccattttg    6060
gtgtctttct cttttagata ttgtatcaat ctttagaaaa ggcatagtct acttgttata    6120
aatcgttagg atactgcctc ccccagggtc taaaattaca tattgagggg gaaaagctga    6180
acactgaagt cagttctcaa caatttagaa ggaaaaccta gaaaacattt ggcagaaaat    6240
tacatttcga tgttttttgaa tgaatacgag caagctttta caacagtgct gatctaaaaa    6300
tacttagcac ttggcctgag atgcctggtg agcattacag gcaaggggaa tctggaggta    6360
gccgacctga ggacatggct tctgaacctg tcttttggga gtggtatgga aggtggagcg    6420
ttcaccagtg acctgaaagg cccagcacca ccctccttcc cactcttctc atcttgacag    6480
agcctgcccc agcgctgacg tgtcaggaaa acacccaggg aactaggaag gcacttctgc    6540
ctgaggggca gcctgccttg cccactcctg ctctgctcgc ctcggatcag ctgagccttc    6600
tgagctggcc tctcactgcc tccccaaggc ccctgcctg cctgtcagg aggcagaagg    6660 aagcaggtgt gagggcagtg caaggaggga gcacaacccc cagctcccgc tccgggctcc    6720
gacttgtgca caggcagagc ccagaccctg gaggaaatcc tacctttgaa ttcaagaaca    6780
tttggggaat ttggaaatct cttttgccccc aaacccccat tctgtcctac ctttaatcag    6840
gtcctgctca gcagtgagag cagatgaggt gaaaaggcca agaggtttgg ctcctgccca    6900
ctgatagccc ctctccccgc agtgtttgtg tgtcaagtgg caaagctgtt cttcctggtg    6960
accctgatta tatccagtaa cacatagact gtgcgcatag gcctgctttg tctcctctat    7020
cctgggcttt tgttttgctt tttagttttg cttttagttt ttctgtccct tttatttaac    7080
gcaccgacta gacacacaaa gcagttgaat ttttatatat atatctgtat attgcacaat    7140
tataaactca ttttgcttgt ggctccacac acacaaaaaa agacctgtta aaattatacc    7200
tgttgcttaa ttacaatatt tctgataacc atagcatagg acaagggaaa ataaaaaaag    7260 aaaaaaaga aaaaaaaacg acaaatctgt ctgctggtca cttcttctgt ccaagcagat    7320
tcgtggtctt ttcctcgctt cttttcaaggg cttttcctgtg ccaggtgaag gaggctccag    7380
gcagcaccca ggttttgcac tcttgtttct cccgtgcttg tgaaagaggt cccaaggttc    7440
tgggtgcagg agcgctccct tgacctgctg aagtccggaa cgtagtcggc acagcctggt    7500
cgccttccac ctctgggagc tggagtccac tggggtggcc tgactccccc agtccccttc    7560
ccgtgacctg gtcagggtga gcccatgtgg agtcagcctc gcaggcctcc ctgccagtag    7620
ggtccgagtg tgtttcatcc ttcccactct gtcgagcctg ggggctggag cggagacggg    7680
aggcctggcc tgtctcggaa cctgtgagct gcaccaggta gaacgccagg gaccccagaa    7740
tcatgtgcgt cagtccaagg ggtcccctcc aggagtagtg aagactccag aaatgtccct    7800
ttcttctccc ccatcctacg agtaattgca tttgcttttg taattcttaa tgagcaatat    7860
ctgctagaga gtttagctgt aacagttctt tttgatcatc ttttttttaat aattagaaac    7920 accaaaaaaa tccagaaact tgttcttcca aagcagagag cattataatc accagggcca    7980
aaagcttccc tccctgctgt cattgcttct tctgaggcct gaatccaaaa gaaaaacagc    8040
cataggccct ttcagtggcc gggctacccg tgagcccttc ggaggaccag ggctggggca    8100
gcctctgggc ccacatccgg ggccagctcc ggcgtgtgtt cagtgttagc agtgggtcat    8160
gatgctcttt cccacccagc ctgggatagg ggcagaggag gcgaggaggc cgttgccgct    8220
gatgtttggc cgtgaacagg tgggtgtctg cgtgcgtcca cgtgcgtgtt ttctgactga    8280
```

| | |
|---|---|
| catgaaatcg acgcccgagt tagcctcacc cggtgacctc tagccctgcc cggatggagc | 8340 |
| ggggcccacc cggttcagtg tttctgggga gctggacagt ggagtgcaaa aggcttgcag | 8400 |
| aacttgaagc ctgctccttc ccttgctacc acggcctcct ttccgtttga tttgtcactg | 8460 |
| cttcaatcaa taacagccgc tccagagtca gtagtcaatg aatatatgac caaatatcac | 8520 |
| caggactgtt actcaatgtg tgccgagccc ttgcccatgc tgggctcccg tgtatctgga | 8580 |
| cactgtaacg tgtgctgtgt ttgctcccct tccccttcct tctttgccct ttacttgtct | 8640 |
| ttctggggtt tttctgtttg ggtttggttt ggttttttatt tctccttttg tgttccaaac | 8700 |
| atgaggttct ctctactggt cctcttaact gtggtgttga ggcttatatt tgtgtaattt | 8760 |
| ttggtgggtg aaaggaattt tgctaagtaa atctcttctg tgtttgaact gaagtctgta | 8820 |
| ttgtaactat gtttaaagta attgttccag agacaaatat ttctagacac ttttttcttta | 8880 |
| caaacaaaag cattcggagg gaggggggatg gtgactgaga tgagagggga gagctgaaca | 8940 |
| gatgaccccct gcccagatca gccagaagcc acccaaagca gtggagccca ggagtcccac | 9000 |
| tccaagccag caagccgaat agctgatgtg ttgccacttt ccaagtcact gcaaaaccag | 9060 |
| gttttgttcc gcccagtgga ttcttgtttt gcttcccctc cccccgagat tattaccacc | 9120 |
| atcccgtgct tttaaggaaa ggcaagattg atgtttcctt gaggggagcc aggaggggat | 9180 |
| gtgtgtgtgc agagctgaag agctggggag aatggggctg ggcccaccca agcaggaggc | 9240 |
| tgggacgctc tgctgtgggc acaggtcagg ctaatgttgg cagatgcagc tcttcctgga | 9300 |
| caggccaggt ggtgggcatt ctctctccaa ggtgtgcccc gtgggcatta ctgtttaaga | 9360 |
| cacttccgtc acatcccacc ccatcctcca gggctcaaca ctgtgacatc tctattcccc | 9420 |
| accctcccct tcccagggca ataaaatgac catggagggg gcttgcactc tcttggctgt | 9480 |
| cacccgatcg ccagcaaaac ttagatgtga gaaaacccct tcccattcca tggcgaaaac | 9540 |
| atctccttag aaaagccatt accctcatta ggcatggttt tgggctccca aaacacctga | 9600 |
| cagcccctcc ctcctctgag aggcggagag tgctgactgt agtgaccatt gcatgccggg | 9660 |
| tgcagcatct ggaagagcta ggcagggtgt ctgcccccctc ctgagttgaa gtcatgctcc | 9720 |
| cctgtgccag cccagaggcc gagagctatg acagcattg ccagtaacac aggccaccct | 9780 |
| gtgcagaagg gagctggctc cagcctggaa acctgtctga ggttgggaga ggtgcacttg | 9840 |
| gggcacaggg agaggccggg acacacttag ctggagatgt ctctaaaagc cctgtatcgt | 9900 |
| attccacttc agttttttgtg ttttgggaca attactttag aaaataagta ggtcgtttta | 9960 |
| aaaacaaaaa ttattgattg cttttttgta gtgttcagaa aaaaggttct ttgtgtatag | 10020 |
| ccaaatgact gaaagcactg atatatttaa aaacaaaagg caatttatta aggaaatttg | 10080 |
| taccatttca gtaaacctgt ctgaatgtac ctgtatacgt ttcaaaaaca cccccccccc | 10140 |
| actgaatccc tgtaacctat ttattatata aagagtttgc cttataaatt t | 10191 |

<210> SEQ ID NO 26
<211> LENGTH: 10179
<212> TYPE: DNA
<213> ORGANISM: Homo sapiens

<400> SEQUENCE: 26

| | |
|---|---|
| ccggaaaatg gccgccgccg ccgccgcgcc gagcggagga ggaggaggag gcgaggagga | 60 |
| gagactgctc cataaaaata cagactcacc agttcctgct ttgatgtgac atgtgactcc | 120 |
| ccagaataca ccttgcttct gtagaccagc tccaacagga ttccatggta gctgggatgt | 180 |

```
tagggctcag ggaagaaaag tcagaagacc aggacctcca gggcctcaag gacaaacccc   240
tcaagtttaa aaaggtgaag aaagataaga aagaagagaa agagggcaag catgagcccg   300
tgcagccatc agcccaccac tctgctgagc ccgcagaggc aggcaaagca gagacatcag   360
aagggtcagg ctccgccccg gctgtgccgg aagcttctgc ctcccccaaa cagcggcgct   420
ccatcatccg tgaccgggga cccatgtatg atgaccccac cctgcctgaa ggctggacac   480
ggaagcttaa gcaaaggaaa tctggccgct ctgctgggaa gtatgatgtg tatttgatca   540
atccccaggg aaaagccttt cgctctaaag tggagttgat tgcgtacttc gaaaaggtag   600
gcgacacatc cctggaccct aatgattttg acttcacggt aactgggaga gggagcccct   660
cccggcgaga gcagaaacca cctaagaagc ccaaatctcc caaagctcca ggaactggca   720
gaggccgggg acgccccaaa gggagcggca ccacgagacc caaggcggcc acgtcagagg   780
gtgtgcaggt gaaaagggtc ctggagaaaa gtcctgggaa gctccttgtc aagatgcctt   840
ttcaaacttc gccagggggc aaggctgagg ggggtgggc caccacatcc acccaggtca   900
tggtgatcaa acgccccggc aggaagcgaa agctgaggc cgaccctcag gccattccca   960
agaaacgggg ccgaaagccg gggagtgtgg tggcagccgc tgccgccgag gccaaaaaga  1020
aagccgtgaa ggagtcttct atccgatctg tgcaggagac cgtactcccc atcaagaagc  1080
gcaagacccg ggagacggtc agcatcgagg tcaaggaagt ggtgaagccc ctgctggtgt  1140
ccaccctcgg tgagaagagc gggaaaggac tgaagacctg taagagccct gggcggaaaa  1200
gcaaggagag cagccccaag gggcgcagca gcgcgcctc ctcacccccc aagaaggagc  1260
accaccacca tcaccaccac tcagagtccc caaaggcccc cgtgccactg ctcccacccc  1320 tgccccacc tccacctgag cccgagagct ccgaggaccc caccagcccc cctgagcccc  1380
aggacttgag cagcagcgtc tgcaaagagg agaagatgcc cagaggaggc tcactggaga  1440
gcgacggctg ccccaaggag ccagctaaga ctcagcccgc ggttgccacc gccgccacgg  1500
ccgcagaaaa gtacaaacac cgaggggagg gagagcgcaa agacattgtt tcatcctcca  1560
tgccaaggcc aaacagagag gagcctgtgg acagccggac gcccgtgacc gagagagtta  1620
gctgacttta cacggagcgg attgcaaagc aaaccaacaa gaataaaggc agctgttgtc  1680
tcttctcctt atgggtaggg ctctgacaaa gcttcccgat taactgaaat aaaaaatatt  1740 ttttttttctt tcagtaaact tagagttccg tggcttcagg gtgggagtag ttggagcatt  1800
ggggatgttt ttcttaccga caagcacagt caggttgaag acctaaccag ggccagaagt  1860
agctttgcac ttttctaaac taggctcctt caacaaggct tgctgcagat actactgacc  1920
agacaagctg ttgaccaggc acctcccctc ccgcccaaac ctttccccca tgtggtcgtt  1980
agagacagag cgacagagca gttgagagga cactcccgtt ttcggtgcca tcagtgcccc  2040
gtctacagct ccccagctc ccccacctc ccccactccc aaccacgttg ggacagggag  2100
gtgtgaggca ggagagacag ttggattctt tagagaagat ggatatgacc agtggctatg  2160
gcctgtgcga tcccacccgt ggtggctcaa gtctggcccc acaccagccc caatccaaaa  2220
ctggcaagga cgcttcacag gacaggaaag tggcacctgt ctgctccagc tctggcatgg  2280
ctaggagggg ggagtcccctt gaactactgg gtgtagactg gcctgaacca caggagagga  2340
tggcccaggg tgaggtggca tggtccattc tcaagggacg tcctccaacg ggtggcgcta  2400
gaggccatgg aggcagtagg acaaggtgca ggcaggctgg cctggggtca ggccgggcag  2460
agcacagcgg ggtgagaggg attcctaatc actcagcagca gtctgtgact tagtggacag  2520 ggggagggggc aaaggggag gagaagaaaa tgttcttcca gttactttcc aattctcctt  2580
```

```
tagggacagc ttagaattat ttgcactatt gagtcttcat gttcccactt caaaacaaac    2640
agatgctctg agagcaaact ggcttgaatt ggtgacattt agtccctcaa gccaccagat    2700
gtgacagtgt tgagaactac ctggatttgt atatatacct gcgcttgttt taaagtgggc    2760
tcagcacata gggttcccac gaagctccga aactctaagt gtttgctgca attttataag    2820
gacttcctga ttggtttctc ttctcccctt ccatttctgc cttttgttca tttcatcctt    2880
tcacttcttt cccttcctcc gtcctcctcc ttcctagttc atcccttctc ttccaggcag    2940
ccgcggtgcc aaccacact tgtcggctcc agtccccaga actctgcctg cccttctgtcc     3000 tcctgctgcc agtaccagcc ccaccctgtt ttgagccctg aggaggcctt gggctctgct    3060
gagtccgacc tggcctgtct gtgaagagca agagagcagc aaggtcttgc tctcctaggt    3120 agcccctct tccctggtaa gaaaagcaa aaggcatttc ccaccctgaa caacgagcct     3180 tttcacccctt ctactctaga aagtggact ggaggagctg ggcccgattt ggtagttgag    3240
gaaagcacag aggcctcctg tggcctgcca gtcatcgagt ggcccaacag gggctccatg    3300
ccagccgacc ttgacctcac tcagaagtcc agagtctagc gtagtgcagc agggcagtag    3360
cggtaccaat gcagaactcc caagacccga gctgggacca gtacctgggt ccccagccct    3420
tcctctgctc ccccttttcc ctcggagttc ttcttgaatg gcaatgtttt gcttttgctc    3480
gatgcagaca gggggccaga acaccacaca tttcactgtc tgtctggtcc atagctgtgg    3540
tgtaggggct tagaggcatg ggcttgctgt gggttttttaa ttgatcagtt ttcatgtggg    3600
atcccatctt tttaacctct gttcaggaag tccttatcta gctgcatatc ttcatcatat    3660
tggtatatcc ttttctgtgt ttacagagat gtctcttata tctaaatctg tccaactgag    3720
aagtacctta tcaaagtagc aaatgagaca gcagtcttat gcttccagaa acacccacag    3780
gcatgtccca tgtgagctgc tgccatgaac tgtcaagtgt gtgttgtctt gtgtatttca    3840
gttattgtcc ctggcttcct tactatggtg taatcatgaa ggagtgaaac atcatagaaa    3900
ctgtctagca cttccttgcc agtctttagt gatcaggaac catagttgac agttccaatc    3960
agtagcttaa gaaaaaaccg tgtttgtctc ttctggaatg gttagaagtg agggagtttg    4020
ccccgttctg tttgtagagt ctcatagttg gactttctag catatatgtg tccatttcct    4080
tatgctgtaa aagcaagtcc tgcaaccaaa ctcccatcag cccaatccct gatccctgat    4140
cccttccacc tgctctgctg atgaccccc cagcttcact tctgactctt ccccaggaag    4200
ggaagggggg tcagaagaga gggtgagtcc tccagaactc ttcctccaag gacagaaggc    4260
tcctgccccc atagtggcct cgaactcctg gcactaccaa aggacactta tccacgagag    4320
cgcagcatcc gaccaggttg tcactgagaa gatgtttatt ttggtcagtt gggttttat    4380 gtattatact tagtcaaatg taatgtggct tctggaatca ttgtccagag ctgcttcccc    4440
gtcacctggg cgtcatctgg tcctggtaag aggagtgcgt ggcccaccag gcccccctgt    4500
cacccatgac agttcattca gggccgatgg ggcagtcgtg gttgggaaca cagcatttca    4560
agcgtcactt tatttcattc gggccccacc tgcagctccc tcaaagaggc agttgcccag    4620
cctctttccc ttccagttta ttccagagct gccagtgggg cctgaggctc cttagggttt    4680
tctctctatt tcccccttc ttcctcattc cctcgtcttt cccaaaggca tcacgagtca    4740
gtcgcctttc agcaggcagc cttggcggtt tatcgccctg gcaggcaggg gccctgcagc    4800
tctcatgctg cccctgcctt ggggtcaggt tgacaggagg ttggagggaa gccttaagc    4860 tgcaggattc tcaccagctg tgtccggccc agttttgggg tgtgacctca atttcaattt    4920
```

```
tgtctgtact tgaacattat gaagatgggg gcctctttca gtgaatttgt gaacagcaga    4980
attgaccgac agcttccag tacccatggg gctaggtcat taaggccaca tccacagtct    5040
cccccaccct tgttccagtt gttagttact acctcctctc ctgacaatac tgtatgtcgt    5100
cgagctcccc ccaggtctac ccctcccggc cctgcctgct ggtgggcttg tcatagccag    5160
tgggattgcc ggtcttgaca gctcagtgag ctggagatac ttggtcacag ccaggcgcta    5220
gcacagctcc cttctgttga tgctgtattc ccatatcaaa agacacaggg gacacccaga    5280
aacgccacat cccccaatcc atcagtgcca aactagccaa cggccccagc ttctcagctc    5340
gctggatggc ggaagctgct actcgtgagc gccagtgcgg gtgcagacaa tcttctgttg    5400
ggtggcatca ttccaggccc gaagcatgaa cagtgcacct gggacaggga gcagccccaa    5460
attgtcacct gcttctctgc ccagcttttc attgctgtga cagtgatggc gaaagagggt    5520
aataaccaga cacaaactgc caagttgggt ggagaaagga gtttctttag ctgacagaat    5580
ctctgaattt taaatcactt agtaagcggc tcaagcccag gagggagcag agggatacga    5640
gcggagtccc ctgcgcggga ccatctggaa ttggtttagc ccaagtggag cctgacagcc    5700
agaactctgt gtccccccgtc taaccacagc tccttttcca gagcattcca gtcaggctct    5760
ctgggctgac tgggccaggg gaggttacag gtaccagttc tttaagaaga tctttgggca    5820 tatacattt tagcctgtgt cattgcccca aatggattcc tgtttcaagt tcacacctgc    5880
agattctagg acctgtgtcc tagacttcag ggagtcagct gtttctagag ttcctaccat    5940
ggagtgggtc tggaggacct gcccggtggg ggggcagagc cctgctccct ccgggtcttc    6000
ctactcttct ctctgctctg acgggatttg ttgattctct ccattttggt gtctttctct    6060
tttagatatt gtatcaatct ttagaaaagg catagtctac ttgttataaa tcgttaggat    6120
actgcctccc ccagggtcta aaattacata ttagagggga aaagctgaac actgaagtca    6180
gttctcaaca atttagaagg aaaacctaga aaacatttgg cagaaaatta catttcgatg    6240
tttttgaatg aatacgagca agcttttaca acagtgctga tctaaaaata cttagcacctt    6300 ggcctgagat gcctggtgag cattacaggc aaggggaatc tggaggtagc cgacctgagg    6360
acatggcttc tgaacctgtc tttttgggagt ggtatggaag gtggagcgtt caccagtgac    6420
ctggaaggcc cagcaccacc ctccttccca ctcttctcat cttgacagag cctgccccag    6480
cgctgacgtg tcaggaaaac acccagggaa ctaggaaggc acttctgcct gaggggcagc    6540
ctgccttgcc cactcctgct ctgctcgcct cggatcagct gagccttctg agctggcctc    6600
tcactgcctc cccaaggccc cctgcctgcc cgtcaggag gcagaaggaa gcaggtgtga    6660
gggcagtgca aggagggagc acaacccca gctcccgctc cgggctccga cttgtgcaca    6720
ggcagagccc agaccctgga ggaaatccta cctttgaatt caagaacatt tggggaattt    6780
ggaaatctct ttgccccaa accccattc tgtcctacct ttaatcaggt cctgctcagc    6840
agtgagagca gatgaggtga aaaggccaag aggtttggct cctgcccact gatagcccct    6900
ctccccgcag tgtttgtgtg tcaagtggca aagctgttct tcctggtgac cctgattata    6960
tccagtaaca catagactgt gcgcataggc ctgctttgtc tcctctatcc tgggcttttg    7020
ttttgctttt tagttttgct tttagttttt ctgtccctttt tatttaacgc accgactaga    7080
cacacaaagc agttgaattt ttatatatat atctgtatat tgcacaatta taaactcatt    7140
ttgcttgtgg ctccacacac acaaaaaaag acctgttaaa attatacctg ttgcttaatt    7200
acaatatttc tgataaccat agcataggac aagggaaaat aaaaaagaa aaaaagaaa    7260 aaaaaacgac aaatctgtct gctggtcact tcttctgtcc aagcagattc gtggtctttt    7320
```

```
cctcgcttct tcaagggct ttcctgtgcc aggtgaagga ggctccaggc agcacccagg    7380
ttttgcactc ttgtttctcc cgtgcttgtg aaagaggtcc caaggttctg ggtgcaggag    7440
cgctcccttg acctgctgaa gtccggaacg tagtcggcac agcctggtcg ccttccacct    7500
ctgggagctg gagtccactg gggtggcctg actcccccag tcccttccc gtgacctggt    7560 cagggtgagc ccatgtggag tcagcctcgc aggcctccct gccagtaggg tccgagtgtg    7620
tttcatcctt cccactctgt cgagcctggg ggctggagcg gagacgggag gcctggcctg    7680
tctcggaacc tgtgagctgc accaggtaga acgccaggga ccccagaatc atgtgcgtca    7740
gtccaagggg tcccctccag gagtagtgaa gactccagaa atgtcccttt cttctccccc    7800
atcctacgag taattgcatt tgcttttgta attcttaatg agcaatatct gctagagagt    7860
ttagctgtaa cagttctttt tgatcatctt tttttaataa ttagaaacac caaaaaaatc    7920
cagaaacttg ttcttccaaa gcagagagca ttataatcac cagggccaaa gcttccctc    7980 cctgctgtca ttgcttcttc tgaggcctga atccaaaaga aaacagcca taggcccttt    8040 cagtggccgg gctacccgtg agcccttcgg aggaccaggg ctggggcagc tctgggccc    8100 acatccgggg ccagctccgg cgtgtgttca gtgttagcag tgggtcatga tgctcttcc    8160 cacccagcct gggatagggg cagaggaggc gaggaggccg ttgccgctga tgtttggccg    8220
tgaacaggtg ggtgtctgcg tgcgtccacg tgcgtgtttt ctgactgaca tgaaatcgac    8280
gcccgagtta gcctcacccg gtgacctcta gccctgcccg gatggagcgg ggcccacccg    8340
gttcagtgtt tctggggagc tggacagtgg agtgcaaaag gcttcagaa cttgaagcct    8400 gctccttccc ttgctaccac ggcctccttt ccgtttgatt tgtcactgct tcaatcaata    8460
acagccgctc cagagtcagt agtcaatgaa tatatgacca aatatcacca ggactgttac    8520
tcaatgtgtg ccgagcccct gcccatgctg ggctcccgtg tatctggaca ctgtaacgtg    8580
tgctgtgttt gctccccttc cccttccttc tttgcccttt acttgtcttt ctggggtttt    8640
tctgtttggg tttggtttgg tttttatttc tccttttgtg ttccaaacat gaggttctct    8700
ctactggtcc tcttaactgt ggtgttgagg cttatatttg tgtaattttt ggtgggtgaa    8760
aggaattttg ctaagtaaat ctcttctgtg tttgaactga agtctgtatt gtaactatgt    8820
ttaaagtaat tgttccagag acaaatattt ctagacactt tttctttaca aacaaaagca    8880
ttcggaggga gggggatggt gactgagatg agagggagaa gctgaacaga tgaccctgc    8940 ccagatcagc cagaagccac ccaaagcagt ggagcccagg agtcccactc caagccagca    9000
agccgaatag ctgatgtgtt gccactttcc aagtcactgc aaaaccaggt tttgttccgc    9060
ccagtggatt cttgttttgc ttcccctccc ccgagatta ttaccaccat cccgtgcttt    9120
taaggaaagg caagattgat gtttccttga ggggagccag gaggggatgt gtgtgtgcag    9180
agctgaagag ctggggagaa tggggctggg cccacccaag caggaggctg ggacgctctg    9240
ctgtgggcac aggtcaggct aatgttggca gatgcagctc ttcctggaca ggccaggtgg    9300
tgggcattct ctctccaagg tgtgcccgt gggcattact gtttaagaca cttccgtcac    9360
atcccacccc atcctccagg gctcaacact gtgacatctc tattcccac cctccccttc    9420 ccagggcaat aaaatgacca tggagggggc ttgcactctg ttggctgtca cccgatcgcc    9480
agcaaaactt agatgtgaga aaaccccttc ccattccatg gcgaaaacat ctccttagaa    9540
aagccattac cctcattagg catggttttg ggctcccaaa acacctgaca gcccctccct    9600
cctctgagag gcggagagtg ctgactgtag tgaccattgc atgccgggtg cagcatctgg    9660
```

| | |
|---|---:|
| aagagctagg cagggtgtct gccccctcct gagttgaagt catgctcccc tgtgccagcc | 9720 |
| cagaggccga gagctatgga cagcattgcc agtaacacag ccaccctgt gcagaaggga | 9780 |
| gctggctcca gcctggaaac ctgtctgagg ttgggagagg tgcacttggg gcacagggag | 9840 |
| aggccgggac acacttagct ggagatgtct ctaaaagccc tgtatcgtat tcaccttcag | 9900 |
| tttttgtgtt ttgggacaat tactttagaa aataagtagg tcgttttaaa aacaaaaatt | 9960 |
| attgattgct tttttgtagt gttcagaaaa aaggttcttt tgtatagcc aaatgactga | 10020 |
| aagcactgat atatttaaaa acaaaaggca atttattaag gaaatttgta ccatttcagt | 10080 |
| aaacctgtct gaatgtacct gtatacgttt caaaaacacc cccccccac tgaatccctg | 10140 |
| taacctattt attatataaa gagtttgcct tataaattt | 10179 |

<210> SEQ ID NO 27
<211> LENGTH: 10185
<212> TYPE: DNA
<213> ORGANISM: Homo sapiens

<400> SEQUENCE: 27

| | |
|---|---:|
| ccggaaaatg gccgccgccg ccgccgccgc gccgagcgga ggaggaggag gaggaggcga | 60 |
| ggaggagaga ctgctccata aaatacaga ctcaccagtt cctgctttga tgtgacatgt | 120 |
| gactccccag aatacacctt gcttctgtag accagctcca acaggattcc atggtagctg | 180 |
| ggatgttagg gctcagggaa gaaaagtcag aagaccagga cctccagggc ctcaaggaca | 240 |
| aacccctcaa gtttaaaaag gtgaagaaag ataagaaaga agagaaagag ggcaagcatg | 300 |
| agcccgtgca gccatcagcc caccactctg ctgagcccgc agaggcaggc aaagcagaga | 360 |
| catcagaagg gtcaggctcc gccccggctg tgccggaagc ttctgcctcc cccaaacagc | 420 |
| ggcgctccat catccgtgac cggggaccca tgtatgatga ccccaccctg cctgaaggct | 480 |
| ggacacggaa gcttaagcaa aggaaatctg gccgctctgc tgggaagtat gatgtgtatt | 540 |
| tgatcaatcc ccagggaaaa gcctttcgct ctaaagtgga gttgattgcg tacttcgaaa | 600 |
| aggtaggcga cacatccctg gaccctaatg attttgactt cacggtaact gggagaggga | 660 |
| gcccctcccg gcgagagcag aaaccaccta agaagcccaa atctcccaaa gctccaggaa | 720 |
| ctggcagagg ccggggacgc cccaaaggga gcggcaccac gagacccaag gcggccacgt | 780 |
| cagagggtgt gcaggtgaaa agggtcctgg agaaaagtcc tgggaagctc cttgtcaaga | 840 |
| tgccttttca aacttcgcca gggggcaagg ctgagggggg tggggccacc acatccaccc | 900 |
| aggtcatggt gatcaaacgc cccggcagga agcgaaaagc tgaggccgac cctcaggcca | 960 |
| ttcccaagaa acgggccga aagccgggga gtgtggtggc agccgctgcc gccgaggcca | 1020 |
| aaaagaaagc cgtgaaggag tcttctatcc gatctgtgca ggagaccgta ctccccatca | 1080 |
| agaagcgcaa gacccgggag acggtcagca tcgaggtcaa ggaagtggtg aagcccctgc | 1140 |
| tggtgtccac cctcggtgag aagagcggga aaggactgaa gacctgtaag agccctgggc | 1200 |
| ggaaaagcaa ggagagcagc cccaagggc gcagcagcag cgcctcctca ccccccaaga | 1260 |
| aggagcacca ccaccatcac caccactcag agtccccaaa ggccccgtg ccactgctcc | 1320 |
| caccctgcc cccacctcca cctgagcccg agagctccga ggaccccacc agccccctg | 1380 |
| agccccagga cttgagcagc agcgtctgca aagaggagaa gatgcccaga ggaggctcac | 1440 |
| tggagagcga cggctgcccc aaggagccag ctaagactca gcccgcggtt gccaccgccg | 1500 |
| ccacggccga agaaagtac aaacaccgag ggagggaga gcgcaaagac attgtttcat | 1560 |
| cctccatgcc aaggccaaac agagaggagc ctgtggacag ccggacgccc gtgaccgaga | 1620 |

```
gagttagctg actttacacg gagcggattg caaagcaaac caacaagaat aaaggcagct    1680
gttgtctctt ctccttatgg gtagggctct gacaaagctt cccgattaac tgaaataaaa    1740 aatattttt ttctttcag taaacttaga gtttcgtggc ttcagggtgg gagtagttgg     1800
agcattgggg atgttttct taccgacaag cacagtcagg ttgaagacct aaccagggcc    1860
agaagtagct ttgcactttt ctaaactagg ctccttcaac aaggcttgct gcagatacta    1920
ctgaccagac aagctgttga ccaggcacct ccctcccgc ccaaacctt ccccatgtg     1980 gtcgttagag acagagcgac agagcagttg agaggacact cccgttttcg gtgccatcag    2040
tgccccgtct acagctcccc cagctcccc caccctcccc actcccaacc acgttgggac    2100
agggaggtgt gaggcaggag agacagttgg attctttaga gaagatggat atgaccagtg    2160
gctatggcct gtgcgatccc acccgtggtg gctcaagtct ggccccacac cagccccaat    2220
ccaaaactgg caaggacgct tcacaggaca ggaaagtggc acctgtctgc tccagctctg    2280
gcatggctag gaggggggag tcccttgaac tactgggtgt agactggcct gaaccacagg    2340
agaggatggc ccagggtgag gtggcatggt ccattctcaa gggacgtcct ccaacgggtg    2400
gcgctagagg ccatggaggc agtaggacaa ggtgcaggca ggctggcctg ggtcaggcc    2460 gggcagagca cagcggggtg agagggattc ctaatcactc agagcagtct gtgacttagt    2520
ggacagggga gggggcaaag ggggaggaga agaaaatgtt cttccagtta ctttccaatt    2580
ctcctttagg gacagcttag aattatttgc actattgagt cttcatgttc ccacttcaaa    2640
acaaacagat gctctgagag caaactggct tgaattggtg acatttagtc cctcaagcca    2700
ccagatgtga cagtgttgag aactacctgg atttgtatat atacctgcgc ttgttttaaa    2760
gtgggctcag cacatagggt tcccacgaag ctccgaaact ctaagtgttt gctgcaattt    2820
tataaggact tcctgattgg tttctcttct cccttccat ttctgccttt tgttcatttc     2880
atcctttcac ttctttccct tcctccgtcc tcctccttcc tagttcatcc cttctcttcc    2940
aggcagccgc ggtgcccaac cacacttgtc ggctccagtc cccagaactc tgcctgccct    3000
ttgtcctcct gctgccagta ccagccccac cctgttttga gccctgagga ggccttgggc    3060
tctgctgagt ccgacctggc ctgtctgtga agagcaagag agcagcaagg tcttgctctc    3120
ctaggtagcc ccctcttccc tggtaagaaa aagcaaaagg catttcccac cctgaacaac    3180
gagccttttc accttctac tctagagaag tggactggag gagctgggcc cgatttggta    3240
gttgaggaaa gcacagaggc ctcctgtggc ctgccagtca tcgagtggcc caacagggc    3300 tccatgccca ccgaccttga cctcactcag aagtccagag tctagcgtag tgcagcaggg    3360
cagtagcggt accaatgcag aactcccaag acccgagctg ggaccagtac ctgggtcccc    3420
agcccttcct ctgctccccc ttttccctcg gagttcttct tgaatggcaa tgttttgctt    3480
ttgctcgatg cagacagggg gccagaacac cacacattc actgtctgtc tggtccatag    3540
ctgtggtgta ggggcttaga ggcatgggct tgctgtgggt ttttaattga tcagtttca    3600 tgtgggatcc catcttttta acctctgttc aggaagtcct tatctagctg catatcttca    3660
tcatattggt atatcctttt ctgtgtttac agagatgtct cttatatcta aatctgtcca    3720
actgagaagt accttatcaa agtagcaaat gagacagcag tcttatgctt ccagaaacac    3780
ccacaggcat gtcccatgtg agctgctgcc atgaactgtc aagtgtgtgt tgtcttgtgt    3840
atttcagtta ttgtccctgg cttccttact atggtgtaat catgaaggag tgaaacatca    3900
tagaaactgt ctagcacttc cttgccagtc tttagtgatc aggaaccata gttgacagtt    3960
```

```
ccaatcagta gcttaagaaa aaaccgtgtt tgtctcttct ggaatggtta gaagtgaggg      4020
agtttgcccc gttctgtttg tagagtctca tagttggact ttctagcata tatgtgtcca      4080
tttccttatg ctgtaaaagc aagtcctgca accaaactcc catcagccca atccctgatc      4140
cctgatccct tccacctgct ctgctgatga ccccccagc ttcacttctg actcttcccc       4200
aggaagggaa gggggtcag aagagaggt gagtcctcca gaactcttcc tccaaggaca        4260
gaaggctcct gccccatag tggcctcgaa ctcctggcac taccaaagga cacttatcca       4320
cgagagcgca gcatccgacc aggttgtcac tgagaagatg tttattttgg tcagttgggt     4380
ttttatgtat tatacttagt caaatgtaat gtggcttctg gaatcattgt ccagagctgc     4440
ttccccgtca cctgggcgtc atctggtcct ggtaagagga gtgcgtggcc caccaggccc     4500
ccctgtcacc catgacagtt cattcagggc cgatggggca gtcgtggttg gaacacagc      4560
atttcaagcg tcactttatt tcattcgggc cccacctgca gctccctcaa agaggcagtt     4620
gcccagcctc tttcccttcc agtttattc agagctgcca gtggggcctg aggctcctta      4680
gggttttctc tctatttccc cctttcttcc tcattccctc gtctttccca aaggcatcac     4740
gagtcagtcg cctttcagca ggcagccttg gcggtttatc gccctggcag gcaggggccc    4800
tgcagctctc atgctgcccc tgccttgggg tcaggttgac aggaggttgg agggaaagcc    4860
ttaagctgca ggattctcac cagctgtgtc cggcccagtt ttggggtgtg acctcaattt   4920
caattttgtc tgtacttgaa cattatgaag atgggggcct ctttcagtga atttgtgaac   4980
agcagaattg accgacagct ttccagtacc catgggcta ggtcattaag gccacatcca    5040
cagtctcccc cacccttgtt ccagttgtta gttactacct cctctcctga caatactgta   5100
tgtcgtcgag ctccccccag gtctacccct cccggccctg cctgctggtg ggcttgtcat   5160
agccagtggg attgccggtc ttgacagctc agtgagctgg agatacttgg tcacagccag   5220
gcgctagcac agctcccttc tgttgatgct gtattcccat atcaaaagac cagggggaca   5280
cccagaaacg ccacatcccc caatccatca gtgccaaact agccaacggc cccagcttct   5340
cagctcgctg gatggcggaa gctgctactc gtgagcgcca gtgcgggtgc agacaatctt   5400
ctgttgggtg gcatcattcc aggcccgaag catgaacagt gcacctggga cagggagcag   5460
ccccaaattg tcacctgctt ctctgcccag ctttcattg ctgtgacagt gatggcgaaa    5520
gagggtaata accagacaca aactgccaag ttgggtggag aaaggagtt ctttagctga    5580
cagaatctct gaattttaaa tcacttagta agcggctcaa gcccaggagg gagcagaggg   5640
atacgagcgg agtcccctgc gcgggaccat ctggaattgg tttagcccaa gtggagcctg   5700
acagccagaa ctctgtgtcc cccgtctaac cacagctcct tttccagagc attccagtca   5760
ggctctctgg gctgactggg ccaggggagg ttacaggtac cagttcttta agaagatctt   5820
tgggcatata cattttagc ctgtgtcatt gccccaaatg gattcctgtt tcaagttcac   5880
acctgcagat tctaggacct gtgtcctaga cttcagggag tcagctgttt ctagagttcc   5940
taccatggag tgggtctgga ggacctgccc ggtggggggg cagagccctg ctccctccgg   6000
gtcttcctac tcttctctct gctctgacgg gatttgttga ttctctccat tttggtgtct   6060
ttctcttttta gatattgtat caatctttag aaaaggcata gtctacttgt tataaatcgt   6120
taggatactg cctcccccag ggtctaaaat tacatattag aggggaaag ctgaacactg    6180
aagtcagttc tcaacaattt agaaggaaaa cctagaaaac atttggcaga aaattacatt   6240
tcgatgtttt tgaatgaata cgagcaagct tttacaacag tgctgatcta aaaatactta   6300
gcacttggcc tgagatgcct ggtgagcatt acaggcaagg ggaatctgga ggtagccgac   6360
```

```
ctgaggacat ggcttctgaa cctgtctttt gggagtggta tggaaggtgg agcgttcacc    6420
agtgacctgg aaggcccagc accaccctcc ttcccactct tctcatcttg acagagcctg    6480
ccccagcgct gacgtgtcag gaaaacaccc agggaactag gaaggcactt ctgcctgagg    6540
ggcagcctgc cttgcccact cctgctctgc tcgcctcgga tcagctgagc cttctgagct    6600
ggcctctcac tgcctcccca aggcccctg cctgccctgt caggaggcag aaggaagcag     6660
gtgtgagggc agtgcaagga gggagcacaa cccccagctc ccgctccggg ctccgacttg    6720
tgcacaggca gagcccagac cctggaggaa atcctacctt tgaattcaag aacatttggg    6780
gaatttggaa atctctttgc ccccaaaccc ccattctgtc ctacctttaa tcaggtcctg    6840
ctcagcagtg agagcagatg aggtgaaaag gccaagaggt ttggctcctg cccactgata    6900
gcccctctcc ccgcagtgtt tgtgtgtcaa gtggcaaagc tgttcttcct ggtgaccctg    6960
attatatcca gtaacacata gactgtgcgc ataggcctgc tttgtctcct ctatcctggg    7020
cttttgtttt gctttttagt tttgctttta gttttctgt cccttttatt taacgcaccg     7080
actagacaca caaagcagtt gaattttat atatatatct gtatattgca caattataaa     7140
ctcattttgc ttgtggctcc acacacacaa aaaagacct gttaaaatta tacctgttgc     7200
ttaattacaa tatttctgat aaccatagca taggacaagg gaaaataaaa aagaaaaaa    7260 aagaaaaaaa aacgacaaat ctgtctgctg gtcacttctt ctgtccaagc agattcgtgg    7320
tcttttcctc gcttctttca agggctttcc tgtgccaggt gaaggaggct ccaggcagca    7380
cccaggtttt gcactcttgt ttctcccgtg cttgtgaaag aggtcccaag gttctgggtg    7440
caggagcgct cccttgacct gctgaagtcc ggaacgtagt cggcacagcc tggtcgcctt    7500
ccacctctgg gagctggagt ccactggggt ggcctgactc ccccagtccc cttcccgtga    7560
cctggtcagg gtgagcccat gtggagtcag cctcgcaggc ctccctgcca gtagggtccg    7620
agtgtgtttc atccttccca ctctgtcgag cctgggggct ggagcggaga cgggaggcct    7680
ggcctgtctc ggaacctgtg agctgcacca ggtagaacgc cagggacccc agaatcatgt    7740
gcgtcagtcc aagggtccc ctccaggagt agtgaagact ccagaaatgt cccttctttc     7800
tcccccatcc tacgagtaat tgcatttgct tttgtaattc ttaatgagca atatctgcta    7860
gagagtttag ctgtaacagt tcttttgat catctttttt taataattag aaacaccaaa     7920
aaaatccaga aacttgttct tccaaagcag agagcattat aatcaccagg ccaaaagct     7980 tccctccctg ctgtcattgc ttcttctgag gcctgaatcc aaaagaaaaa cagccatagg    8040
ccctttcagt ggccgggcta cccgtgagcc cttcggagga ccagggctgg ggcagcctct    8100
gggcccacat ccggggccag ctccggcgtg tgttcagtgt tagcagtggg tcatgatgct    8160 cttttcccacc cagcctggga taggggcaga ggaggcgagg aggccgttgc cgctgatgtt    8220
tggccgtgaa caggtgggtg tctgcgtgcg tccacgtgcg tgttttctga ctgacatgaa    8280
atcgacgccc gagttagcct cacccggtga cctctagccc tgcccggatg gagcggggcc    8340 caccccggttc agtgtttctg gggagctgga cagtggagtg caaaaggctt gcagaacttg    8400
aagcctgctc cttcccttgc taccacggcc tcctttccgt ttgatttgtc actgcttcaa    8460
tcaataacag ccgctccaga gtcagtagtc aatgaatata tgaccaaata tcaccaggac    8520
tgttactcaa tgtgtgccga gcccttgccc atgctgggct ccgtgtatc tggacactgt     8580 aacgtgtgct gtgtttgctc cccttcccct tccttctttg cccttacttt gtctttctgg    8640 ggttttctg tttgggtttg gtttggtttt tatttctcct tttgtgttcc aaacatgagg     8700
```

| | | | | |
|---|---|---|---|---|
| ttctctctac | tggtcctctt | aactgtggtg | ttgaggctta | tatttgtgta aatttttggtg | 8760 |
| ggtgaaagga | attttgctaa | gtaaatctct | tctgtgtttg | aactgaagtc tgtattgtaa | 8820 |
| ctatgtttaa | agtaattgtt | ccagagacaa | atatttctag | acacttttc tttacaaaca | 8880 |
| aaagcattcg | gagggagggg | gatggtgact | gagatgagag | gggagagctg aacagatgac | 8940 |
| ccctgcccag | atcagccaga | agccacccaa | agcagtggag | cccaggagtc ccactccaag | 9000 |
| ccagcaagcc | gaatagctga | tgtgttgcca | ctttccaagt | cactgcaaaa ccaggttttg | 9060 |
| ttccgcccag | tggattcttg | ttttgcttcc | cctcccccg | agattattac caccatcccg | 9120 |
| tgcttttaag | gaaaggcaag | attgatgttt | ccttgagggg | agccaggagg ggatgtgtgt | 9180 |
| gtgcagagct | gaagagctgg | ggagaatggg | gctgggccca | cccaagcagg aggctgggac | 9240 |
| gctctgctgt | gggcacaggt | caggctaatg | ttggcagatg | cagctcttcc tggacaggcc | 9300 |
| aggtggtggg | cattctctct | ccaaggtgtg | ccccgtgggc | attactgttt aagacacttc | 9360 |
| cgtcacatcc | cacccatcc | tccagggctc | aacactgtga | catctctatt ccccaccctc | 9420 |
| cccttcccag | ggcaataaaa | tgaccatgga | ggggcttgc | actctcttgg ctgtcacccg | 9480 |
| atcgccagca | aaacttagat | gtgagaaaac | cccttcccat | tccatggcga aaacatctcc | 9540 |
| ttagaaaagc | cattaccctc | attaggcatg | gttttgggct | cccaaaacac ctgacagccc | 9600 |
| ctccctcctc | tgagaggcgg | agagtgctga | ctgtagtgac | cattgcatgc cgggtgcagc | 9660 |
| atctggaaga | gctaggcagg | gtgtctgccc | cctcctgagt | tgaagtcatg ctcccctgtg | 9720 |
| ccagcccaga | ggccgagagc | tatggacagc | attgccagta | acacaggcca ccctgtgcag | 9780 |
| aagggagctg | gctccagcct | ggaaacctgt | ctgaggttgg | gagaggtgca cttggggcac | 9840 |
| agggagaggc | cgggacacac | ttagctggag | atgtctctaa | aagccctgta tcgtattcac | 9900 |
| cttcagtttt | tgtgttttgg | gacaattact | ttagaaaata | agtaggtcgt tttaaaaaca | 9960 |
| aaaattattg | attgcttttt | tgtagtgttc | agaaaaaagg | ttctttgtgt atagccaaat | 10020 |
| gactgaaagc | actgatatat | ttaaaaacaa | aaggcaattt | attaaggaaa tttgtaccat | 10080 |
| ttcagtaaac | ctgtctgaat | gtacctgtat | acgtttcaaa | aacacccccc ccccactgaa | 10140 |
| tccctgtaac | ctatttatta | tataaagagt | ttgccttata | aattt | 10185 |

<210> SEQ ID NO 28
<211> LENGTH: 10227
<212> TYPE: DNA
<213> ORGANISM: Homo sapiens

<400> SEQUENCE: 28

| | | | | |
|---|---|---|---|---|
| gggcgcgcgc | tccctcctct | cggagagagg | gctgtggtaa | aagccgtccg gaaaatgcgc | 60 |
| cgccgccgcc | gccgcgccga | gcggaggagg | aggaggaggc | gaggaggaga gactgctcca | 120 |
| taaaataca | gactcaccag | ttcctgcttt | gatgtgacat | gtgactcccc agaatacacc | 180 |
| ttgcttctgt | agaccagctc | caacaggatt | ccatggtagc | tgggatgtta gggctcaggg | 240 |
| aagaaaagtc | agaagaccag | gacctccagg | gcctcaagga | caaacccctc aagtttaaaa | 300 |
| aggtgaagaa | agataagaaa | gaagagaaag | agggcaagca | tgagcccgtg cagccatcag | 360 |
| cccaccactc | tgctgagccc | gcagaggcag | gcaaagcaga | gacatcagaa gggtcaggct | 420 |
| ccgccccggc | tgtgccggaa | gcttctgcct | ccccaaaca | gcggcgctcc atcatccgtg | 480 |
| accggggacc | catgtatgat | gaccccaccc | tgcctgaagg | ctggacacgg aagcttaagc | 540 |
| aaaggaaatc | tggccgctct | gctgggaagt | atgatgtgta | tttgatcaat ccccagggaa | 600 |
| aagcctttcg | ctctaaagtg | gagttgattg | cgtacttcga | aaaggtaggc gacacatccc | 660 |

```
tggaccctaa tgattttgac ttcacggtaa ctgggagagg gagcccctcc cggcgagagc    720
agaaaccacc taagaagccc aaatctccca aagctccagg aactggcaga ggccgggggac   780
gccccaaagg gagcggcacc acgagaccca aggcggccac gtcagagggt gtgcaggtga    840
aaagggtcct ggagaaaagt cctgggaagc tccttgtcaa gatgccttt  caaacttcgc    900
caggggcaa  ggctgagggg ggtggggcca ccacatccac ccaggtcatg gtgatcaaac    960
gccccggcag gaagcgaaaa gctgaggccg accctcaggc cattcccaag aaacggggcc   1020
gaaagccggg gagtgtggtg gcagccgctg ccgccgaggc caaaaagaaa gccgtgaagg   1080
agtcttctat ccgatctgtg caggagaccg tactccccat caagaagcgc aagacccggg   1140
agacggtcag catcgaggtc aaggaagtgg tgaagcccct gctggtgtcc accctcggtg   1200
agaagagcgg gaaaggactg aagacctgta agagccctgg gcggaaaagc aaggagagca   1260
gccccaaggg gcgcagcagc agcgcctcct caccccccaa gaaggagcac caccaccatc   1320
accaccactc agagtcccca aaggcccccg tgccactgct cccacccctg ccccaccctc   1380
cacctgagcc cgagagctcc gaggacccca ccagcccccc tgagcccag  gacttgagca   1440
gcagcgtctg caaagaggag aagatgccca gaggaggctc actggagagc gacggctgcc   1500
ccaaggagcc agctaagact cagcccgcgg ttgccaccgc cgccacggcc gcagaaaagt   1560
acaaacaccg aggggaggga gagcgcaaag acattgtttc atcctccatg ccaaggccaa   1620
acagagagga gcctgtggac agccggacgc ccgtgaccga gagagttagc tgactttaca   1680
cggagcggat tgcaaagcaa accaacaaga ataaaggcag ctgttgtctc ttctccttat   1740
gggtagggct ctgacaaagc ttcccgatta actgaaataa aaaatatttt tttttctttc   1800
agtaaactta gagtttcgtg gcttcagggt gggagtagtt ggagcattgg ggatgttttt   1860
cttaccgaca agcacagtca ggttgaagac ctaaccaggg ccagaagtag cttgcactt    1920
ttctaaacta ggctccttca acaaggcttg ctgcagatac tactgaccag acaagctgtt   1980
gaccaggcac ctcccctccc gcccaaacct ttccccccatg tggtcgttag agacagagcg   2040
acagagcagt tgagaggaca ctcccgtttt cggtgccatc agtgcccgt  ctacagctcc   2100
cccagctccc cccacctccc ccactcccaa ccacgttggg acaggaggt  gtgaggcagg   2160
agagacagtt ggattcttta gagaagatgg atatgaccag tggctatggc ctgtgcgatc   2220
ccacccgtgg tggctcaagt ctggcccac  accagcccca atccaaaact ggcaaggacg   2280
cttcacagga caggaaagtg gcacctgtct gctccagctc tggcatggct aggagggggg   2340
agtcccttga actactgggt gtagactggc ctgaaccaca ggagaggatg gcccagggtg   2400
aggtggcatg gtccattctc aagggacgtc ctccaacggg tggcgctaga ggccatggag   2460
gcagtaggac aaggtgcagg caggctgcc  tggggtcagg ccgggcagag cacagcgggg   2520
tgagagggat tcctaatcac tcagagcagt ctgtgactta gtggacaggg gagggggcaa   2580
aggggggagga gaagaaaatg ttcttccagt tactttccaa ttctccttta gggacagctt   2640
agaattattt gcactattga gtcttcatgt tcccacttca aaacaaacag atgctctgag   2700
agcaaactgg cttgaattgg tgacatttag tccctcaagc caccagatgt gacagtgttg   2760
agaactacct ggatttgtat atatacctgc gcttgtttta aagtgggctc agcacatagg   2820
gttcccacga agctccgaaa ctctaagtgt ttgctgcaat tttataagga cttcctgatt   2880
ggtttctctt ctcccctttcc atttctgcct tttgttcatt tcatcctttc acttcttttcc  2940
cttcctccgt cctcctcctt cctagttcat cccttctctt ccaggcagcc gcggtgccca   3000
```

```
accacacttg tcggctccag tccccagaac tctgcctgcc ctttgtcctc ctgctgccag    3060
taccagcccc accctgtttt gagccctgag gaggccttgg gctctgctga gtccgacctg    3120
gcctgtctgt gaagagcaag agagcagcaa ggtcttgctc tcctaggtag ccccctcttc    3180
cctggtaaga aaaagcaaaa ggcatttccc accctgaaca acgagccttt tcacccttct    3240
actctagaga agtggactgg aggagctggg cccgatttgg tagttgagga aagcacagag    3300
gcctcctgtg gcctgccagt catcgagtgg cccaacaggg gctccatgcc agccgacctt    3360
gacctcactc agaagtccag agtctagcgt agtgcagcag ggcagtagcg gtaccaatgc    3420
agaactccca agacccgagc tgggaccagt acctgggtcc ccagcccttc ctctgctccc    3480
ccttttccct cggagttctt cttgaatggc aatgttttgc ttttgctcga tgcagacagg    3540
gggccagaac accacacatt tcactgtctg tctggtccat agctgtggtg tagggggctta   3600 gaggcatggg cttgctgtgg gttttaatt gatcagtttt catgtgggat cccatctttt    3660
taacctctgt tcaggaagtc cttatctagc tgcatatctt catcatattg gtatatcctt    3720
ttctgtgttt acagagatgt ctcttatatc taaatctgtc caactgagaa gtaccttatc    3780
aaagtagcaa atgagacagc agtcttatgc ttccagaaac acccacaggc atgtcccatg    3840
tgagctgctg ccatgaactg tcaagtgtgt gttgtcttgt gtatttcagt tattgtccct    3900
ggcttcctta ctatggtgta atcatgaagg agtgaaacat catagaaact gtctagcact    3960
tccttgccag tctttagtga tcaggaacca tagttgacag ttccaatcag tagcttaaga    4020
aaaaaccgtg tttgtctctt ctggaatggt tagaagtgag ggagtttgcc ccgttctgtt    4080
tgtagagtct catagttgga ctttctagca tatatgtgtc catttcctta tgctgtaaaa    4140
gcaagtcctg caaccaaact cccatcagcc caatccctga tccctgatcc cttccacctg    4200
ctctgctgat gacccccca gcttcacttc tgactcttcc ccaggaaggg aaggggggtc    4260
agaagagagg gtgagtcctc cagaactctt cctccaagga cagaaggctc ctgccccat    4320 agtggcctcg aactcctggc actaccaaag gacacttatc cacgagagcg cagcatccga    4380
ccaggttgtc actgagaaga tgttttatttt ggtcagttgg gttttatgt attatactta    4440 gtcaaatgta atgtggcttc tggaatcatt gtccagagct gcttcccgt cacctgggcg    4500 tcatctggtc ctggtaagag gagtgcgtgg cccaccaggc ccccctgtca cccatgacag    4560
ttcattcagg gccgatgggg cagtcgtggt tgggaacaca gcatttcaag cgtcacttta    4620
tttcattcgg gccccacctg cagctccctc aaagaggcag ttgcccagcc tctttccctt    4680
ccagtttatt ccagagctgc cagtgggcc tgaggctcct tagggttttc tctctatttc    4740
cccctttctt cctcattccc tcgtctttcc caaaggcatc acgagtcagt cgcctttcag    4800
caggcagcct tggcggttta tcgccctggc aggcaggggc cctgcagctc tcatgctgcc    4860
cctgccttgg ggtcaggttg acaggaggtt ggagggaaag ccttaagctg caggattctc    4920
accagctgtg tccggcccag ttttggggtg tgacctcaat ttcaattttg tctgtacttg    4980
aacattatga agatgggggc ctctttcagt gaatttgtga acagcagaat tgaccgacag    5040
ctttccagta cccatggggc taggtcatta aggccacatc cacagtctcc cccacccttg    5100
ttccagttgt tagttactac ctcctctcct gacaatactg tatgtcgtcg agctccccc    5160 aggtctaccc ctcccggccc tgcctgctgg tgggcttgtc atagccagtg ggattgccgg    5220
tcttgacagc tcagtgagct ggagatactt ggtcacagcc aggcgctagc acagctccct    5280
tctgttgatg ctgtattccc atatcaaaag acacaggggga cacccagaaa cgccacatcc    5340
cccaatccat cagtgccaaa ctagccaacg gccccagctt ctcagctcgc tggatggcgg    5400
```

```
aagctgctac tcgtgagcgc cagtgcgggt gcagacaatc ttctgttggg tggcatcatt    5460
ccaggcccga agcatgaaca gtgcacctgg gacagggagc agccccaaat tgtcacctgc    5520
ttctctgccc agcttttcat tgctgtgaca gtgatggcga agagggtaa taaccagaca     5580 caaactgcca agttgggtgg agaaaggagt ttctttagct gacagaatct ctgaattta     5640 aatcacttag taagcggctc aagcccagga gggagcagag ggatacgagc ggagtcccct    5700
gcgcgggacc atctggaatt ggtttagccc aagtggagcc tgacagccag aactctgtgt    5760
cccccgtcta accacagctc cttttccaga gcattccagt caggctctct gggctgactg    5820
ggccagggga ggttacaggt accagttctt taagaagatc tttgggcata tacatttta    5880 gcctgtgtca ttgccccaaa tggattcctg tttcaagttc acacctgcag attctaggac    5940
ctgtgtccta gacttcaggg agtcagctgt ttctagagtt cctaccatgg agtgggtctg    6000
gaggacctgc ccggtggggg ggcagagccc tgctccctcc gggtcttcct actcttctct    6060
ctgctctgac gggatttgtt gattctctcc attttggtgt cttctctttt tagatattgt    6120
atcaatcttt agaaaaggca tagtctactt gttataaatc gttaggatac tgcctcccc     6180 agggtctaaa attacatatt agagggaaa agctgaacac tgaagtcagt tctcaacaat    6240
ttagaaggaa aacctagaaa acatttggca gaaaattaca tttcgatgtt tttgaatgaa    6300
tacgagcaag cttttacaac agtgctgatc taaaaatact tagcacttgg cctgagatgc    6360
ctggtgagca ttacaggcaa ggggaatctg gaggtagccg acctgaggac atggcttctg    6420
aacctgtctt ttgggagtgg tatggaaggt ggagcgttca ccagtgacct ggaaggccca    6480
gcaccaccct ccttcccact cttctcatct tgacagagcc tgccccagcg ctgacgtgtc    6540
aggaaaacac ccagggaact aggaaggcac ttctgcctga ggggcagcct gccttgccca    6600
ctcctgctct gctcgcctcg gatcagctga gccttctgag ctggcctctc actgcctccc    6660
caaggccccc tgcctgccct gtcaggaggc agaaggaagc aggtgtgagg gcagtgcaag    6720
gagggagcac aaccccccagc tcccgctccg ggctccgact tgtgcacagg cagagcccag    6780
accctggagg aaatcctacc tttgaattca agaacatttg gggaatttgg aaatctcttt    6840
gcccccaaac ccccattctg tcctaccttt aatcaggtcc tgctcagcag tgagagcaga    6900
tgaggtgaaa aggccaagag gtttggctcc tgcccactga tagcccctct ccccgcagtg    6960
tttgtgtgtc aagtggcaaa gctgttcttc ctggtgaccc tgattatatc cagtaacaca    7020
tagactgtgc gcataggcct gctttgtctc ctctatcctg ggcttttgtt ttgctttta    7080 gttttgcttt tagttttct gtcccttta tttaacgcac cgactagaca cacaaagcag    7140
ttgaattttt atatatatat ctgtatattg cacaattata aactcatttt gcttgtggct    7200
ccacacacac aaaaaaagac ctgttaaaat tatacctgtt gcttaattac aatatttctg    7260
ataaccatag cataggacaa gggaaaataa aaaagaaaa aaaagaaaaa aaaacgacaa    7320
atctgtctgc tggtcacttc ttctgtccaa gcagattcgt ggtctttcc tcgcttcttt    7380 caagggcttt cctgtgccag gtgaaggagg ctccaggcag cacccaggtt ttgcactctt    7440
gtttctcccg tgcttgtgaa agaggtccca aggttctggg tgcaggagcg ctcccttgac    7500
ctgctgaagt ccggaacgta gtcggcacag cctggtcgcc ttccacctct gggagctgga    7560
gtccactggg gtggcctgac tcccccagtc cccttcccgt gacctggtca gggtgagccc    7620
atgtggagtc agcctcgcag gcctccctgc cagtagggtc cgagtgtgtt tcatccttcc    7680
cactctgtcg agcctggggg ctggagcgga gacgggaggc ctggcctgtc tcggaacctg    7740
```

```
tgagctgcac caggtagaac gccagggacc ccagaatcat gtgcgtcagt ccaagggtc      7800 ccctccagga gtagtgaaga ctccagaaat gtcccttttct tctcccccat cctacgagta    7860
attgcatttg cttttgtaat tcttaatgag caatatctgc tagagagttt agctgtaaca    7920 gttcttttg atcatctttt tttaataatt agaaacacca aaaaaatcca gaaacttgtt    7980
cttccaaagc agagagcatt ataatcacca gggccaaaag cttccctccc tgctgtcatt    8040
gcttcttctg aggcctgaat ccaaaagaaa aacagccata gccctttca gtggccgggc    8100 tacccgtgag cccttcggag gaccagggct ggggcagcct ctgggcccac atccggggcc    8160
agctccggcg tgtgttcagt gttagcagtg ggtcatgatg ctctttccca cccagcctgg    8220 gatagggca gaggaggcga ggaggccgtt gccgctgatg tttggccgtg aacaggtggg    8280
tgtctgcgtg cgtccacgtg cgtgttttct gactgacatg aaatcgacgc ccagttagc    8340 ctcacccggt gacctctagc cctgcccgga tggagcgggg cccacccggt tcagtgtttc    8400
tggggagctg gacagtggag tgcaaaaggc ttgcagaact tgaagcctgc tccttccctt    8460
gctaccacgg cctcctttcc gtttgatttg tcactgcttc aatcaataac agccgctcca    8520
gagtcagtag tcaatgaata tatgaccaaa tatcaccagg actgttactc aatgtgtgcc    8580
gagcccttgc ccatgctggg ctcccgtgta tctggacact gtaacgtgtg ctgtgtttgc    8640
tccccttccc cttccttctt tgcccttac ttgtctttct ggggttttc tgtttgggtt      8700 tggtttggtt tttattttctc ctttttgtgtt ccaaacatga ggttctctct actggtcctc    8760
ttaactgtgg tgttgaggct tatatttgtg taattttggg tggggtgaaag gaattttgct    8820 aagtaaatct cttctgtgtt tgaactgaag tctgtattgt aactatgttt aaagtaattg    8880
ttccagagac aaatatttct agacactttt tctttacaaa caaaagcatt cggagggagg    8940
gggatggtga ctgagatgag aggggagagc tgaacagatg acccctgccc agatcagcca    9000
gaagccaccc aaagcagtgg agcccaggag tcccactcca agccagcaag ccgaatagct    9060
gatgtgttgc cactttccaa gtcactgcaa aaccaggttt tgttccgccc agtggattct    9120
tgttttgctt ccccctccccc cgagattatt accaccatcc cgtgctttta aggaaaggca    9180
agattgatgt ttccttgagg ggagccagga ggggatgtgt gtgtgcagag ctgaagagct    9240
ggggagaatg gggctgggcc cacccaagca ggaggctggg acgctctgct gtgggcacag    9300
gtcaggctaa tgttggcaga tgcagctctt cctggacagg ccaggtggtg ggcattctct    9360
ctccaaggtg tgccccgtgg gcattactgt ttaagacact tccgtcacat cccaccccat    9420
cctccagggc tcaacactgt gacatctcta ttccccaccc tccccttccc agggcaataa    9480
aatgaccatg gagggggctt gcactctctt ggctgtcacc cgatcgccag caaaacttag    9540
atgtgagaaa accccttccc attccatggc gaaaacatct ccttagaaaa gccattaccc    9600
tcattaggca tggttttggg ctcccaaaac acctgacagc ccctccctcc tctgagaggc    9660
ggagagtgct gactgtagtg accattgcat gccgggtgca gcatctggaa gagctaggca    9720
gggtgtctgc ccctcctga gttgaagtca tgctccctg tgccagccca gaggccgaga      9780
gctatggaca gcattgccag taacacaggc caccctgtgc agaagggagc tggctccagc    9840
ctggaaacct gtctgaggtt gggagaggtg cacttgggc acaggagag gccgggacac      9900 acttagctgg agatgtctct aaaagccctg tatcgtattc accttcagtt tttgtgtttt    9960
gggacaatta ctttagaaaa taagtaggtc gttttaaaaa caaaaattat tgattgcttt    10020
tttgtagtgt tcagaaaaaa ggttctttgt gtatagccaa atgactgaaa gcactgatat    10080
atttaaaaac aaaaggcaat ttattaagga aatttgtacc atttcagtaa acctgtctga    10140
```

```
atgtacctgt atacgtttca aaaacacccc cccccactg aatccctgta acctatttat    10200
tatataaaga gtttgcctta taaattt                                       10227

<210> SEQ ID NO 29
<211> LENGTH: 10227
<212> TYPE: DNA
<213> ORGANISM: Homo sapiens

<400> SEQUENCE: 29
gggcgcgcgc gctccctcct ctcggagagg gctgtggtaa aagccgtccg gaaaatggcc      60
gccgccgccg ccgccgccga gcggaggagg aggaggaggc gaggaggaga gactgctcca     120
taaaaataca gactcaccag ttcctgcttt gatgtgacat gtgactcccc agaatacacc     180
ttgcttctgt agaccagctc aacaggatt ccatggtagc tgggatgtta gggctcaggg      240
aagaaaagtc agaagaccag gacctccagg gcctcaagga caaacccctc aagtttaaaa     300
aggtgaagaa agataagaaa gaagagaaag agggcaagca tgagcccgtg cagccatcag     360
cccaccactc tgctgagccc gcagaggcag gcaaagcaga gacatcagaa gggtcaggct     420
ccgccccggc tgtgccggaa gcttctgcct ccccaaaaca gcggcgctcc atcatccgtg     480
accggggacc catgtatgat gaccccaccc tgcctgaagg ctggacacgg aagcttaagc     540
aaaggaaatc tggccgctct gctgggaagt atgatgtgta tttgatcaat ccccagggaa     600
aagcctttcg ctctaaagtg gagttgattg cgtacttcga aaaggtaggc gacacatccc     660
tggaccctaa tgattttgac ttcacggtaa ctgggagagg gagcccctcc cggcgagagc     720
agaaaccacc taagaagccc aaatctccca agctccagg aactggcaga ggccggggac      780
gccccaaagg gagcggcacc acgagaccca aggcggccac gtcagagggt gtgcaggtga     840
aaagggtcct ggagaaaagt cctgggaagc tccttgtcaa gatgcctttt caaacttcgc     900
cagggggcaa ggctgagggg ggtgggggcca ccacatccac ccaggtcatg gtgatcaaac    960
gccccggcag gaagcgaaaa gctgaggccg accctcaggc cattcccaag aaacggggcc    1020
gaaagccggg gagtgtggtg gcagccgctg ccgccgaggc caaaaagaaa gccgtgaagg    1080
agtcttctat ccgatctgtg caggagaccg tactccccat caagaagcgc aagacccggg    1140
agacggtcag catcgaggtc aaggaagtgg tgaagcccct gctggtgtcc accctcggtg    1200
agaagagcgg gaaaggactg aagacctgta agagccctgg gcggaaaagc aaggagagca    1260
gccccaaggg gcgcagcagc agcgcctcct caccccccaa gaaggagcac caccaccatc    1320
accaccactc agagtcccca aaggccccg tgccactgct cccacccctg cccccacctc     1380
cacctgagcc cgagagctcc gaggacccca ccagccccc tgagcccag gacttgagca      1440 gcagcgtctg caaagaggag aagatgccca gaggaggctc actggagagc gacggctgcc    1500
ccaaggagcc agctaagact cagcccgcgg ttgccaccgc cgccacggcc gcagaaaagt    1560
acaaacaccg aggggaggga gagcgcaaag acattgtttc atcctccatg ccaaggccaa    1620
acagagagga gcctgtggac agccggacgc ccgtgaccga gagagttagc tgactttaca    1680
cggagcggat tgcaaagcaa accaacaaga ataaaggcag ctgttgtctc ttctccttat    1740
gggtagggct ctgacaaagc ttcccgatta actgaaataa aaaatatttt tttttctttc    1800
agtaaactta gagtttcgtg gcttcagggt gggagtagtt ggagcattgg ggatgttttt    1860
cttaccgaca agcacagtca ggttgaagac ctaaccaggg ccagaagtag cttttgcactt   1920 ttctaaacta ggctccttca acaaggcttg ctgcagatac tactgaccag acaagctgtt   1980
```

```
gaccaggcac ctcccctccc gcccaaacct ttcccccatg tggtcgttag agacagagcg    2040
acagagcagt tgagaggaca ctcccgtttt cggtgccatc agtgcccgt  ctacagctcc    2100
cccagctccc cccacctccc ccactcccaa ccacgttggg acagggaggt gtgaggcagg    2160
agagacagtt ggattcttta gagaagatgg atatgaccag tggctatggc ctgtgcgatc    2220
ccacccgtgg tggctcaagt ctggccccac accagcccca atccaaaact ggcaaggacg    2280
cttcacagga caggaaagtg gcacctgtct gctccagctc tggcatggct aggaggggg    2340
agtcccttga actactgggt gtagactggc ctgaaccaca ggagaggatg cccagggtg     2400
aggtggcatg gtccattctc aagggacgtc ctccaacggg tggcgctaga ggccatggag    2460
gcagtaggac aaggtgcagg caggctggcc tggggtcagg ccgggcagag cacagcgggg    2520
tgagagggat tcctaatcac tcagagcagt ctgtgactta gtggacaggg gaggggcaa     2580
agggggagga gaagaaaatg ttcttccagt tactttccaa ttctccttta gggacagctt    2640
agaattattt gcactattga gtcttcatgt tcccacttca aaacaaacag atgctctgag    2700
agcaaactgg cttgaattgg tgacatttag tccctcaagc caccagatgt gacagtgttg    2760
agaactacct ggatttgtat atatacctgc gcttgtttta aagtgggctc agcacatagg    2820
gttcccacga agctccgaaa ctctaagtgt ttgctgcaat tttataagga cttcctgatt    2880
ggtttctctt ctcccttcc  atttctgcct tttgttcatt tcatccttc  acttctttcc    2940
cttcctccgt cctcctcctt cctagttcat cccttctctt ccaggcagcc gcggtgccca    3000
accacacttg tcggctccag tccccagaac tctgcctgcc ctttgtcctc ctgctgccag    3060
taccagcccc accctgtttt gagccctgag gaggccttgg gctctgctga gtccgacctg    3120
gcctgtctgt gaagagcaag agagcagcaa ggtcttgctc tcctaggtag ccccctcttc    3180
cctggtaaga aaaagcaaaa ggcatttccc accctgaaca acgagccttt tcacccttct    3240
actctagaga agtggactgg aggagctggg cccgatttgg tagttgagga aagcacagag    3300
gcctcctgtg gcctgccagt catcgagtgg cccaacaggg gctccatgcc agccgacctt    3360
gacctcactc agaagtccag agtctagcgt agtgcagcag ggcagtagcg gtaccaatgc    3420
agaactccca agaccgagc  tgggaccagt acctgggtcc ccagcccttc ctctgctccc    3480
ccttttccct cggagttctt cttgaatggc aatgttttgc ttttgctcga tgcagacagg    3540
gggccagaac accacacatt tcactgtctg tctggtccat agctgtggtg tagggctta    3600
gaggcatggg cttgctgtgg gttttttaatt gatcagtttt catgtgggat cccatctttt   3660
taacctctgt tcaggaagtc cttatctagc tgcatatctt catcatattg gtatatcctt    3720
ttctgtgttt acagagatgt ctcttatatc taaatctgtc caactgagaa gtaccttatc    3780
aaagtagcaa atgagacagc agtccttatgc ttccagaaac acccacaggc atgtcccatg   3840
tgagctgctg ccatgaactg tcaagtgtgt gttgtcttgt gtatttcagt tattgtccct    3900
ggcttcctta ctatggtgta atcatgaagg agtgaaacat catagaaact gtctagcact    3960
tccttgccag tctttagtga tcaggaacca tagttgacag ttccaatcag tagcttaaga    4020
aaaaaccgtg tttgtctctt ctggaatggt tagaagtgag ggagtttgcc ccgttctgtt    4080
tgtagagtct catagttgga cttttctagca tatatgtgtc catttcctta tgctgtaaaa    4140
gcaagtcctg caaccaaact cccatcagcc caatccctga tccctgatcc cttccacctg    4200
ctctgctgat gaccccccca gcttcacttc tgactcttcc ccaggaaggg aaggggggtc    4260
agaagagagg gtgagtcctc cagaactctt cctccaagga cagaaggctc ctgccccat     4320
agtggcctcg aactcctggc actaccaaag gacacttatc cacgagagcg cagcatccga    4380
```

-continued

```
ccaggttgtc actgagaaga tgtttatttt ggtcagttgg gttttatgt attatactta   4440
gtcaaatgta atgtggcttc tggaatcatt gtccagagct gcttcccgt cacctgggcg    4500
tcatctggtc ctggtaagag gagtgcgtgg cccaccaggc cccctgtca cccatgacag    4560
ttcattcagg gccgatgggg cagtcgtggt tgggaacaca gcatttcaag cgtcacttta   4620
tttcattcgg gccccacctg cagctccctc aaagaggcag ttgcccagcc tctttccctt   4680
ccagtttatt ccagagctgc cagtggggcc tgaggctcct tagggttttc tctctatttc   4740
cccctttctt cctcattccc tcgtctttcc caaaggcatc acgagtcagt cgcctttcag   4800
caggcagcct tggcggttta tcgccctggc aggcaggggc cctgcagctc tcatgctgcc   4860
cctgccttgg ggtcaggttg acaggaggtt ggagggaaag ccttaagctg caggattctc   4920
accagctgtg tccggcccag ttttggggtg tgacctcaat ttcaattttg tctgtacttg   4980
aacattatga agatgggggc ctctttcagt gaatttgtga acagcagaat tgaccgacag   5040
ctttccagta cccatggggc taggtcatta aggccacatc cacagtctcc cccacccttg   5100
ttccagttgt tagttactac ctcctctcct gacaatactg tatgtcgtcg agctccccc    5160
aggtctaccc ctcccggccc tgcctgctgg tgggcttgtc atagccagtg ggattgccgg   5220
tcttgacagc tcagtgagct ggagatactt ggtcacagcc aggcgctagc acagctccct   5280
tctgttgatg ctgtattccc atatcaaaag acacaggga cacccagaaa cgccacatcc    5340
cccaatccat cagtgccaaa ctagccaacg gccccagctt ctcagctcgc tggatggcgg   5400
aagctgctac tcgtgagcgc cagtgcgggt gcagacaatc ttctgttggg tggcatcatt   5460
ccaggcccga agcatgaaca gtgcacctgg gacagggagc agccccaaat tgtcacctgc   5520
ttctctgccc agcttttcat tgctgtgaca gtgatggcga agagggtaa taaccagaca    5580
caaactgcca agttgggtgg agaaaggagt ttctttagct gacagaatct ctgaatttta   5640
aatcacttag taagcggctc aagcccagga gggagcagag ggatacgagc ggagtccct    5700
gcgcgggacc atctggaatt ggtttagccc aagtggagcc tgacagccag aactctgtgt   5760
ccccgtcta accacagctc cttttccaga gcattccagt caggctctct gggctgactg    5820
ggccagggga ggttacaggt accagttctt taagaagatc tttgggcata tacatttta    5880
gcctgtgtca ttgccccaaa tggattcctg tttcaagttc acacctgcag attctaggac   5940
ctgtgtccta gacttcaggg agtcagctgt ttctagagtt cctaccatgg agtgggtctg   6000
gaggacctgc ccggtggggg ggcagagccc tgctccctcc gggtcttcct actcttctct   6060
ctgctctgac gggatttgtt gattctctcc attttggtgt ctttctcttt tagatattgt   6120
atcaatcttt agaaaaggca tagtctactt gttataaatc gttaggatac tgcctccccc   6180
agggtctaaa attacatatt agaggggaaa agctgaacac tgaagtcagt tctcaacaat   6240
ttagaaggaa aacctagaaa acatttggca gaaaattaca tttcgatgtt tttgaatgaa   6300
tacgagcaag cttttacaac agtgctgatc taaaaatact tagcacttgg cctgagatgc   6360
ctggtgagca ttacaggcaa ggggaatctg gaggtagccg acctgaggac atggcttctg   6420
aacctgtctt ttgggagtgg tatggaaggt ggagcgttca ccagtgacct ggaaggccca   6480
gcaccaccct ccttcccact cttctcatct tgacagagcc tgcccagcg ctgacgtgtc    6540
aggaaaacac ccagggaact aggaaggcac ttctgcctga ggggcagcct gccttgccca   6600
ctcctgctct gctcgcctcg gatcagctga gccttctgag ctggcctctc actgcctccc   6660
caaggccccc tgcctgccct gtcaggaggc agaaggaagc aggtgtgagg gcagtgcaag   6720
```

```
gagggagcac aacccccagc tcccgctccg ggctccgact tgtgcacagg cagagcccag   6780
accctggagg aaatcctacc tttgaattca agaacatttg gggaatttgg aaatctcttt   6840
gcccccaaac ccccattctg tcctaccttt aatcaggtcc tgctcagcag tgagagcaga   6900
tgaggtgaaa aggccaagag gtttggctcc tgcccactga tagcccctct ccccgcagtg   6960
tttgtgtgtc aagtggcaaa gctgttcttc ctggtgaccc tgattatatc cagtaacaca   7020
tagactgtgc gcataggcct gctttgtctc ctctatcctg ggcttttgtt ttgcttttta   7080
gttttgcttt tagttttct gtcccttta tttaacgcac cgactagaca cacaaagcag   7140
ttgaattttt atatatatat ctgtatattg cacaattata aactcatttt gcttgtggct   7200
ccacacacac aaaaaaagac ctgttaaaat tatacctgtt gcttaattac aatatttctg   7260
ataaccatag cataggacaa gggaaaataa aaaagaaaaa aaaagaaaaa aaacgacaa    7320 atctgtctgc tggtcacttc ttctgtccaa gcagattcgt ggtcttttcc tcgcttcttt   7380
caagggcttt cctgtgccag gtgaaggagg ctccaggcag cacccaggtt ttgcactctt   7440
gtttctcccg tgcttgtgaa agaggtccca aggttctggg tgcaggagcg ctcccttgac   7500
ctgctgaagt ccggaacgta gtcggcacag cctggtcgcc ttccacctct gggagctgga   7560
gtccactggg gtggcctgac tcccccagtc cccttcccgt gacctggtca gggtgagccc   7620
atgtggagtc agcctcgcag gcctccctgc cagtagggtc cgagtgtgtt tcatccttcc   7680
cactctgtcg agcctggggg ctggagcgga gacgggaggc ctggcctgtc tcggaacctg   7740
tgagctgcac caggtagaac gccagggacc ccagaatcat gtgcgtcagt ccaaggggtc   7800
ccctccagga gtagtgaaga ctccagaaat gtcccttct tctcccccat cctacgagta   7860
attgcatttg cttttgtaat tcttaatgag caatatctgc tagagagttt agctgtaaca   7920 gttcttttg atcatctttt tttaataatt agaaacacca aaaaaatcca gaaacttgtt   7980
cttccaaagc agagagcatt ataatcacca gggccaaaag cttccctccc tgctgtcatt   8040
gcttcttctg aggcctgaat ccaaaagaaa aacagccata ggcccttca gtggccgggc   8100 tacccgtgag cccttcggag gaccagggct ggggcagcct ctgggcccac atccggggcc   8160
agctccggcg tgtgttcagt gttagcagtg ggtcatgatg ctctttccca cccagcctgg   8220
gataggggca gaggaggcga ggaggccgtt gccgctgatg tttggccgtg aacaggtggg   8280
tgtctgcgtg cgtccacgtg cgtgttttct gactgacatg aaatcgacgc ccgagttagc   8340
ctcacccggt gacctctagc cctgcccgga tggagcgggg cccacccggt tcagtgtttc   8400
tggggagctg gacagtggag tgcaaaaggc ttgcagaact tgaagcctgc tccttccctt   8460
gctaccacgg cctcctttcc gtttgatttg tcactgcttc aatcaataac agccgctcca   8520
gagtcagtag tcaatgaata tatgaccaaa tatcaccagg actgttactc aatgtgtgcc   8580
gagcccttgc ccatgctggg ctcccgtgta tctggacact gtaacgtgtg ctgtgtttgc   8640
tccccttccc cttccttctt tgcccttac ttgtctttct ggggttttc tgtttgggtt   8700 tggtttggtt tttatttctc cttttgtgtt ccaaacatga ggttctctct actggtcctc   8760
ttaactgtgg tgttgaggct tatatttgtg taattttgg tgggtgaaag gaattttgct   8820
aagtaaatct cttctgtgtt tgaactgaag tctgtattgt aactatgttt aaagtaattg   8880
ttccagagac aaatatttct agacactttt tctttacaaa caaaagcatt cggagggagg   8940
gggatggtga ctgagatgag agggagagc tgaacagatg accctgccc agatcagcca   9000 gaagccaccc aaagcagtgg agcccaggag tcccactcca agccagcaag ccgaatagct   9060
gatgtgttgc cactttccaa gtcactgcaa aaccaggttt tgttccgccc agtggattct   9120
```

```
tgttttgctt ccccctccccc cgagattatt accaccatcc cgtgctttta aggaaaggca    9180
agattgatgt ttccttgagg ggagccagga ggggatgtgt gtgtgcagag ctgaagagct    9240
ggggagaatg gggctgggcc cacccaagca ggaggctggg acgtctgct gtgggcacag     9300 gtcaggctaa tgttggcaga tgcagctctt cctggacagg ccaggtggtg ggcattctct    9360
ctccaaggtg tgccccgtgg gcattactgt ttaagacact tccgtcacat cccaccccat    9420
cctccagggc tcaacactgt gacatctcta ttccccaccc tccccttccc agggcaataa    9480
aatgaccatg gaggggggctt gcactctctt ggctgtcacc cgatcgccag caaaacttag   9540
atgtgagaaa accccttccc attccatggc gaaaacatct ccttagaaaa gccattaccc    9600
tcattaggca tggttttggg ctcccaaaac acctgacagc ccctccctcc tctgagaggc    9660
ggagagtgct gactgtagtg accattgcat gccgggtgca gcatctggaa gagctaggca    9720
gggtgtctgc cccctcctga gttgaagtca tgctcccctg tgccagccca gaggccgaga    9780
gctatggaca gcattgccag taacacaggc caccctgtgc agaagggagc tggctccagc    9840
ctggaaacct gtctgaggtt gggagaggtg cacttggggc acagggagag gccgggacac    9900
acttagctgg agatgtctct aaaagccctg tatcgtattc accttcagtt tttgtgtttt    9960
gggacaatta ctttagaaaa taagtaggtc gttttaaaaa caaaaattat tgattgcttt   10020
tttgtagtgt tcagaaaaaa ggttctttgt gtatagccaa atgactgaaa gcactgatat   10080
atttaaaaac aaaaggcaat ttattaagga aatttgtacc atttcagtaa acctgtctga   10140
atgtacctgt atacgtttca aaaacacccc cccccactg aatccctgta acctatttat    10200
tatataaaga gtttgcctta taaattt                                       10227
```

<210> SEQ ID NO 30
<211> LENGTH: 9
<212> TYPE: PRT
<213> ORGANISM: Homo sapiens

<400> SEQUENCE: 30

Met Val Ala Gly Met Leu Gly Leu Arg
1               5

<210> SEQ ID NO 31
<211> LENGTH: 21
<212> TYPE: PRT
<213> ORGANISM: Homo sapiens

<400> SEQUENCE: 31

Met Ala Ala Ala Ala Ala Ala Ala Pro Ser Gly Gly Gly Gly Gly Gly
1               5                   10                  15

Glu Glu Glu Arg Leu
            20

<210> SEQ ID NO 32
<211> LENGTH: 21
<212> TYPE: PRT
<213> ORGANISM: Pan troglodytes

<400> SEQUENCE: 32

Met Ala Ala Ala Ala Ala Ala Ala Pro Ser Gly Gly Gly Gly Gly Gly
1               5                   10                  15

Glu Glu Glu Arg Leu
            20

```
<210> SEQ ID NO 33
<211> LENGTH: 26
<212> TYPE: PRT
<213> ORGANISM: Mus musculus

<400> SEQUENCE: 33

Met Ala Ala Ala Ala Thr Ala Ala Ala Ala Ala Pro Ser Gly
1               5                   10                  15

Gly Gly Gly Gly Gly Glu Glu Glu Arg Leu
            20                  25

<210> SEQ ID NO 34
<211> LENGTH: 37
<212> TYPE: PRT
<213> ORGANISM: Rattus norvegicus

<400> SEQUENCE: 34

Met Ala Ala Ala Ala Ala Ala Ala Ala Ala Ala Ala Ala Ala Ala
1               5                   10                  15

Ala Ala Ala Ala Ala Ala Ala Ala Pro Ser Gly Gly Gly Gly Gly
                20                  25                  30

Glu Glu Glu Arg Leu
        35

<210> SEQ ID NO 35
<211> LENGTH: 21
<212> TYPE: PRT
<213> ORGANISM: Felis catus

<400> SEQUENCE: 35

Met Ala Ala Ala Ala Ala Ala Ala Pro Ser Gly Gly Gly Gly Gly
1               5                   10                  15

Glu Glu Glu Arg Leu
            20

<210> SEQ ID NO 36
<211> LENGTH: 15
<212> TYPE: PRT
<213> ORGANISM: Gallus gallus

<400> SEQUENCE: 36

Met Ala Ala Ala Ala Ala Ala Ala Ala Gly Gly Glu Glu Arg Leu
1               5                   10                  15

<210> SEQ ID NO 37
<211> LENGTH: 11
<212> TYPE: PRT
<213> ORGANISM: Xenopus laevis

<400> SEQUENCE: 37

Met Ala Ala Ala Pro Ser Gly Glu Glu Arg Leu
1               5                   10

<210> SEQ ID NO 38
<211> LENGTH: 11
<212> TYPE: PRT
<213> ORGANISM: Danio rerio

<400> SEQUENCE: 38

Met Ala Ala Ala Glu Ser Gly Glu Glu Arg Leu
1               5                   10

<210> SEQ ID NO 39
```

```
<211> LENGTH: 9
<212> TYPE: PRT
<213> ORGANISM: Fugu rubripes

<400> SEQUENCE: 39

Met Ala Ala Val Glu Ser Gly Glu Glu
1               5

<210> SEQ ID NO 40
<211> LENGTH: 13
<212> TYPE: PRT
<213> ORGANISM: Homo sapiens

<400> SEQUENCE: 40

Met Ala Ala Ala Ala Ala Gln Gly Gly Gly Gly Gly Glu
1               5                   10

<210> SEQ ID NO 41
<211> LENGTH: 14
<212> TYPE: PRT
<213> ORGANISM: Mus musculus

<400> SEQUENCE: 41

Met Ala Ala Ala Ala Ala Ala Pro Gly Gly Gly Gly Gly Glu
1               5                   10

<210> SEQ ID NO 42
<211> LENGTH: 14
<212> TYPE: PRT
<213> ORGANISM: Rattus norvegicus

<400> SEQUENCE: 42

Met Ala Ala Ala Ala Ala Ala Pro Gly Gly Gly Gly Gly Glu
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Pro Ser Gly Gly Gly Gly Gly Gly Glu Glu Glu Arg Leu
1               5                   10

<210> SEQ ID NO 44
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ccgagcggag gaggaggagg aggcgaggag gagagactg                              39

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45
```

Ala Ala Pro Ser Gly Gly Gly Gly Glu Thr Val Glu Trp
1               5                   10

<210> SEQ ID NO 46
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cgccgcgccg agcggaggag gaggaggaga gactgtgagt gg                        42

<210> SEQ ID NO 47
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ggcgtcggcg gcgcgcgctc cctcctctcg gagagaggct gtggtaaaag ccgtccc       57

<210> SEQ ID NO 48
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Met Ala Ala Ala Ala Ala Ala Ala Pro Ser Gly Gly Gly Gly Gly Gly
1               5                   10                  15

Gly Glu Glu Glu Arg Leu
            20

<210> SEQ ID NO 49
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gaaaatggcc gccgccgccg ccgccgcgcc gagggaggag gaggaggagg agccg         55

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Met Ala Ala Ala Ala Ala Ala Pro Ser Gly Gly Gly Gly Gly Gly Glu
1               5                   10                  15

Glu Glu Arg Leu
        20

<210> SEQ ID NO 51

```
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gaaaatggcc gccgccgccg ccgcgccgag cggaggagga ggaggaggcg aggaggaga     59

<210> SEQ ID NO 52
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Met Ala Ala Ala Ala Ala Ala Ala Ala Ala Pro Ser Gly Gly Gly
1               5                   10                  15

Gly Gly Gly Glu Glu Glu Arg Leu
            20

<210> SEQ ID NO 53
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gccgtccgga aaatggccgc cgccgccgcc gccgccgccg ccgcgccgag cggaggagga    60

<210> SEQ ID NO 54
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Met Ala Ala Ala Ala Ala Ala Ala Pro Ser Gly Gly Gly Gly Gly Gly
1               5                   10                  15

Glu Glu Glu Arg Leu
            20

<210> SEQ ID NO 55
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
cctcctctcg gagagggctg tggtaaaagc cgtccggaaa atc                      43
```

MECP2E1 GENE

RELATED APPLICATIONS

This application is a continuation of U.S. patent application Ser. No. 15/429,143, filed Feb. 9, 2017, which is a continuation of U.S. patent application Ser. No. 14/100,889, filed Dec. 9, 2013, now U.S. Pat. No. 9,605,314, which is a continuation of U.S. patent application Ser. No. 12/657,559, filed Jan. 21, 2010, now U.S. Pat. No. 8,637,236, which is a continuation-in-part of U.S. patent application Ser. No. 11/352,153, filed Feb. 9, 2006, now U.S. Pat. No. 7,670,773, which is a continuation of International Patent Application No. PCT/CA2005/000198, filed Feb. 17, 2005, which claims priority from U.S. Provisional Patent Application No. 60/544,311, filed Feb. 17, 2004. The contents of these applications are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Feb. 28, 2014, is named 103779-0609_SL.txt and is 154,492 bytes in size.

BACKGROUND OF THE INVENTION

Neuropsychiatric disorders account for six of the ten highest impact diseases worldwide, according to the World Health Organization. Cost to the US economy is $100 billion- one of every four persons entering physician offices has a diagnosable mental disorder.

Rett syndrome (RTT) (OMIM #312750) is characterized by onset, in girls, of a gradual slowing of neurodevelopment in the second half of the first year of life towards stagnation by age four, followed by regression and loss of acquired fine motor and communication skills. A pseudostationary period follows during which a picture of preserved ambulation, aberrant communication and stereotypic hand wringing approximates early autism. Regression, however, remains insidiously ongoing and ultimately results in profound mental retardation.

Up to 80% of patients with RTT have mutations in exons 3 and 4 of the 4-exon MECP2 gene (FIG. 1a) encoding the MeCP2 transcriptional repressor. Mutations in the remaining 20% of patients has remained elusive. In the known transcript of the gene all four exons are utilized, the translation start site is in exon 2, and exon 1 and most of exon 2 form the 5'untranslated region (UTR). For clarity, this transcript is named MECP2E2 (previously MECP2A), and its encoded protein MeCP2E2 (previously MeCP2A).

No mutation specific to the MeCP2E2-defining exon 2 has been found to date despite several hundred patients analyzed for mutations in this exon. These studies did not include exon 1 as it was considered non-coding.

Non-inactivating MECP2 mutations have also been associated with phenotypes that overlap RTT such as mental retardation and autism. There is a need for the identification of further mutations to account for the remaining 20% of RTT patients so that methods of diagnosing and treating RTT can be identified.

Mutations in the Rett syndrome gene, MECP2, have also been found among autism patients as well as in patients with childhood onset psychosis, Angelman syndrome, non-syndromic mental retardation and neo-natal encepalopathy, demonstrating that there may be diverse phenotypic consequences of mutations in MECP2.

SUMMARY OF THE INVENTION

The present inventors have identified a novel open reading frame of the MECP2 gene, that is called MECP2E1. Inspection of the 5'UTR revealed that, whereas exon 2 has a number of in-frame stops upstream of the ATG, exon 1 contains an open reading frame across its entire length including an ATG. This open reading frame encodes a transcript composed of exons 1, 3 and 4 of the MECP2 gene. MECP2E1 is similar to MECP2E2 (GenBank accession # NM_004992, SEQ ID NO. 1, except with nucleotides 71-193 absent, corresponding to the splicing out of exon 2.

Accordingly, the present invention provides an isolated nucleic acid molecule comprising a sequence encoding the MeCP2E1 protein. The invention also includes the corresponding polypeptide, MeCP2E1.

In one embodiment, the purified and isolated nucleic acid molecule comprises
(a) a nucleic acid sequence encoding a protein as shown in SEQ ID No. 4;
(b) a nucleic acid sequence complementary to (a);
(c) a nucleic acid sequence that has substantial homology to (a) or (b);
(d) a nucleic acid sequence that is an analog to a nucleic acid sequence of (a), (b), or (c);
(e) a fragment of (a) to (d) that is at least 15 bases, preferably 20 to 30 bases, and which will hybridize to a nucleic acid sequence of (a), (b), (c) or (d) under stringent hybridization conditions; or
(f) a nucleic acid molecule differing from any of the nucleic acids of (a) to (c) in codon sequences due to the degeneracy of the genetic code.

In a specific embodiment of the invention, an isolated nucleic acid molecule is provided having a sequence as shown in SEQ ID No. 3 or a fragment or variant thereof.

The inventors have found that patients with a neuropsychiatric disorder or developmental disorder such as Rett's syndrome and mental retardation, had mutations in exon 1 of the MECP2E1 gene. Accordingly, the present invention provides a method of detecting a neuropsychiatric disorder or developmental disorder comprising detecting a mutation or deletion in exon 1 of the MECP2E1 sequence (SEQ ID No. 3). A mutation can be detected by sequencing PCR products from genomic DNA using primers X1F/X1R: mutation screening primers (FIG. 1). Detection of insertion or deletion mutations may require the cloning of the PCR product into a suitable plasmid vector, followed by transfection into E. Coli, and sequencing of clones from isolated colonies. Alternatively, a mutation can be detected by multiple ligation-dependent probe amplification (MLPA) using 20 probe pairs that target the four MECP2 exons, six X-linked control regions and ten autosomal control regions. A mutation or deletion can also be detected by assaying for the protein product encoded by MECP2E1.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawings will be provided by the Office upon request and payment of the necessary fee.

The invention will now be described in relation to the drawings in which:

FIGS. 1A-1F shows MECP2 5' splice variants. a) Structure of the MECP2 gene. Numbered boxes indicate exons; asterisks indicate in-frame stop codons. In the traditional MECP2E2 splice variant, the start codon is in exon 2. In MECP2E1, exon 2 is not present and the start codon is in exon 1. HF/HR1 and MF/MR: human and mouse primer pairs used in the rtPCR experiments shown in panel c. HR2: a second human reverse primer, which confirms the results obtained with HR1 (data not shown). X1F/X1R: mutation screening primers (see FIG. 2). Primer sequences (5'-3'): HF-ctcggagagagggctgtg (SEQ ID No. 5), HR1-cttgaggggttt-gtccttga (SEQ ID No. 6), HR2-cgtttgatcaccatgacctg (SEQ ID No. 7), MF-aggaggcgaggaggagagac (SEQ ID No. 8), MR-ctggctctgcagaatggtg (SEQ ID No. 9), X1F-ccatcacagccaat-gacg (SEQ ID No. 19), X1R-aggggagggtagagaggag (SEQ ID No. 20). b) Examples of MECP2 ESTs. c) PCR results using primers in (a) (HF/HR1 and MF/MR) on cDNA from indicated adult tissues (except where indicated otherwise) and cell cultures; d.p.c.: days postcoitum. d) Transcript-specific real-time quantitative PCR (SYBR Green detection method) on cDNA from indicated tissues or cell cultures. e) 3'myc-tagged MeCP2E1 (and MeCP2E2) localize principally in the nucleus, and in indeterminate puncti in the cytoplasm. f) N-termini of indicated proteins (SEQ ID NOS 30-42, respectively, in order of appearance); dashes represent no amino acids.

FIG. 5 discloses SEQ ID NOS 18 and 47-55, respectively, in order of appearance.

DETAILED DESCRIPTION OF THE INVENTION

Figure 1A:
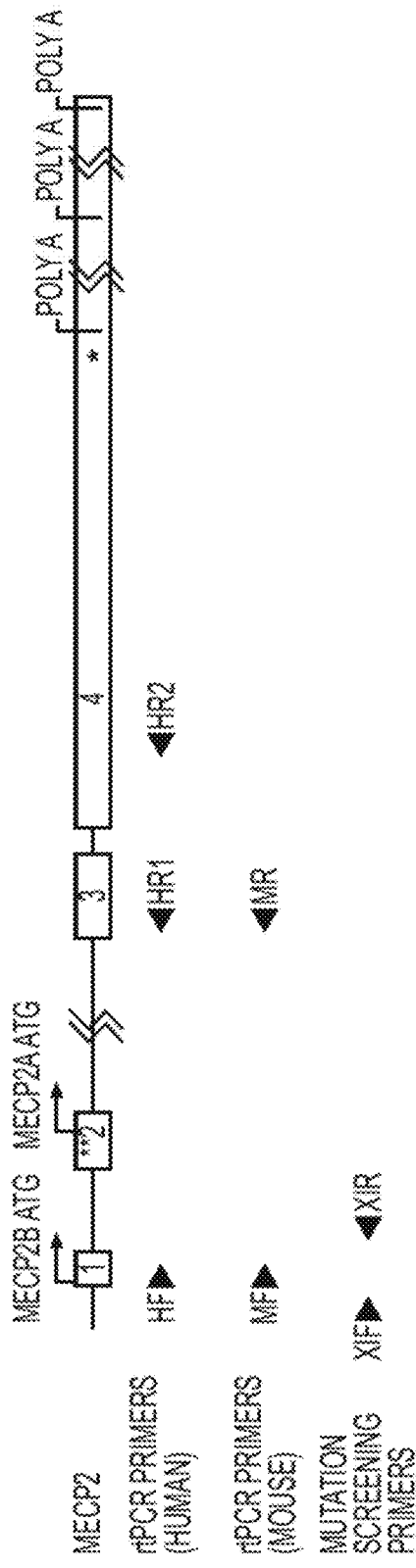
Figure 1B:
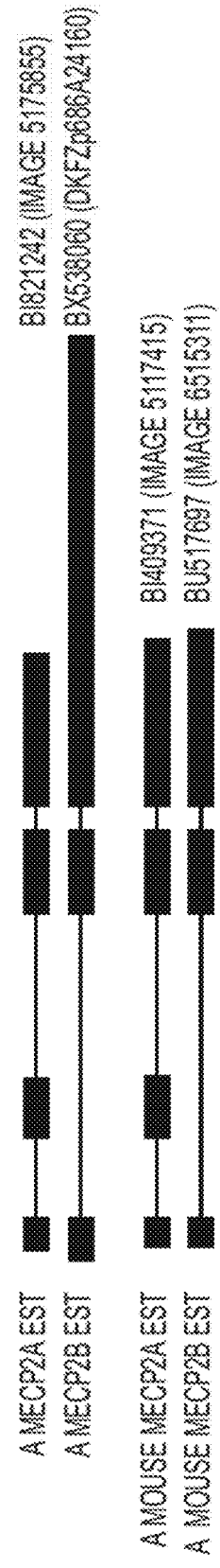

The present inventors have identified a MECP2 splice variant that contributes to new coding sequence that may contain mutations in patients with neuropsychiatric disorders such as Rett's syndrome and mental retardation.

I. Nucleic Acid Molecules of the Invention

As hereinbefore mentioned, the present invention relates to isolated MECP2E1 nucleic acid molecules. The term "isolated" refers to a nucleic acid substantially free of cellular material or culture medium when produced by recombinant DNA techniques, or chemical precursors, or other chemicals when chemically synthesized.

The term "nucleic acid" is intended to include DNA and RNA and can be either double stranded or single stranded. The term is also intended to include a strand that is a mixture of nucleic acid molecules and nucleic acid analogs and/or nucleotide analogs, or that is made entirely of nucleic acid analogs and/or nucleotide analogs.

Broadly stated, the present invention provides an isolated nucleic acid molecule containing a sequence encoding the MECP2E1 transcript of the MECP2 gene. Accordingly, the present invention provides an isolated nucleic acid molecule containing a sequence encoding MECP2E1 shown in SEQ ID No. 4 or a fragment, variant, or analog thereof.

In one embodiment, the purified and isolated nucleic acid molecule comprises (a) a nucleic acid sequence encoding a MECP2E1 protein as shown in SEQ ID No. 4;

(b) a nucleic acid sequence complementary to (a);

(c) a nucleic acid sequence that has substantial homology to (a) or (b);

(d) a nucleic acid sequence that is an analog to a nucleic acid sequence of (a), (b), or (c);

(e) a fragment of (a) to (d) that is at least 15 bases, preferably 20 to 30 bases, and which will hybridize to a nucleic acid sequence of (a), (b), (c) or (d) under stringent hybridization conditions; or (f) a nucleic acid molecule differing from any of the nucleic acids of (a) to (c) in codon sequences due to the degeneracy of the genetic code.

In a specific embodiment of the invention, the isolated nucleic acid molecule has a sequence as shown in SEQ ID No. 3 or a fragment or variant thereof.

The term "MECP2E1" means an isoform of the MECP2 gene that contains exons 1, 3 and 4 but lacks exon 2. This gene was previously referred to as MECP2B but is now called MECP2E1 indicating the translation start site in exon one. The term "MECP2E1" includes the nucleic acid sequence as shown in SEQ ID No. 3 as well as mutations, variants and fragments thereof that are associated with neuropsychiatric disorders and developmental disorders. "MECP2E1" can also be referred to as "MECP2_e1." The "MeCP2E1" protein can also be referred to as "MeCP2_e1." MECP2E2 is the transcript of the gene that contains exons 1, 2, 3 and 4. "MECP2E2" can also be referred to as "MECP2_e2." The "MeCP2E2" protein can also be referred to as "MeCP2_e2."

It will be appreciated that the invention includes nucleic acid molecules encoding truncations of the MeCP2E1 proteins of the invention, and analogs and homologs of the MeCP2E1 proteins of the invention and truncations thereof, as described below.

Further, it will be appreciated that the invention includes nucleic acid molecules comprising nucleic acid sequences having substantial sequence homology with the nucleic acid sequences of the invention and fragments thereof. The term "sequences having substantial sequence homology" means those nucleic acid sequences which have slight or inconsequential sequence variations from these sequences, i.e. the sequences function in substantially the same manner to produce functionally equivalent proteins. The variations may be attributable to local mutations or structural modifications.

Generally, nucleic acid sequences having substantial homology include nucleic acid sequences having at least 70%, preferably 80-90% identity with the nucleic acid sequences of the invention.

Sequence identity is most preferably assessed by the algorithm of the BLAST version 2.1 program advanced search (BLAST is a series of programs that are available online at www.ncbi.nlm.nih.gov/BLAST. The advanced blast search (www.ncbi.nlm.nih.gov/blast/blast.cgi?J-form=1) is set to default parameters. (ie Matrix BLOSUM62; Gap existence cost 11; Per residue gap cost 1; Lambda ratio 0.85 default).). For example, if a nucleotide sequence (called "Sequence A") has 90% identity to a portion of the nucleotide sequence in SEQ ID No. 3, then Sequence A will be identical to the referenced portion of the nucleotide sequence in SEQ ID No. 3, except that Sequence A may include up to 10 point mutations, such as substitutions with other nucleotides, per each 100 nucleotides of the referenced portion of the nucleotide sequence in SEQ ID No. 3. Nucleotide sequences functionally equivalent to the MECP2E1 transcript can occur in a variety of forms as described below.

The term "a nucleic acid sequence which is an analog" means a nucleic acid sequence which has been modified as compared to the sequence of (a), (b) or (c) wherein the modification does not alter the utility of the sequence as described herein. The modified sequence or analog may have improved properties over the sequence shown in (a), (b) or (c). One example of a modification to prepare an analog is to replace one of the naturally occurring bases (i.e. adenine, guanine, cytosine or thymine) of the sequence shown in SEQ ID No. 3, with a modified base such as such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule shown in SEQ ID No. 3. For example, the nucleic acid sequences may contain phosphorothioates, phosphotriesters, methyl phosphonates, and phosphorodithioates.

A further example of an analog of a nucleic acid molecule of the invention is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

Another aspect of the invention provides a nucleic acid molecule, and fragments thereof having at least 15 bases, which hybridizes to the nucleic acid molecules of the invention under hybridization conditions. Such nucleic acid molecules preferably hybridize to all or a portion of MECP2E1 or its complement under stringent conditions as defined herein (see Sambrook et al. (most recent edition) Molecular Cloning: A Laboratory Manual, Cold Spring Harbor Laboratory Press, Cold Spring Harbor, N.Y.; Ausubel et al. (eds.), 1995, Current Protocols in Molecular Biology, (John Wiley & Sons, NY)). The portion of the hybridizing nucleic acids is typically at least 15 (e.g. 20, 25, 30 or 50) nucleotides in length. The hybridizing portion of the hybridizing nucleic acid is at least 80% e.g. at least 95% or at least 98% identical to the sequence or a portion or all of a nucleic acid encoding a MeCP2E1 polypeptide, or its complement. Hybridizing nucleic acids of the type described herein can be used, for example, as a cloning probe, a primer (e.g. a PCR primer) or a diagnostic probe. Hybridization of the oligonucleotide probe to a nucleic acid sample typically is performed under stringent conditions. Nucleic acid duplex or hybrid stability is expressed as the melting temperature or Tm, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g. SSC or SSPE). Then, assuming that 1% mismatching results in a 1 degree Celsius decrease in the Tm, the temperature of the final wash in the hybridization reaction is reduced accordingly (for example, if sequences having greater than 95% identity with the probe are sought, the final wash temperature is decreased by 5 degrees Celsius). In practice, the change in Tm can be between 0.5 degrees Celsius and 1.5 degrees Celsius per 1% mismatch. Low stringency conditions involve hybridizing at about: 1×SSC, 0.1% SDS at 50° C. High stringency conditions are: 0.1×SSC, 0.1% SDS at 65° C. Moderate stringency is about 1×SSC 0.1% SDS at 60 degrees Celsius. The parameters of salt concentration and temperature can be varied to achieve the optimal level of identity between the probe and the target nucleic acid.

Isolated and purified nucleic acid molecules having sequences which differ from the nucleic acid sequence shown in SEQ ID No. 3 due to degeneracy in the genetic code are also within the scope of the invention. The genetic code is degenerate so other nucleic acid molecules, which encode a polypeptide identical to the MeCP2E1 amino acid sequence SEQ ID No. 3 may also be used.

The present invention also includes mutated forms of MEC2P2E1 associated with a neuropsychiatric disorder or developmental disorder including the specific mutations listed in Table 1. Specifically, the following mutations are associated with Rett's syndrome: (1) an 11 bp deletion in nucleotides 38 to 54 shown in SEQ ID No. 1; (2) a deletion of exon 1 containing nucleotides 1-69 shown in SEQ ID No. 1; (3) an adenine to thymine change at nucleotide position 8 shown in SEQ ID No. 1; (4) a deletion in the sequence TG at nucleotide positions 70-71 in SEQ ID No. 1 (5) an adenine to guanine change at nucleotide position 8 shown in SEQ ID No. 1; (6) a cytosine to thymine change at nucleotide position 12 shown in SEQ ID No. 1; and (7) a deletion in the sequence TG at nucleotide positions 69 and 70 in SEQ ID No. 1.

The following mutations are associated with developmental delay: (1) an insertion of one or more copies of the trinucleotide sequence GCC between nucleotides 11 and 29 shown in SEQ ID No. 1; (2) a deletion of one or more copies of the trinucleotide sequence GCC between nucleotides 11 and 29 shown in SEQ ID No. 1; (3) an insertion of the nucleotide sequence GGA between nucleotides 38 and 54 shown in SEQ ID No. 1; (4) a deletion of the nucleotide sequence GC at nucleotides −38 and −39 upstream of nucleotide 1 shown in SEQ ID No. 1; and (5) a deletion of the nucleotide sequence AG at nucleotides −19 and −20 upstream of nucleotide 1 shown in SEQ ID No. 1.

With respect to mutations (4) and (5) in the developmental delay group, these are upstream of nucleotide 1 shown in SEQ ID No. 1 GenBank Accession number BX538060 has the upstream sequences. Therefore, for greater clarity mutation (4), that consists of a deletion of the nucleotide sequence GC at nucleotides −38 and −39, corresponds to nucleotides 11-12 of sequence BX538060; and mutation (5), that consists of a deletion of the nucleotide sequence AG at nucleotides −19 and −20, corresponds to nucleotides 30-31 of BX538060.

Nucleic acid molecules from MECP2E1 can be isolated by preparing a labeled nucleic acid probe based on all or part of the nucleic acid sequences as shown in SEQ ID No. 3, and using this labelled nucleic acid probe to screen an appropriate DNA library (e.g. a cDNA or genomic DNA library). Nucleic acids isolated by screening of a cDNA or genomic DNA library can be sequenced by standard techniques. Another method involves comparing the MECP2E1 sequence to other sequences, for example using bioinformatics techniques such as database searches or alignment strategies, and detecting the presence of a MECP2E1 nucleic acid sequence.

Nucleic acid molecules of the invention can also be isolated by selectively amplifying a nucleic acid using the polymerase chain reaction (PCR) methods and cDNA or genomic DNA. It is possible to design synthetic oligonucleotide primers from the nucleic acid molecules as shown in SEQ ID No. 3 for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294-5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the invention which is RNA can be isolated by cloning a cDNA encoding a novel protein of the invention into an appropriate vector which allows for transcription of the cDNA to produce an RNA molecule which encodes the MeCP2E1 protein. For example, a cDNA can be cloned downstream of a bacteriophage promoter, (e.g. a T7 promoter) in a vector, cDNA can be transcribed in vitro with T7 polymerase, and the resultant RNA can be isolated by standard techniques.

A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

The initiation codon and untranslated sequences of the nucleic acid molecules of the invention may be determined using currently available computer software designed for the purpose, such as PC/Gene (IntelliGenetics Inc., Calif.). Regulatory elements can be identified using conventional techniques. The function of the elements can be confirmed by using these elements to express a reporter gene which is operatively linked to the elements. These constructs may be introduced into cultured cells using standard procedures. In addition to identifying regulatory elements in DNA, such constructs may also be used to identify proteins interacting with the elements, using techniques known in the art.

The sequence of a nucleic acid molecule of the invention may be inverted relative to its normal presentation for transcription to produce an antisense nucleic acid molecule. Preferably, an antisense sequence is constructed by inverting a region preceding the initiation codon or an unconserved region. In particular, the nucleic acid sequences contained in the nucleic acid molecules of the invention or a fragment thereof, preferably a nucleic acid sequence shown in SEQ ID No. 3 may be inverted relative to its normal presentation for transcription to produce antisense nucleic acid molecules.

The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The invention also provides nucleic acids encoding fusion proteins comprising a novel protein of the invention and a selected protein, or a selectable marker protein (see below).

II. Novel Proteins of the Invention

The invention further includes an isolated MeCP2E1 protein encoded by the nucleic acid molecules of the invention. Within the context of the present invention, a protein of the invention may include various structural forms of the primary protein which retain biological activity.

Broadly stated, the present invention provides an isolated protein encoded by exon 1, 3 and 4 of the MECP2 gene.

In a preferred embodiment of the invention, the MeCP2E1 protein has the amino acid sequence as shown in SEQ ID No. 4 or a fragment or variant thereof.

The invention also includes mutated forms of the MeCP2E1 protein that are associated with a neuropsychiatric disorder or developmental disorder. Specifically, the invention includes the mutations in MECP2E1 described in Table 1.

In addition to full length amino acid sequences, the proteins of the present invention also include truncations of the protein, and analogs, and homologs of the protein and truncations thereof as described herein. Truncated proteins may comprise peptides of at least fifteen amino acid residues.

Analogs or variants of the protein having the amino acid sequence shown in SEQ ID No. 4 and/or truncations thereof as described herein, may include, but are not limited to an amino acid sequence containing one or more amino acid substitutions, insertions, and/or deletions. Amino acid substitutions may be of a conserved or non-conserved nature. Conserved amino acid substitutions involve replacing one or more amino acids of the proteins of the invention with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

One or more amino acid insertions may be introduced into the amino acid sequence shown in SEQ ID No. 4. Amino acid insertions may consist of single amino acid residues or sequential amino acids ranging from 2 to 15 amino acids in length. For example, amino acid insertions may be used to destroy target sequences so that the protein is no longer active. This procedure may be used in vivo to inhibit the activity of a protein of the invention.

Deletions may consist of the removal of one or more amino acids, or discrete portions from the amino acid sequence shown in SEQ ID No. 4. The deleted amino acids may or may not be contiguous. The lower limit length of the resulting analog with a deletion mutation is about 10 amino acids, preferably 100 amino acids.

Analogs of a protein of the invention may be prepared by introducing mutations in the nucleotide sequence encoding the protein. Mutations in nucleotide sequences constructed for expression of analogs of a protein of the invention must preserve the reading frame of the coding sequences. Furthermore, the mutations will preferably not create complementary regions that could hybridize to produce secondary mRNA structures, such as loops or hairpins, which could adversely affect translation of the receptor mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site specific mutagenesis procedures may be employed to provide an altered gene having particular codons altered according to the substitution, deletion, or insertion required. Deletion or truncation of a protein of the invention may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al (Molecular Cloning: A Laboratory Manual, 2nd Ed., Cold Spring Harbor Laboratory Press, 1989).

The proteins of the invention also include homologs of the amino acid sequence having the exon 1 region shown in SEQ ID No. 4 and/or truncations thereof as described herein.

A homologous protein includes a protein with an amino acid sequence having at least 70%, preferably 80-90% identity with the amino acid sequence as shown in SEQ ID No. 4 and includes the exon 1 region characteristic of the MeCP2E1 protein. As with the nucleic acid molecules of the invention, identity is calculated according to methods known in the art. Sequence identity is most preferably assessed by the algorithm of BLAST version 2.1 advanced search. BLAST is a series of programs that are available online at www.ncbi.nlm.nih.gov/BLAST. The advanced BLAST search (www.ncbi.nlm.nih.gov/blast/blast.cgi?J-form=1) is set to default parameters (i.e. Matrix BLOSUM62, Gap existence cost 11; Per residue gap cost 1; Lambda ration 0.85 default).

The invention also contemplates isoforms of the proteins of the invention. An isoform contains the same number and kinds of amino acids as a protein of the invention, but the isoform has a different molecular structure. The isoforms contemplated by the present invention are those having the same properties as a protein of the invention as described herein.

The present invention also includes a protein of the invention conjugated with a selected protein, or a selectable marker protein (see below) to produce fusion proteins. Additionally, immunogenic portions of a protein of the invention are within the scope of the invention.

The proteins of the invention (including truncations, analogs, etc.) may be prepared using recombinant DNA methods. Accordingly, the nucleic acid molecules of the present invention having a sequence which encodes a protein of the invention may be incorporated in a known manner into an appropriate expression vector which ensures good expression of the protein. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

The invention further provides a recombinant expression vector comprising a DNA nucleic acid molecule of the invention cloned into the expression vector in an antisense orientation. That is, the DNA molecule is operatively linked to a regulatory sequence in a manner which allows for expression, by transcription of the DNA molecule, of an RNA molecule which is antisense to a nucleotide sequence comprising the nucleotides as shown SEQ ID No. 3. Regulatory sequences operatively linked to the antisense nucleic acid can be chosen which direct the continuous expression of the antisense RNA molecule.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of a target recombinant protein by acting as a ligand in affinity purification. For example, a proteolytic cleavage site may be added to the target recombinant protein to allow separation of the recombinant protein from the fusion moiety subsequent to purification of the fusion protein.

Recombinant expression vectors can be introduced into host cells to produce a transformed host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as *E. coli*, insect cells (using baculovirus), yeast cells or mammalian cells. Other suitable host cells can be found in Goeddel, Gene Expression Technology: Methods in Enzymology 185, Academic Press, San Diego, Calif. (1991).

The proteins of the invention may also be prepared by chemical synthesis using techniques well known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart).

III. Applications

A. Diagnostic Applications

As previously mentioned, the present inventors have isolated a novel splice variant of the MECP2 gene, MECP2E1, and have shown that exon 1 is deleted or mutated in people with neuropsychiatric disorders or developmental disorders such as Rett's syndrome or mental retardation. As a result, the present invention also includes a method of detecting a neuropsychiatric or developmental disorder by detecting a mutation or deletion in the MECP2E1 nucleic acid or MeCP2E1 protein.

The term "neuropsychiatric disorder" as used herein includes, but is not limited to, autism/autism spectrum disorder, epilepsy, Angelman syndrome, Prader-Willi syndrome, encephalopathy, schizophrenia, bipolar affective disorder, depression, obsessive compulsive disorder, panic disorder, attention deficit hyperactivity disorder, and ataxia.

The term "developmental disorder" includes but is not limited to, mental retardation.

i) Detecting Mutations in the Nucleic Acid Sequence

In one embodiment, the present invention provides a method for detecting a neuropsychiatric or developmental disorder comprising detecting a deletion or mutation in exon 1 of the MECP2 gene in a sample obtained from an animal, preferably a mammal, more preferably a human.

The Examples and Table 1 summarize some of the mutations found in MECP2E1 in patient's with Rett's syndrome or developmental delay. (They are also described in Section I). Screening assays can be developed for each of the mutations. Examples of methods that can be used to detect mutations include sequencing, polymerase chain reaction, reverse transcription-polymerase chain reaction, denaturing HPLC, electrophoretic mobility, nucleic acid hybridization, fluorescent in situ hybridization and multiplex ligation-dependent probe amplification. Details of screening assays that may be employed are provided in Examples 3, 4 or 5.

Rett's syndrome has been shown to be caused by deletions in exon 1 of MECP2. Patients homozygous for these deletions can be detected by PCR-amplifying and sequencing exon 1 and flanking sequences using X1F/X1R primers. Consequently, the present invention includes a method for determining a deletion in exon 1 of the MECP2 gene by a method comprising:

(a) amplifying the nucleic acid sequences in the sample with primers X1F (5'-CCATCACAGCCAATGACG-3') (SEQ ID No. 19) and X1R (5'-AGGGGGAGGGTAGA-GAGGAG-3') (SEQ ID No. 20) in a polymerase chain reaction;

(b) amplifying the nucleic acid sequences from a control with same primers;

(c) sequencing the amplified sequences; and (d) comparing the sample sequences to the control sequences wherein deletion of nucleotides in the sample sequence compared to the control sequence indicates that the sample is from an animal with Rett's syndrome.

Additional exon 1 mutations not detectable by the PCR reaction, can be identified using multiplex ligation-dependent probe amplification (MLPA) in all four exons. MLPA analysis is described in reference 5 and in Schouten, U.S. application Ser. No. 10/218,567, (publication number 2003/0108913) which are incorporated herein in by reference. Accordingly, the present invention includes a method for determining a deletion in exon 1 of the MECP2 gene by performing MLPA analysis with 20 probe pairs that target the four MECP2 exons, six X-linked control regions and ten autosomal control regions.

One skilled in the art will appreciate that other methods, in addition to the ones discussed above and in the examples, can be used to detect mutations in exon 1 of the MECP2 gene. For example, in order to isolate nucleic acids from a sample, one can prepare nucleotide probes from the nucleic acid sequences of the invention. In addition, the nucleic acid probes described herein (for example, see FIG. 1) can also be used. A nucleotide probe may be labelled with a detectable marker such as a radioactive label which provides for an adequate signal and has sufficient half life such as $^{32}P$, $^3H$, $^{14}C$ or the like. Other detectable markers which may be used include antigens that are recognized by a specific labelled antibody, fluorescent compounds, enzymes, antibodies specific for a labelled antigen, and chemiluminescent compounds. An appropriate label may be selected having regard to the rate of hybridization and binding of the probe to the nucleotide to be detected and the amount of nucleotide available for hybridization.

Accordingly, the present invention also relates to a method of detecting the presence of a nucleic acid molecule containing exon 1 of the MECP2 gene in a sample comprising contacting the sample under hybridization conditions with one or more of nucleotide probes which hybridize to the nucleic acid molecules and are labelled with a detectable marker, and determining the degree of hybridization between the nucleic acid molecule in the sample and the nucleotide probes.

Hybridization conditions which may be used in the methods of the invention are known in the art and are described for example in Sambrook J, Fritch E F, Maniatis T. In: Molecular Cloning, A Laboratory Manual, 1989. (Nolan C, Ed.), Cold Spring Harbor Laboratory Press, Cold Spring Harbor, N.Y. The hybridization product may be assayed using techniques known in the art. The nucleotide probe may be labelled with a detectable marker as described herein and the hybridization product may be assayed by detecting the detectable marker or the detectable change produced by the detectable marker.

Prior to hybridizing a sample with DNA probes, the sample can be treated with primers that flank the MECP2 gene in order to amplify the nucleic acid sequences in the sample. The primers used may be the ones described in the present application. For example, primers specific for human MECP2 include HF(ctcggagagagggctgtg) (SEQ ID No. 5), HR1(cttgaggggtttgtccttga) (SEQ ID No. 6), HR2(cgtttgat-caccatgacctg) (SEQ ID No. 7). Primers for mouse MECP2 include MF(aggaggcgaggaggagagac) (SEQ ID NO. 8) and MR(ctggctctgcagaatggtg) (SEQ ID No. 9). In addition, the sequence of the MECP2 gene provided herein also permits the identification and isolation, or synthesis of new nucleotide sequences which may be used as primers to amplify a nucleic acid molecule of the invention. The primers may be used to amplify the genomic DNA of other species. The PCR amplified sequences can be examined to determine the relationship between the genes of various species.

The length and bases of the primers for use in the PCR are selected so that they will hybridize to different strands of the desired sequence and at relative positions along the sequence such that an extension product synthesized from one primer when it is separated from its template can serve as a template for extension of the other primer into a nucleic acid of defined length. Primers which may be used in the invention are oligonucleotides i.e. molecules containing two or more deoxyribonucleotides of the nucleic acid molecule of the invention which occur naturally as in a purified restriction endonuclease digest or are produced synthetically using techniques known in the art such as for example phosphotriester and phosphodiester methods (See Good et al Nucl. Acid Res 4:2157, 1977) or automated techniques (See for example, Conolly, B. A. Nucleic Acids Res. 15(7): 3131, 1987). The primers are capable of acting as a point of initiation of synthesis when placed under conditions which permit the synthesis of a primer extension product which is complementary to the DNA sequence of the invention i.e. in the presence of nucleotide substrates, an agent for polymerization such as DNA polymerase and at suitable temperature and pH. Preferably, the primers are sequences that do not form secondary structures by base pairing with other copies of the primer or sequences that form a hair pin configuration. The primer preferably contains between about 7 and 25 nucleotides.

The primers may be labelled with detectable markers which allow for detection of the amplified products. Suitable detectable markers are radioactive markers such as P-32, S-35, I-125, and H-3, luminescent markers such as chemiluminescent markers, preferably luminol, and fluorescent markers, preferably dansyl chloride, fluorescein-5-isothiocyanate, and 4-fluor-7-nitrobenz-2-axa-1,3 diazole, enzyme markers such as horseradish peroxidase, alkaline phosphatase, β-galactosidase, acetylcholinesterase, or biotin.

It will be appreciated that the primers may contain non-complementary sequences provided that a sufficient amount of the primer contains a sequence which is complementary to a nucleic acid molecule of the invention or oligonucleotide fragment thereof, which is to be amplified. Restriction site linkers may also be incorporated into the primers allowing for digestion of the amplified products with the appropriate restriction enzymes facilitating cloning and sequencing of the amplified product.

In an embodiment of the invention a method of determining the presence of a nucleic acid molecule of the invention is provided comprising treating the sample with primers which are capable of amplifying the nucleic acid molecule or a predetermined oligonucleotide fragment thereof in a polymerase chain reaction to form amplified sequences, under conditions which permit the formation of amplified sequences and, assaying for amplified sequences.

The polymerase chain reaction refers to a process for amplifying a target nucleic acid sequence as generally described in Innis et al, Academic Press, 1990 in Mullis el al., U.S. Pat. No. 4,863,195 and Mullis, U.S. Pat. No. 4,683,202 which are incorporated herein by reference. Conditions for amplifying a nucleic acid template are described in M. A. Innis and D. H. Gelfand, PCR Protocols, A Guide to Methods and Applications M. A. Innis, D. H. Gelfand, J. J. Sninsky and T. J. White eds, pp 3-12, Academic Press 1989, which is also incorporated herein by reference.

The amplified products can be isolated and distinguished based on their respective sizes using techniques known in the art. For example, after amplification, the DNA sample can be separated on an agarose gel and visualized, after staining with ethidium bromide, under ultra violet (UV) light. DNA may be amplified to a desired level and a further extension reaction may be performed to incorporate nucleotide derivatives having detectable markers such as radioactive labelled or biotin labelled nucleoside triphosphates. The primers may also be labelled with detectable markers as discussed above. The detectable markers may be analyzed by restriction and electrophoretic separation or other techniques known in the art.

The conditions which may be employed in the methods of the invention using PCR are those which permit hybridization and amplification reactions to proceed in the presence of DNA in a sample and appropriate complementary hybridization primers. Conditions suitable for the polymerase chain reaction are generally known in the art. For example, see M. A. Innis and D. H. Gelfand, PCR Protocols, A guide to Methods and Applications M. A. Innis, D. H. Gelfand, J. J. Sninsky and T. J. White eds, pp3-12, Academic Press 1989, which is incorporated herein by reference. Preferably, the PCR utilizes polymerase obtained from the thermophilic bacterium *Thermus aquatics* (Taq polymerase, GeneAmp Kit, Perkin Elmer Cetus) or other thermostable polymerase may be used to amplify DNA template strands.

It will be appreciated that other techniques such as the Ligase Chain Reaction (LCR) and NASBA may be used to amplify a nucleic acid molecule of the invention (Barney in "PCR Methods and Applications", August 1991, Vol. 1(1), page 5, and European Published Application No. 0320308, published Jun. 14, 1989, and U.S. Pat. No. 5,130,238 to Malek).

(ii) Detecting the MeCP2E1 Protein

In another embodiment, the present invention provides a method for detecting a neuropsychiatric or developmental disorder comprising detecting a deletion or mutation in the MeCP2E1 protein in a sample from an animal.

The MeCP2E1 protein of the present invention may be detected in a biological sample using antibodies that are specific for MeCP2E1 using various immunoassays that are discussed below.

Conventional methods can be used to prepare the antibodies. For example, by using a peptide from the MeCP2E1 protein of the invention, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77-96), and screening of combinatorial antibody libraries (Huse et al., Science 246, 1275 (1989)). Hybridoma cells can be screened immunochemically for production of antibodies specifically reactive with the peptide and the monoclonal antibodies can be isolated. Therefore, the invention also contemplates hybridoma cells secreting monoclonal antibodies with specificity for a protein of the invention.

The term "antibody" as used herein is intended to include fragments thereof which also specifically react with a protein of the invention, or peptide thereof. Antibodies can be fragmented using conventional techniques and the fragments screened for utility in the same manner as described above. For example, F(ab')$_2$ fragments can be generated by treating antibody with pepsin. The resulting F(ab')$_2$ fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes a CipA protein (See, for example, Morrison et al., Proc. Natl. Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Monoclonal or chimeric antibodies specifically reactive with a protein of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, reactive against a protein of the invention may also be generated by screening expression libraries encoding immunoglobulin genes, or portions thereof, expressed in bacteria with peptides produced from the nucleic acid molecules of the present invention. For example, complete Fab fragments, VH regions and FV regions can be expressed in bacteria using phage expression libraries (See for example Ward et al., Nature 341, 544-546: (1989); Huse et al., Science 246, 1275-1281 (1989); and McCafferty et al. Nature 348, 552-554 (1990)).

Antibodies may also be prepared using DNA immunization. For example, an expression vector containing a nucleic acid of the invention (as described above) may be injected into a suitable animal such as mouse. The protein of the invention will therefore be expressed in vivo and antibodies will be induced. The antibodies can be isolated and prepared as described above for protein immunization.

The antibodies may be labelled with a detectable marker including various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include S-35, Cu-64, Ga-67, Zr-89, Ru-97, Tc-99m, Rh-105, Pd-109, In-111, I-123, I-125, I131, Re-186, Au-198, Au-199, Pb-203, At-211, Pb-212 and Bi-212. The antibodies may also be labelled or conjugated to one partner of a ligand binding pair. Representative examples include avidin-biotin and riboflavin-riboflavin binding protein. Methods for conjugating or labelling the antibodies discussed above with the representative labels set forth above may be readily accomplished using conventional techniques.

The antibodies reactive against proteins of the invention (e.g. enzyme conjugates or labelled derivatives) may be used to detect a protein of the invention in various samples, for example they may be used in any known immunoassays which rely on the binding interaction between an antigenic determinant of a protein of the invention and the antibodies. Examples of such assays are radioimmunoassays, enzyme immunoassays (e.g. ELISA), immunofluorescence, immuno-precipitation, latex agglutination, hemagglutination, and histochemical tests. Thus, the antibodies may be used to identify or quantify the amount of a protein of the invention in a sample in order to diagnose the presence of Rett's syndrome.

In a method of the invention a predetermined amount of a sample or concentrated sample is mixed with antibody or labelled antibody. The amount of antibody used in the process is dependent upon the labelling agent chosen. The resulting protein bound to antibody or labelled antibody may be isolated by conventional isolation techniques, for example, salting out, chromatography, electrophoresis, gel filtration, fractionation, absorption, polyacrylamide gel electrophoresis, agglutination, or combinations thereof.

The sample or antibody may be insolubilized, for example, the sample or antibody can be reacted using known methods with a suitable carrier. Examples of suitable carriers are Sepharose or agarose beads. When an insolubilized sample or antibody is used protein bound to antibody or unreacted antibody is isolated by washing. For example, when the sample is blotted onto a nitrocellulose membrane, the antibody bound to a protein of the invention is separated from the unreacted antibody by washing with a buffer, for example, phosphate buffered saline (PBS) with bovine serum albumin (BSA).

When labelled antibody is used, the presence of MeCP2E1 can be determined by measuring the amount of labelled antibody bound to a protein of the invention in the sample or of the unreacted labelled antibody. The appropriate method of measuring the labelled material is dependent upon the labelling agent.

When unlabelled antibody is used in the method of the invention, the presence of MeCP2E1 can be determined by measuring the amount of antibody bound to the protein using substances that interact specifically with the antibody to cause agglutination or precipitation. In particular, labelled antibody against an antibody specific for a protein of the invention, can be added to the reaction mixture. The presence of a protein of the invention can be determined by a suitable method from among the already described techniques depending on the type of labelling agent. The antibody against an antibody specific for a protein of the invention can be prepared and labelled by conventional procedures known in the art which have been described herein. The antibody against an antibody specific for a protein of the invention may be a species specific anti-immunoglobulin antibody or monoclonal antibody, for example, goat anti-rabbit antibody may be used to detect rabbit antibody specific for a protein of the invention.

(iii) Kits

The reagents suitable for carrying out the methods of the invention may be packaged into convenient kits providing the necessary materials, packaged into suitable containers. Such kits may include all the reagents required to detect a nucleic acid molecule or protein of the invention in a sample by means of the methods described herein, and optionally suitable supports useful in performing the methods of the invention.

In one embodiment of the invention, the kit includes primers which are capable of amplifying a nucleic acid molecule of the invention or a predetermined oligonucleotide fragment thereof, all the reagents required to produce the amplified nucleic acid molecule or predetermined fragment thereof in the polymerase chain reaction, and means for assaying the amplified sequences. The kit may also include restriction enzymes to digest the PCR products. In another embodiment of the invention the kit contains a nucleotide probe which hybridizes with a nucleic acid molecule of the invention, reagents required for hybridization of the nucleotide probe with the nucleic acid molecule, and directions for its use. In a further embodiment of the invention the kit includes antibodies of the invention and reagents required for binding of the antibody to a protein of the invention in a sample.

The kits may include nucleic acid molecules, proteins or antibodies of the invention (described above) to detect or treat neuropsychiatric disorders and developmental disorders together with instructions for the use thereof.

The methods and kits of the present invention may be used to detect neuropsychiatric and developmental disorders such as Rett's syndrome and mental retardation. Samples which may be tested include bodily materials such as blood, urine, serum, tears, saliva, feces, tissues, organs, cells and the like. In addition to human samples, samples may be taken from mammals such as non-human primates, etc.

Before testing a sample in accordance with the methods described herein, the sample may be concentrated using techniques known in the art, such as centrifugation and filtration. For the hybridization and/or PCR-based methods described herein, nucleic acids may be extracted from cell extracts of the test sample using techniques known in the art.

B. Therapeutic Applications

As mentioned previously, the nucleic acid molecules of the present invention are deleted or mutated in people with neuropsychiatric disorders and developmental disorders. Accordingly, the present invention provides a method of treating or preventing neuropsychiatric disorders and developmental disorders by administering a nucleic acid sequence containing a sufficient portion of the MECP2E1 splice variant to treat or prevent neuropsychiatric disorders and developmental disorders. The present invention includes a use of a nucleic acid molecule or protein of the invention to treat or detect neuropsychiatric disorders and developmental disorders.

Recombinant molecules comprising a nucleic acid sequence or fragment thereof, may be directly introduced into cells or tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes. Recombinant molecules may also be delivered in the form of an aerosol or by lavage.

The nucleic acid sequences may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regima may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

C. Experimental Models

The present invention also includes methods and experimental models for studying the function of the MECP2 gene and MeCP2E1 protein. Cells, tissues and non-human animals that lack the MECP2E1 splice variant or partially lack in MeCP2E1 expression may be developed using recombinant expression vectors having a specific deletion or mutation in the MECP2E1 gene. A recombinant expression vector may be used to inactivate or alter the MECP2 gene by homologous recombination and thereby create a MECP2E1 deficient cell, tissue or animal. In particular, a targeted mutation could be designed to result in deficient MECP2E1 while MECP2E2 remains unaltered. This can be accomplished by targeting exon 1 of the MECP2 gene.

Null alleles may be generated in cells, such as embryonic stem cells by deletion mutation. A recombinant MECP2 gene may also be engineered to contain an insertion mutation which inactivates MECP2E1. Such a construct may then be introduced into a cell, such as an embryonic stem cell, by a technique such as transfection, electroporation, injection etc. Cells lacking an intact MECP2 gene may then be identified, for example by Southern blotting, Northern Blotting or by assaying for MECP2E1 using the methods described herein. Such cells may then be fused to embryonic stem cells to generate transgenic non-human animals deficient in MECP2E1. Germline transmission of the mutation may be achieved, for example, by aggregating the embryonic stem cells with early stage embryos, such as 8 cell embryos, in vitro; transferring the resulting blastocysts into recipient females and; generating germline transmission of the resulting aggregation chimeras. Such a mutant animal may be used to define specific cell populations, developmental patterns and in vivo processes, normally dependent on MECP2E1 expression. The present invention also includes the preparation of tissue specific knock-outs of the MECP2E1 variant.

The following non-limiting examples are illustrative of the present invention:

EXAMPLES

Example 1

Identification of MEC2E1 Splice Variant

Inspection of the 5'UTR revealed that, whereas exon 2 has a number of in-frame stops upstream of the ATG, exon 1 contains an open reading frame across its entire length including an ATG. Submitting a theoretical construct composed of exons 1, 3 and 4 to the ATGpr program (www.hri.co.jp/atgpr/), which predicts the likelihood of an ATG to be an initiation codon based on significance of its surrounding Kozak nucleotide context, returned a reliability score of 97% compared to 64% for MECP2E2. A search in EST databases identified eight examples of our theorized transcript (named MECP2E1) (FIG. 1*b*) (vs. 14 examples of MECP2E2). MECP2E1 would be predicted to encode a new variant, MeCP2E1, with an alternative longer N-terminus determined by exon 1.

Example 2

Expression of MECP2E1

Figure 1C:
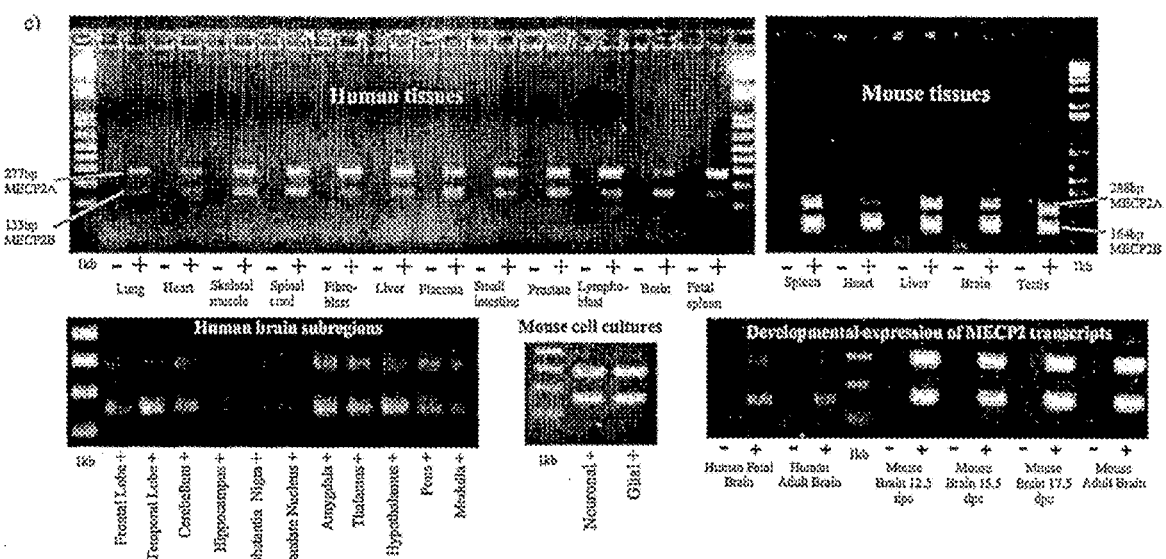
Figure 1D:
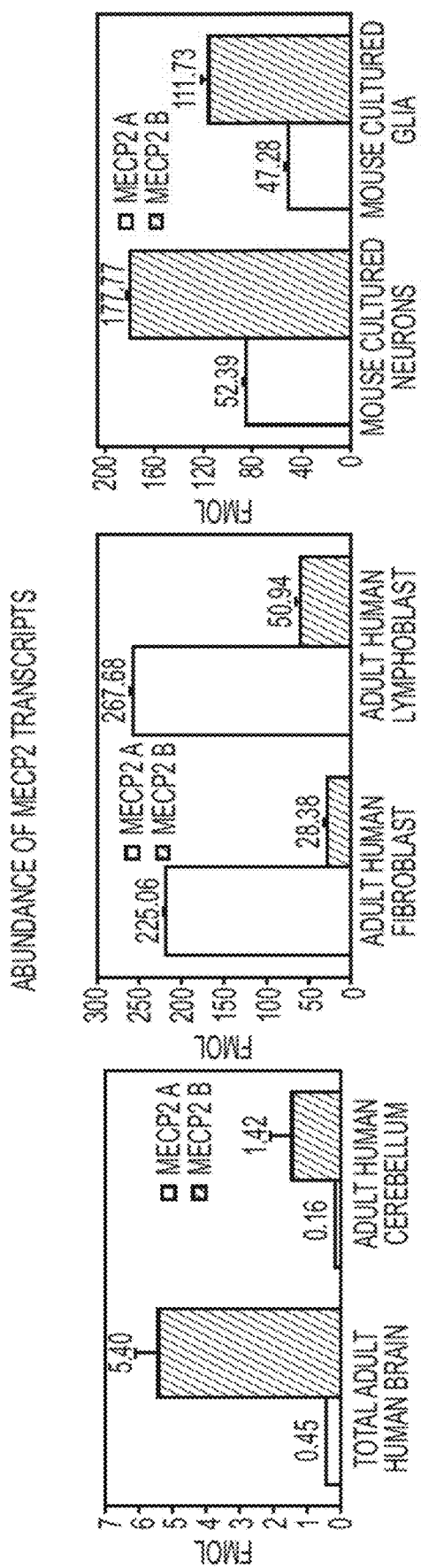
Figure 1E:
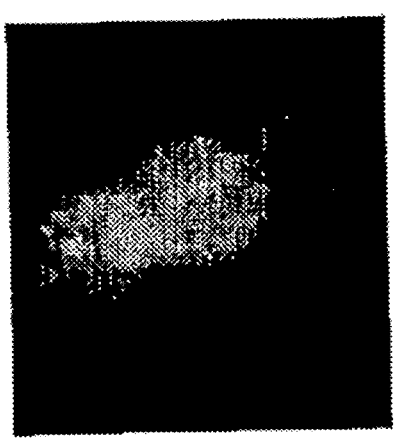
Figure 1E:
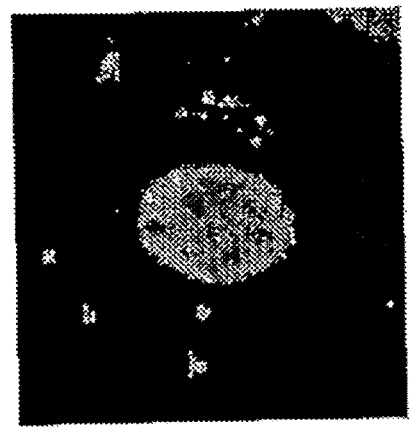

To confirm that MECP2E1 is in fact expressed and not an artifact of cDNA library preparations, cDNA from a variety of tissues was PCR-amplified using a 5'-primer in exon 1 and a 3'-primer in exon 3 (FIG. 1*a*). Two PCR products corresponding to MECP2E2 and MECP2E1 by size and sequence were obtained in all tissues, including fetal and adult brain, and in brain subregions (FIG. 1c). Results in mouse were similar (FIG. 1c). The expression levels of the two transcripts in adult human brain were quantified. MECP2E1 expression is 10 times higher than MECP2E2 (FIG. 1d). The subcellular localization of MeCP2E1 following transfection of 3' myc-tagged MECP2E1 into COS-7 cells was found to be principally in the nucleus (FIG. 1e).

MECP2E1 was not detected in previous expression studies. Northern analyses reveal three transcripts, 1.9, 5 and 10.1 kb, with the differences in size due to alternative polyadenylation signal usage (4,6,8) (FIG. 1a). MECP2E1 differs from MECP2E2 in lacking the 124-nucleotide exon 2. At the 5 and 10.1 kb positions on the gel, the two transcripts would not be separable. In the 1.9 kb range, published northern blots do show a thick or double band likely corresponding to the two transcripts. Likewise, conventional western blot analysis would not allow resolution of the two MeCP2 isoforms (molecular weight difference <0.9 kD; FIG. 1f).

Example 3

Mutations in MECP2E1 in Rett's Syndrome

Figure 2A:
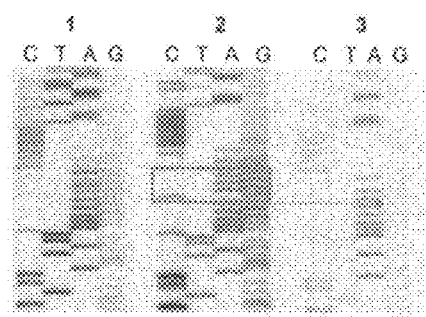
FIGS. 2A-2C shows a deletion mutation in patient V1. a1) Sequence of PCR product from genomic DNA using primers X1F/X1R (FIG. 1a). Note mixed sequence. a2) and a3) Sequences of clones of the patient's wild-type and mutant alleles respectively; red box indicating the 11 nucleotides deleted in the mutated allele. b) Electropherograms of the same cloned wild-type and deleted alleles (SEQ ID NOS 43-46, respectively, in order of appearance). c) PCR on indicated cDNAs using primers HF/HR1 (FIG. 1a,c). Lanes 1 and 2 (on 2.5% high resolution agarose) are from control and patient whole blood respectively. Lanes 3 to 8 (on 6% denaturing polyacrylamide) are from control blood (3), patient blood (4), control fetal brain (5), control adult brain (6), control testis (7) and control genomic DNA (8). Note that expression of the patient's MECP2E2 transcript with the 1 lbp exon 1 deletion (band at 266 bp) is not diminished compared to the non-deleted allele (277 bp). The 141 and 152 bp bands are the deleted and non-deleted MECP2E1 transcripts respectively.
Figure 2B:
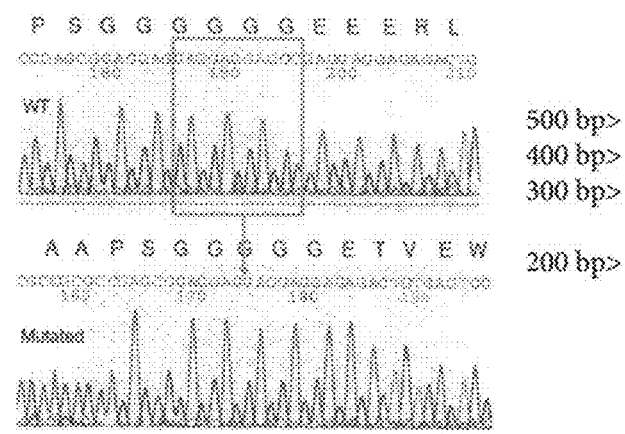

To determine whether the new coding region is mutated in Rett's syndrome, Exon 1 and flanking sequences were PCR-amplified and sequenced in 19 girls with typical RTT in whom no mutations had been found in the other exons. One patient (V1) was found to carry an 11 bp deletion mutation in exon 1 (FIG. 2). The deletion occurs within the predicted exon 1 open reading frame of MECP2E1 and leads to a frame shift that results in a missense amino acid sequence followed by a premature stop codon after amino acid 36. It does not affect the coding sequence of MECP2E2. This sequence change was not found in 200 control individuals including the patient's parents and brother.

Figures 3A, 3B:
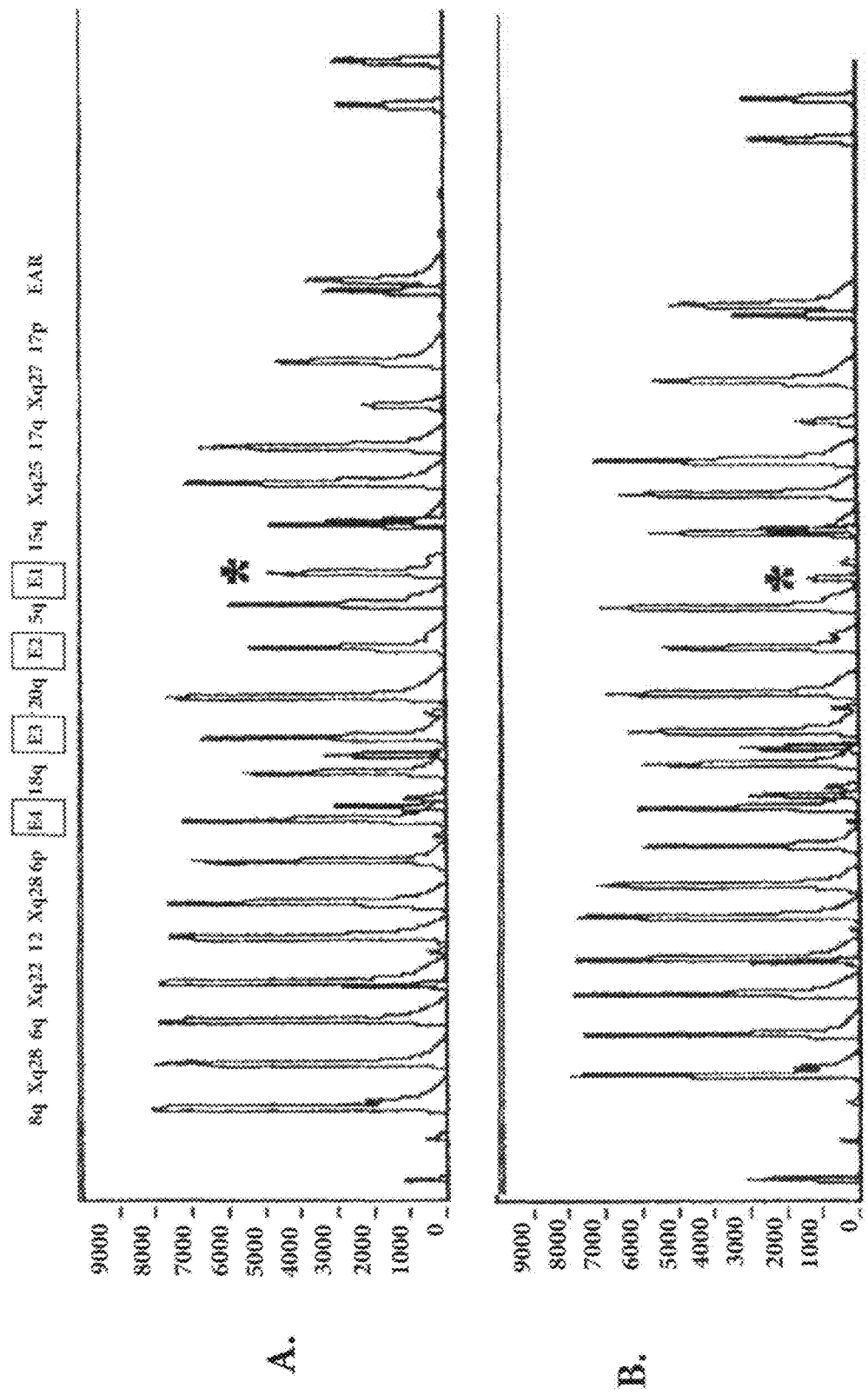
FIGS. 3A-3B shows a deletion mutation in patient V2. MECP2 Multiplex ligation-dependent probe amplification (MLPA) peak profiles are shown. Control loci are listed along the top. Boxed regions (E1-E4) indicate MECP2 exons 1-4. a) MLPA profile of normal control. b) MLPA profile of patient V2 shows a hemizygous exon 1 deletion (asterisk). The result was consistently reproducible and sequencing ruled out the possibility of a SNP interfering with the ligation efficiency of the MLPA reaction.

To search, in the remaining patients, for additional exon 1 deletions not detectable by our PCR reaction, multiplex ligation-dependent probe amplification (MLPA) (5) was performed in all four exons and detected a hemizygous deletion of exon 1 in one patient (Patient V2; FIG. 3). Finally, an additional patient with an MLPA-detected deletion restricted to exon 1 was recently documented in abstract form, though the effect on MECP2E1 was not realized (S. Boulanger et al. *Am J Hum Genet* 73, 572 (2003)).

In contrast, no mutation specific to the MeCP2E2-defining exon 2 has been found to date despite several hundred patients analyzed for mutations in this exon (31 publications; most reviewed in ref 3). These studies did not include exon 1 as it was considered non-coding.

Figure 2C:
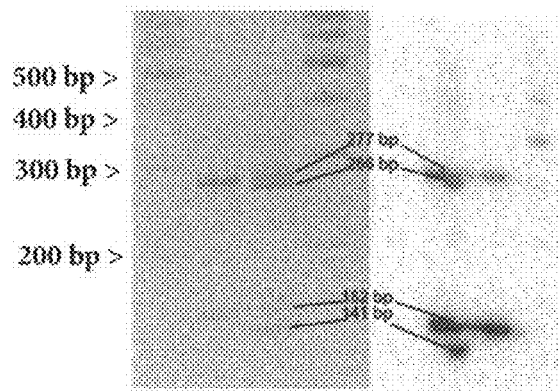

Exon 1 deletions result in absent or truncated MeCP2E1 proteins. However, they also result in shortening of MECP2E2's 5'UTR and may possibly affect its expression. This possibility was tested in patient V1 by RT-PCR on whole blood. No diminution of MECP2E2 expression was present (FIG. 2c). In conclusion, mutation data indicate that inactivation of MeCP2E1 is sufficient in RTT, but the same cannot be said, to date, of MeCP2E2.

Materials and Methods

PCR, manual sequencing, cloning, rtPCR, gel blotting. PCR amplification was performed using $[NH_4]_2SO_4$-containing PCR buffer (MBI Fermentas) with 1M betaine, 200 µM dNTPs including 50% deaza dGTP, with a 95° C. denaturing step for 3 minutes, followed by cycling at 95° C. for 30 secs, 55° C. for 30 secs, 72° C. for 45 secs for 30 cycles, followed by a 7 minute soak step at 72° C. Manual sequencing was performed, following extraction from a 1% agarose gel, using the Thermosequenase™ kit (USB/Amersham) and run on a 6% denaturing polyacrylamide gel for 3 hours. PCR products were cloned using the pDRIVE vector (Qiagen PCR cloning kit). Whole blood RNA was extracted using the PAXgene Blood RNA Kit (Qiagen). Reverse transcription was performed with random hexamers and a standard Superscript III protocol (Invitrogen). Human brain subregion cDNA was obtained from OriGene. The polyacrylamide gel in (FIG. 2c) was blotted onto Hybond N+ (Amersham) and hybridized with primer HF labeled at the 3'end with $[\alpha^{32}P]$-dCTP using deoxynucleotidyl transferase (MBI Fermentas).

Figures 4A, 4B:
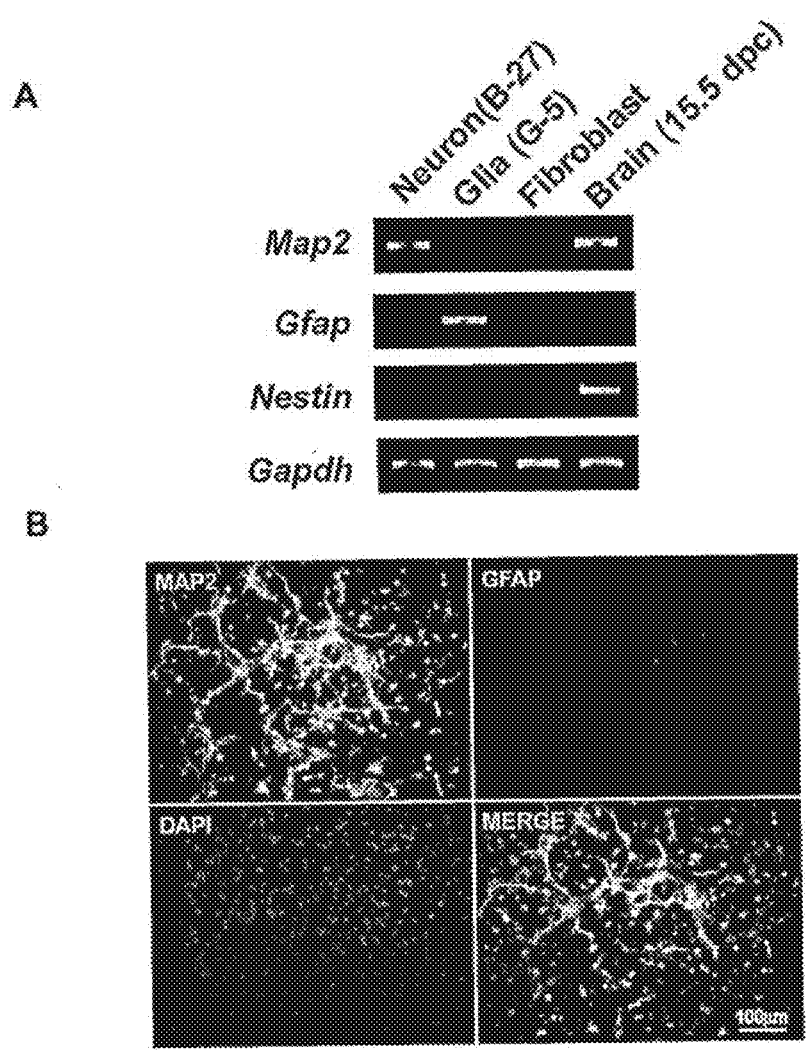
FIGS. 4A-4B shows the characterization of the primary brain cell cultures by rtPCRR (A) and IF (B). (A) Map2, Gfap and Nestin expressions indicate that the cultures in B-27 medium were composed primarily of neurons and those in G-5 medium were glial cells. Fibroblasts from the same embryos were also cultured and used as negative controls. Whole brain tissue (15.5 dpc) was used as a positive control for Map2 and Nestin. (B) Double staining for neurons was performed with mouse anti-MAP2 and rabbit anti-GFAP antibodies. They were also counterstained with DAPI (blue). Most of the cells are neurons, which stained positively for MAP2 (green), and an insignificant percentage of contamination with glial cells stained positively for GFAP (red) was detected.

Preparation of neuronal and glial cultures. Cerebral cortices were prepared from 15.5 days postcoitum (15.5 dpc) embryos of CD-1 mice. The procedure of Yamasaki et al. (Yamasaki et al. Hum Mol Genet 12: 837-847, 2003) was used. Briefly, fetal cerebral cortices without meninges were dissociated by mechanical trituration and digested with 0.25% trypsin with EDTA. After adding fetal bovine serum (FBS; GIBCO BRL), filtered cells were collected by centrifugation. The cell pellet was resuspended in Neurobasal (GIBCO BRL) medium supplemented with B-27 (GIBCO BRL) for growth of neurons or with G-5 (GIBCO BRL) for growth of glial cells. Cells were plated on polyethyleneimine-coated plastic dishes at a density of $2\times10^6$ cells/ml. Cultures of neurons and glial cells were maintained in 5% $CO_2$ at 37° C. for 6 days and 12 days, respectively. Isolated brain cells were characterized by RT-PCR and immunofluorescence (IF) using the markers MAP2 (microtubule-associated protein 2) for neurons, GFAP (glial fibrillary acidic protein) for glial cells and NESTIN for progenitor cells. For IF, the following specific antibodies were used: mouse monoclonal anti-MAP2 (CHEMICON), and rabbit polyclonal anti-GFAP (DAKO). The primers used for rtPCR were same as Yamasaki et al. To obtain a semi-quantitative PCR, optimal cDNA concentration and number of cycles were determined according to Gapdh amplification as an internal control. FIG. 4 shows the characterization of the primary brain cell cultures by rtPCR (A) and IF (B).

Quantitative rtPCR. To determine the quantity of the MECP2 transcripts in different tissues, we developed transcript-specific real-time quantitative PCR assays using SYBR Green detection method (PE Applied Biosystems, ABI PRISM 7900 Sequence Detection System). The following MECP2E2-specific forward primer (25 nM) (in exon 2) was designed: 5'-ctcaccagttcctgctttgatgt-3' (SEQ ID No. 12). The MECP2E1-specific primer (25 nM) was placed at the junction of exons 1 and 3: 5'-aggagagactggaagaaaagtc-3' (SEQ ID No. 10). Both assays used the same reverse primer (25 nM) in exon 3: 5'-cttgaggggtttgtccttga-3' (SEQ ID No. 11), producing fragments of 161- (MECP2E2) and 65-bp (MECP2E1). The corresponding transcript-specific primers (25 nM) for the mouse mecp2 transcripts (mecp2e2 167 bp and mecp2e1 71 bp) were 5'-ctcaccagttcctgctttgatgt-3' (SEQ ID No. 12) (MECP2E2); 5'-aggagagactggaggaaaagtc-3' (SEQ ID No. 13) (MECP2E1) and the common reverse primer 5'-cttaaacttcagtggcttgtctctg-3' (SEQ ID No. 14). PCR conditions were: 2 min 50 C, 10 min 95 C and 40 cycles of 15 sec 95 C, 85 s 60 C. The PCR reactions were performed in separate tubes; and absolute quantitation of the MECP2E2 and E1 transcripts was performed from cDNA from human adult brain, cerebellum, fibroblast and lymphoblast (Clontech, Palo Alto, USA), as well as from murine neuronal and glial cell cultures (see above). Results were analyzed using the standard curve method according to the manufacturer's instructions (PE Applied Biosystems, ABI PRISM 7900

Sequence Detection System). The standard curve was developed using dilutions of the transcript-specific purified PCR products.

Immunofluorescence light microscopy. 3'-myc-tagged MECP2E2 and MECP2E1 constructs (pCDNA3.1A-MECP2E2-myc and pcDNA3.1A-MECP2E1-myc) were generated by PCR amplification of full-length cDNA of each transcript with BamHI (5') and XbaI (3') restriction sites attached and subsequent cloning in-frame with myc into pcDNA3.1 version A (Invitrogen). The forward primer for MECP2E2 contained the start codon in exon 2 (5'-tatggatccATGgtagctgggat-3') (SEQ ID No. 15), while the forward primer for MECP2E1 included the start codon in exon1 (5'-tatggatccggaaaATGgccg-3') (SEQ ID No. 16) (BamHI restriction site underlined, start codon uppercase). The reverse primer was the same for both amplifications (5'-gcgtctagagctaactctct-3') (SEQ ID No. 17) (XbaI restriction site underlined). The template used for PCR was small intestine cDNA for MECP2E2 and skeletal muscle cDNA for MECP2E1. pcDNA3.1A-MECP2E2-myc and pcDNA3.1A-MECP2E1-myc (2 ug) were transfected into COS-7 cells using lipofectamine (Invitrogen) and the lipid-DNA complex was exposed in DMEM (GIBCO) for 5 hours. Forty-eight hours post-transfection the cultures were rinsed in PBS and fixed for 15 min at −20° C. in an acetone:methanol (1:1) mix, blocked for 1 hour (10% BSA in PBS) and incubated with anti-myc (Santa Cruz Biotechnology, 1:50 in blocking buffer) for 45 min at room temperature. After washing with PBS, slides were incubated with secondary antibody (FITC-labeled goat anti-mouse (Jackson Immunoresearch labs), 1:400, detectable through the green filter) in blocking solution, mounted with Dako Anti-Fade and analyzed by immunofluorescence light microscopy.

MLPA analysis. MLPA was performed as described by Schouten et al., supra and as described by Schouten, supra. MECP2 test kits from MRC-Holland, Amsterdam, Netherlands (www.mrc-holland.com) were utilized and consisted of 20 probe pairs that target the four MECP2 exons, six X-linked control regions and ten autosomal control regions. Briefly, 100-200 ng of genomic DNA was denatured and hybridized with the probe mix overnight at 60° C. The following morning the paired probes were ligated using heat stable Ligase-65 at 54° C. for 15 minutes. The ligation was followed with PCR with a common primer pair that hybridizes to the terminal end of each ligation product. One PCR primer was FAM-labeled and conditions for the PCR were as follows: 95° C. 30 s, 60° C. 30 s and 72° C. 1 min. The resulting amplicons were analyzed on an ABI 3100 capillary electrophoresis instrument and ABI Genescan software. All data management and comparisons to normal controls were done with Excel software.

Discussion

Recently, studies in frog (*Xenopus laevis*) afforded important insight into the role of MeCP2 in neurodevelopmental transcription regulation. MeCP2 was shown to be a component of the SMRT complex involved in the regulation of genes involved in neuronal differentiation following developmental stage-specific mediation by Notch-Delta. The frog Mecp2 transcript targeted for silencing in these experiments is an orthologue of MECP2E1 (FIG. 1*f*). In fact, MeCP2E1 appears to be the only form of MeCP2 in non-mammalian vertebrates (FIG. 1*f*).

The new MeCP2 N-terminus is a distinctive 21 amino acid peptide including polyalanine and polyglycine tracts (MAAAAAAAPSGGGGGGEEERL) (SEQ ID No. 18) (FIG. 1*f*). A similar N-terminus occurs in the ERK1 (MAPK3) extracellular signal-regulated kinase (FIG. 1*f*), a key common component of multiple signal transduction pathways. Intriguingly, in neurons, both ERK1 and MeCP2 have been shown to be present in the post-synaptic compartment, in addition to the nucleus, and the former shown to translocate between the two compartments to link synaptic activity to transcriptional regulation. It is possible that MeCP2E1 similarly links synaptic function, in this case neurodevelopmental synaptic contact guidance, with transcriptional regulation. The only other proteins in which consecutive polyalanine and polyglycine tracts are found are in some members of the homeobox (HOX) family. These, like MeCP2, are developmental transcription regulators.

Finally, non-inactivating MECP2 mutations have been associated with phenotypes that overlap RTT such as mental retardation and autism. The MeCP2 variant discovered in this study is a candidate for involvement in these disorders.

Example 4

Mutations in MECP2E1 in Mental Retardation

Figure 5:
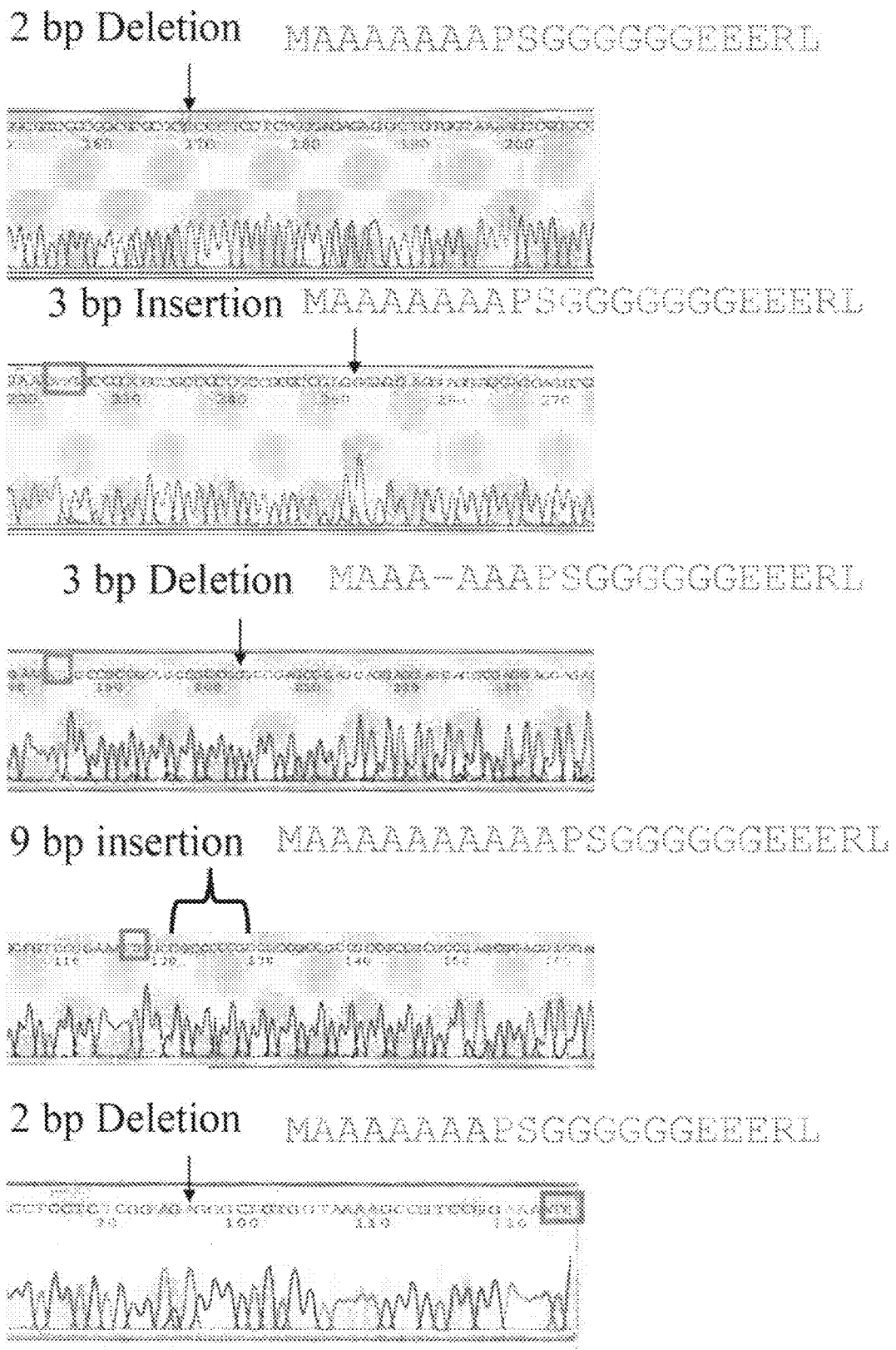
FIG. 5 shows the nucleotide sequence of the five MECP2 exon 1 variants identified in female MR patients. All sequences were obtained from single colonies, after cloning the heterozygous PCR product into the pDRIVE vector (Qiagen). The ATG start codon is indicated by a red box, where possible. The resulting amino acid sequence is also indicated, with wild type sequence shown in red, and changes indicated in green type.
Figure 6:
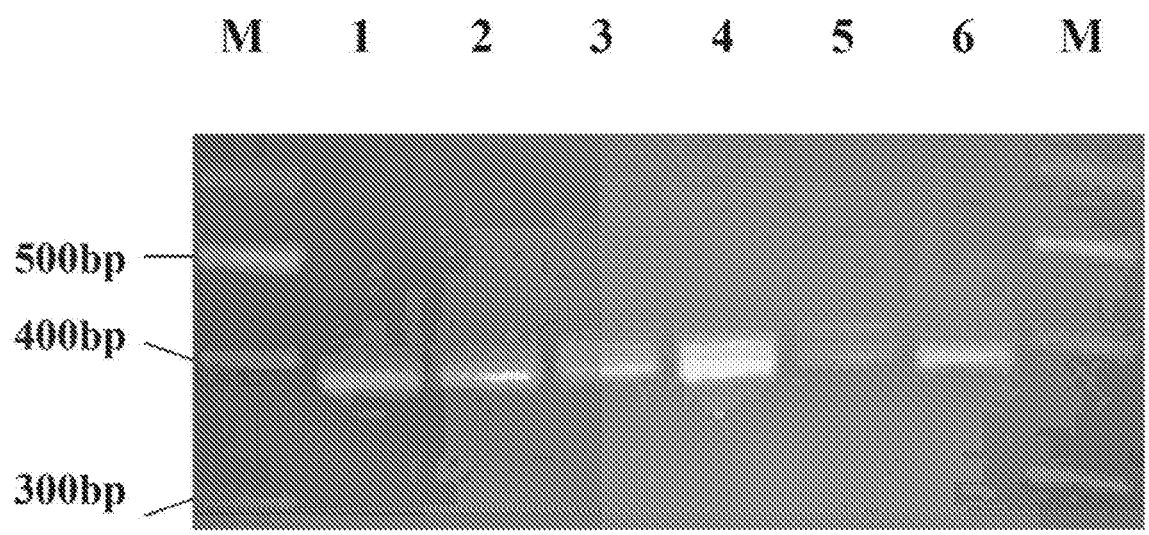
FIG. 6 shows a high resolution agarose gel (2.2%) of PCR product for MECP2 exon 1 for negative controls (Lanes 1 and 2), 3 bp insertion (Lanes 3 and 4), 9 bp insertion (Lane 5) and 2 bp deletion (Lane 6). Size ladder (M)100 bp ladder (MBI Fermentas), flanks the PCR lanes.

The inventors screened the MECP2E1 gene in N=401 autism probands, and in N=493 patients with non-specific mental retardation. Autism probands recruited through the Hospital for Sick Children in Toronto (N=146; 114 male, 32 female) and from London, UK (N=13; 10 male, 3 female) were also screened, as well as probands from multiplex families from the Autism Genetic Resource Exchange (AGRE; N=242; 100 female, 142 male). Local institutional ethics board approval was obtained, and written consent given by participants. Anonymized DNA samples were also obtained for 293 female and 200 male patients with non-specific developmental delay/mental retardation who had been referred for fragile-X testing (but tested negative) to the Department of Pediatric Laboratory Medicine at the Hospital for Sick Children. Polymerase chain reaction followed by denaturing high performance liquid chromatography (DHPLC) was used for mutation detection, with PCR primers and conditions as described previously in Example 3. PCR product from female individuals suspected of carrying a sequence variant was cloned into the pDRIVE vector (Qiagen), and at least four clones sequenced using automated BIGDYE™ Terminator v3.1 Cycle Sequencing Kit (ABI 3100) in forward and reverse directions. PCR products from males were excised from agarose gel, column purified, then sequenced, also using automated BIGDYE™ Terminator v3.1 Cycle Sequencing Kit (ABI 3100) in both forward and reverse directions. No mutations were identified among the autism screening set, however sequence variants were identified among eight of the female MR cases (see FIG. 5), three of which result in insertion or deletion of amino acids within the polyalanine repeat stretch, and two of which result in insertion of a glycine residue within the polyglycine repeat at the N-terminal portion of MECP2E1. The first individual identified was heterozygous for a deletion of a GpC dinucleotide positioned 45-46 bp upstream of the putative MECP2E1 start codon. This deletion could disrupt a potential SP1 transcription factor binding site (as predicted using AliBaba2.1 www.gene-regulation.com/pub/programs/alibaba2/index.html), and may also eliminate potentially methylatable cytosine residues. Another individual is heterozygous for an ApG dinucleotide deletion 26 bp upstream of the MECP2E1 start codon. Two individuals are heterozygous for a GGA trinucleotide insertion within a poly[GGA] stretch, which would result in an additional glycine residue within the predicted polyglycine stretch. A fifth individual is heterozygous for a GCC trinucleotide deletion within a triplet repeat stretch encoding polyalanine. Two individuals are heterozygous for a 9 bp insertion, also within the GCC trinucleotide repeat/polyalanine region, and would result in the polyalanine stretch being extended from seven to ten residues.

The amino acid sequence variation in ~2% of female non-specific MR cases in a new isoform of a protein that has previously been associated with a mental retardation syndrome, is extremely intriguing. Moreover, the fact that the variation occurs within a part of the protein that is conserved across many vertebrate species also adds to the interest (100% identity to chimpanzee, orang-utan, macaque, cat and dog MeCP2E1 amino acid sequence). It would be particularly useful to know whether there are any specific phenotypic features among the individuals with the variants, how severe the symptoms are an whether there are overlaps with or distinctions from the Rett syndrome phenotypes. However, since the DNAs were anonymized, it is not possible, in this instance, to correlate the mutations discovered with phenotypic features or severity. In an attempt to address this issue, a second sample set of MR cases (188 female and 96 male) from the Greenwood Genetic Center, S.C., were screened, followed by sequencing. No variants were found in the males, and two of the females carried the GGA insertion encoding an extra glycine residue.

In the present study, three female MR patients were identified with a 3 bp insertion leading to an extra glycine residue within the polyglycine stretch at the N-terminal end of MeCP2E1. No disease association has previously been reported with expansion within a glycine repeat. The function of polyglycine stretches, either within the context of the MeCP2E1 protein or more generally, is not known, although a study of the Toc75 protein in plants suggests that a polyglycine stretch in the protein is essential for correct targeting of the protein to the chloroplast outer envelope. A similar function of protein trafficking may also be the case for mammalian proteins with polyglycine stretches, and for MeCP2E1.

The variants within the polyalanine tracts are of particular interest, as they are rarely polymorphic, and because a number of small expansions (or duplications) within such tracts have been reported to cause diseases, ranging from cleidocranial dysplasia (RUNX2), oculopharyngeal muscular dystrophy (PABPN1) and mental retardation (ARX; this gene is also X-chromosomal and has a very broad array of phenotypes—see above). The majority of polyalanine disease genes encode transcription factors, although PABPN1 gene encodes a polyadenylate binding protein. On the one hand, amongst these diseases, the smallest pathogenic repeats within the transcription factor genes are generally greater than 20 alanines in length, thus it could be considered improbable that a stretch of alanines as short as that encoded by MECP2E1 could be pathogenic, and a change of 1 or 3 alanine residues could be considered likely to be rare polymorphisms. There is currently some uncertainty as to whether small expansion of 1 or 3 alanine residues within the ARX gene may be pathogenic or innocent variants. On the other hand, oculopharyngeal muscular dystrophy is caused by mutations within a GCG tract in the PABPN1 gene, that expand a polyalanine tract from just 10 alanine residues to between 12 and 17 alanine residues. Moreover, as with the polyalanine tract in MeCP2E1, the polyalanine tract in PABPN1 is right at the N-terminal end of the gene, and thus it is possible that smaller mutations within repeat stretches within the N-terminal portion of a protein may be more detrimental than larger mutations located in the central portions of proteins.

A recently published study screened for mutations in MECP2 exon 1 among 97 Rett patients with no mutation in exons 2, 3 or 4, and among 146 controls. One of the Rett patients was found to have a 6 bp insertion within the polyalanine-encoding [GCC] stretch, but no such variations were observed among the controls. The variant was inherited from an unaffected mother, and it was concluded that the variant is thus unlikely to be etiologically relevant. However, it has also been demonstrated recently that even subtle changes in expression of MECP2 in mice can have profound neurological and behavioural consequences. It is apparent that patients with the same MECP2 mutation may have very different phenotypic features and severity, and it is likely that variation in X-inactivation pattern plays a role in this discordancy. Thus it is quite feasible that variation in exon 1, either within the repeat stretches resulting in change in length of polyalanine or polyglycine stretch, or in the region just upstream of the start codon, may affect function or expression levels resulting in a neuropathological phenotype.

Example 5

Additional Mutations in MECP2E1 in Rett's Syndrome

The entire coding regions of exons 1,2,3 and 4 and their intronic flanking sequences were analyzed. Exons 2 to 4 were amplified by PCR with primer pairs designed with the use of genomic sequence information from the Human Genome Project working draft site (UCSC, www.genome.ucsc.edu) and the Lasergene Primer select program. The PCR products were loaded on 2% agarose gel to confirm amplification before analysis for base changes by dHPLC (WAVE Nucleic Acid Fragment Analysis System from Transgenomic, San Jose, Calif.). Solvent A consisted of 0.1 mol/L triethylammonim acetate (TEAA) and 25% acetonitrile and solvent B contained 1M TEAA, 25% acenonitril. PCR products showing a chromatographic variation on dHPLC were sequenced directly on an automatic sequencer (Gene Reader 4200). The sequencing data was analyzed using DNA Star software SeqMan (Lasergene). Exon 1 was PCR amplified and sequenced in all patients as recently described.

The first exon 1 mutation consists of two missing base pairs at the exon 1 intron 1 boundary. Because of the nature of the sequence in this region, we cannot resolve whether the missing two nucleotides are the first two base pairs of intron 1 (GT) or the last nucleotide of exon 1 (T) and the first nucleotide of intron 1 (G). In either case, the missing pair of nucleotides destroys the predicted consensus splice site and results in readthrough of intron 1 (data not shown). In the second patient with an exon 1 mutation a 1A→T substitution (ATG->TTG) changes the first Methionine codon into a Leucine. The prediction is that MECP2E1 translation would be greatly or totally hindered due to absence of a start codon. MECP2E2 would be normally made (and appears unable to rescue the disease phenotype).

Example 6

Additional Mutations in MECP2E1 in Rett's Syndrome Patients

Thirty-five samples from females were referred to Children's Mercy Hospital for RTT testing in a two year period spanning September of 2004 through September of 2006 (See, for example, Saunders, C. J., et al., "Novel Exon 1 Mutations in MECP2 Implicate Isoform MeCP2_e1 in Classical Rett Syndrome," *American Journal of Medical Genet-*

*ics*, 149A: 1019-1023 (2009)). These patients had various clinical presentations, including autism, mental retardation, developmental delay, and "Angelman-like", and only 9 patients fit the criteria for classical (N=7) or variant (N=2) RTT. Permission to review patient charts was obtained through the Children's Mercy Hospitals and Clinics' Institutional Review Board. In addition, 16 female patients were ascertained through either the Hospital for Sick Children or Centre for Addiction and Mental Health in Toronto, either with autism and developmental delay (N=14) or Rett syndrome (N=2). This ascertainment was subsequent to the study reported by Mnatzakanian, G. et al., "A previously unidentified MECP2 open reading frame defines a new protein isoform relevant to Rett syndrome," *Nat Genet.*, 36: 339-341 (2004) and there is no overlap of subjects between that and the current study. Screening for mutations in MECP2 identified four patients with mutations involving exon 1.

Patient 1 was a 20-year-old at the time of testing who had a long standing clinical diagnosis of RTT but had never undergone confirmatory DNA testing. She met the criteria for classical RTT, with the exception of acquired microcephaly (head circumference is at 15%). Following normal perinatal development, she sat at 6 months, walked at 14 months, used simple words at 18 months, around which time she began to regress. She lost all speech in addition to purposeful hand movements, which were replaced by a sifting activity. She now walks with a shuffling gait, exhibits some aggressive behavior, is nonverbal, and has medically intractable epilepsy.

Patient 2 was 7 years old at the time of testing. She met the criteria for classical RTT, with the exception of acquired microcephaly (head circumference 50%). She had a period of normal development, such as smiling, rolling over, and sitting at appropriate times, but around 10 months she exhibited global developmental delay. There was no clear regression in her skills at that point. Around the age of 2, she developed a stereotypic midline hand movement involving her left hand in her mouth and her right hand twirling her hair or rubbing her hair between her fingers. She commando crawls for mobility and will take steps with assistance. She is very hirsute and has precocious puberty with pubic hair development beginning at age 5. She has episodic seizures that do not require daily medication. She had previously tested negative for MECP2 mutations in exons 2-4, MECP2 duplications and deletions, and research testing involving sequencing of the MECP2 promoter region. The family came to the clinic in pursuit of mutation screening for the cyclin-dependent kinase-like 5 (CDKL5) gene, but upon closer examination of the patient's medical record, it was discovered that exon 1 of MECP2 had not been sequenced.

Patient 3 was a 16-year-old female with a clinical diagnosis of Rett syndrome since 20 months of age. She had microcephaly, developmental regression, severe cognitive insufficiency, midline hand movements, general tonic-clonic seizure disorder, loss of gait, diffuse hypertonicity, scoliosis treated with surgery, GE reflux requiring gastrostomy tube, and multiple hospitalizations for bacterial pneumonia. On her last admission for pneumonia, she succumbed to respiratory insufficiency and was not resuscitated. Brain autopsy showed microencephaly, subpial gliosis, minimal loss of Purkinje cells with gliosis, and isolated eosinophilic neurons in the dentate nucleus and brain stem. Previous testing for MECP2 exons 2-4 was negative.

Patient 4 had a clinical diagnosis of Rett syndrome since age 10. At birth, she had a normal head circumference but poor muscle tone. Global developmental delays, intense eye contact and screaming spells were noted in infancy. Teeth grinding, hand flapping, and deterioration in fine motor skills began from age 3 to 4. Speech development was slow but she acquired a vocabulary of about 25 words before the onset of loss of speech at age 6 and she became non-verbal by age 10. She first walked at age 14 months following intensive physiotherapy, and still walks unassisted despite occasional loss of balance due to mild gait dyspraxia. Other significant medical history included scoliosis (treated with surgery) and chronic constipation. There is no history of seizures or acquired microcephaly. When the patient was 28 years old, the family sought molecular genetic testing to confirm the clinical diagnosis of Rett syndrome.

Research ethics board approval was obtained for the study, and written consent obtained for the four patients described here.

Sequence Analysis

DNA from blood, or in the case of patient 3, cultured fibroblast cells, was extracted by a manual salting out procedure (Lahiri, D. K. and Nurnberger, J. I., "A rapid non-enzymatic method for the preparation of HMW DNA from blood for RFLP studies," *Nucleic Acids Res.*, 19: 5444 (1991)). For most of the 35 subjects the entire MECP2 coding region (exons 1-4) was analyzed (primers and PCR conditions available upon request); for Patients 2 and 3, only exon 1 was analyzed since the remaining coding region had been previously tested by an outside laboratory. Exon 1 of the MECP2 gene was PCR-amplified as described previously (Mnatzakanian, G. et al., "A previously unidentified MECP2 open reading frame defines a new protein isoform relevant to Rett syndrome," *Nat Genet.*, 36: 339-341 (2004)) and verified on a 2% agarose gel. Fragments were purified using ExoSAPit (USB Corp., Cleveland Ohio). Purified products were sequenced in both forward and reverse directions by automated fluorescent dye-terminator sequencing using Big Dye v3.0 (Applied Biosystems, Foster City, Calif.) and run on an ABI310 (Applied Biosystems). For Patient 2, allele-specific sequence was obtained after cloning the heterozygous PCR product into a TA cloning vector (Invitrogen, Carlsbad, Calif.). The sequence data was compared to the MECP2 reference sequence AF030876 using Sequencher software (Gene Codes, Ann Arbor, Mich.).

In silico analysis of efficiency of translation start sites affected by exon 1 mutations was performed on MEPC2 mRNA sequences using NetStart (www.cbs.dtu.dk/services/NetStart).

X-chromosome Inactivation

X-chromosome inactivation was assessed on genomic DNA from peripheral blood leukocytes by methylation-sensitive restriction digestion followed by PCR amplification across the androgen receptor [CAG] repeat region, according to the method described by Plenge, R. M. et al., "Skewed X-chromosome inactivation is a common feature of X-linked mental retardation disorders," *Am J Hum Genet.*, 71: 168-173 (2002).

Results

In 51 samples tested for RTT, four unrelated patients with exon 1 mutations were identified.

In Patient 1, a mutation was detected, c.1A>T in SEQ ID No. 1 that disrupts the initiation codon, changing it to a leucine. SEQ ID No. 1 contains non-coding exon sequence upstream of the start codon, so the mutation is located at position 8 in SEQ ID No. 1 which corresponds to the first position in the coding exon of SEQ ID No. 1. In silico analysis of translation initiation using NetStart predicts that translation of MeCP2_e1 would be ablated, but without any negative affect on translation of MeCP2_e2. The patient's mother tested negative for this mutation, however the father's DNA was not available for testing. X-chromosome inactivation in peripheral blood leukocytes appeared to be random.

Patient 2 has a mutation, c.62+1delTG in SEQ ID No. 1, affecting the splice donor (Amir, R. E. et al., "Mutations in exon 1 of MECP2 are a rare cause of Rett syndrome," *J Med Genet.*, 42: e15 (2005)). SEQ ID No. 1 contains non-coding exon sequence upstream of the start codon, so the mutation is located at positions 69 and 70 in SEQ ID No. 1 which corresponds to positions 62 and 63 in the coding exon of SEQ ID No. 1. Analysis of parental DNA revealed that it arose as a de novo mutation, not present in either parent. This mutation is predicted to disrupt splicing of the MECP2E1 mRNA, and may also affect the translation of the MeCP2_e2 isoform from the exon 2-containing mRNA, MECP2E2 (Amir, R. E. et al., "Mutations in exon 1 of MECP2 are a rare cause of Rett syndrome," *J Med Genet.*, 42: e15 (2005) and Saxena, A. et al., "Lost in translation: translational interference from a recurrent mutation in exon 1 of MECP2," *J Med Genet.*, 43: 470-477 (2006)). This patient had a random pattern of X-chromosome inactivation in peripheral blood leukocytes.

Patient 3 had a C>T transition (c.5C>T) in SEQ ID No. 1 resulting in a missense mutation, A2V. SEQ ID No. 1 contains non-coding exon sequence upstream of the start codon, so the mutation is located at position 12 in SEQ ID No. 1 which corresponds to the fifth position in the coding exon of SEQ ID No. 1. Though an alanine to valine substitution is conservative in retaining a nonpolar side chain, this is a residue that is perfectly conserved throughout evolution and marks the beginning of a polyalanine stretch which is present in all vertebrate species (Harvey, C. G. et al., "Sequence Variants Within Exon 1 of MECP2 Occur in Females With Mental Retardation," *Am J Med Genet (Neuropsychiatr Genet)*, 144: 355-360 (2007)). Though the role of this repeat is unknown, it contains multiple binding sites for the SP1 transcription factor, the alterations of which would affect the rate of gene transcription. This patient's parents both tested negative for this mutation, indicating this is a de novo mutation.

Patient 4 had a A>G transition (c.1 A>G) in SEQ ID No. 1 resulting in the start methionine codon being substituted by a valine codon. SEQ ID No. 1 contains non-coding exon sequence upstream of the start codon, so the mutation is located at position 8 in SEQ ID No. 1 which corresponds to the first position in the coding exon of SEQ ID No. 1. Both parents were negative for this mutation. As with Patient 1, this mutation is predicted to ablate translation of MeCP2_e1, but without any negative affect on translation of MeCP2_e2. X-chromosome inactivation in peripheral blood leukocytes showed skewing, 90:10.

The presence of these missense/start codon mutations in classic Rett patients, uniquely affecting the MeCP2_e1 isoform, clearly indicates the importance of this isoform in the etiology of Rett syndrome. None of these sequence changes were identified in a previous study that screened MECP2 exon 1 in 1,811 subjects with developmental delay or autism, and 498 healthy adult control individuals (Harvey, C. G. et al., "Sequence Variants Within Exon 1 of MECP2 Occur in Females With Mental Retardation," *Am J Med Genet (Neuropsychiatr Genet)*, 144: 355-360 (2007)).

Discussion

MECP2 was sequenced in 51 females with various clinical presentations, including developmental delay, autism, atypical and classical RTT, referred to the laboratory for testing. In patients with identified mutations, X-chromosome inactivation was analyzed. Four patients were identified with exon 1 mutations (c.1A>T; c.1A>G; c.5C>T), two of which affected the start codon, one a missense change, and one patient had a previously reported splice site mutation, c.62+1delGT. The 4 patients fit criteria for classical RTT, and thus these findings add support to previous reports that exon 1 mutations may be associated with a severe phenotype. Also, these findings add significant weight to the mounting evidence suggesting that the MeCP2_e1 isoform is the etiologically relevant form of the protein.

As discussed above, three mutations were detected within exon 1 of the MECP2 gene in 35 clinical samples referred to CMH for MECP2 sequencing, and in one out of 16 samples from the Toronto patient set. All four were associated with classical RTT. Two of these patients had previously tested negative by molecular testing, which at the time included sequencing of exons 2-4 of the MECP2 gene. Following the reports of the second MeCP2 isoform (MeCP2_e1) and the clinical utility of sequencing exon 1, these patients were tested for exon 1 mutations. The total number of distinct exon 1 mutations detected by sequencing is now 10. Two of these mutations, c.47_57del11nt and c.62+1delGT, have been found in more than one patient (see Table 2). This brings the number of Rett patients known to have a mutation within exon 1 of MECP2 to 14.

All mutations localized to exon 1 reported until recently have been either small insertions or deletions or large deletions removing the entire exon. The c.1A>T and c.1A>G mutations, which are single base pair changes, are the first point mutations to be reported in exon 1 of the MECP2 gene (also see Gauthier, J. et al., "Clinical stringency greatly improves mutation detection in Rett syndrome," *Can J Neurol Sci*, 32: 321-6 (2005)). The c.1A>T and c.1A>G mutations alter the initiation codon, which would mostly likely result in absent translation of MeCP2_e1. MeCP2_e2 would be presumably unaffected but is clearly unable to compensate, as evidenced by the patients' classic RTT symptoms. Patient 3 had a C>T transition (c.5C>T) resulting in a missense mutation, A2V. This alanine is a perfectly conserved residue that marks beginning of a polyalanine stretch that is present in all vertebrate species (Harvey, C. G. et al., "Sequence Variants Within Exon 1 of MECP2 Occur in Females With Mental Retardation," *Am J Med Genet (Neuropsychiatr Genet)*, 144: 355-360 (2007)). The role of this repeat is unknown, but it could play a role in the regulation of gene transcription, given the multiple binding sites for the SP1 transcription factor. This patient's parents both tested negative for this mutation, indicating this is a de novo, most likely pathogenic mutation. This also emphasizes the functional importance of the N-terminal portion of MeCP2_e1. There are a number of lines of evidence pointing to the likelihood that the MeCP2_e1 isoform is more relevant to RTT etiology than MeCP2_e2: a) no exon 2 missense mutations (which should only affect MeCP2_e2) have been identified to date; b) MeCP2_e1 is the predominant isoform expressed in neuronal tissues Kriaucionis, S. and Bird, A., "The major form of MECP2 has a novel N-terminus generated by alternative splicing," *Nucleic Acids Res*, 32: 1818-1823 (2004); Mnatzakanian, G. et al., "A previously unidentified MECP2 open reading frame defines a new protein isoform relevant to Rett syndrome," *Nat Genet.*, 36: 339-341 (2004)); c) MeCP2_e1 appears to be the ancestral form of the gene-MeCP2_e2 is only found among the higher vertebrates (Mnatzakanian, G. et al., "A previously unidentified MECP2 open reading frame defines a new protein isoform relevant to Rett syndrome," *Nat Genet.*, 36: 339-341 (2004) and Harvey, C. G. et al., "Sequence Variants Within Exon 1 of MECP2 Occur in Females With Mental Retardation," *Am J Med Genet (Neuropsychiatr Genet)*, 144: 355-360 (2007). On the other hand, analysis of the MECP2 exon 1 11 bp deletion (c.47_57del11nt (p.Gly16Glufs)) identified in a number of studies (Mnatzakanian, G. et al., "A previously unidentified MECP2 open reading frame defines a new protein isoform relevant to Rett syndrome," *Nat Genet.*, 36: 339-341 (2004); Amir, R. E. et al., "Mutations in exon 1 of MECP2 are a rare cause of Rett syndrome," *J Med Genet.*, 42: e15 (2005); Saxena, A. et al., "Lost in translation: translational interference from a recurrent mutation in exon 1 of MECP2," *J Med Genet.*, 43: 470-477 (2006); and Ravn, K. et al., "Mutations found within exon 1 of MECP2 in Danish patients with Rett syndrome," *Clin Genet.*, 67: 532-533 (2005)) has suggested that both isoforms of MeCP2 are disrupted in these patients, and thus could not exclude a role for MeCP2_e2 in RTT etiology (Saxena, A. et al., "Lost in translation: translational interference from a recurrent mutation in exon 1 of MECP2," *J Med Genet.*, 43: 470-477 (2006)). However, the missense and start codon mutations, where only MeCP2_e1 is likely disrupted, cast further doubt on a role for MeCP2_e2 in the disorder.

Previous studies have concluded that sequencing exon 1 contributes little to the mutation detection rate in RTT, even in pre-selected populations such as classical RTT patients who had already tested negative for mutations in exons 2-4 of the gene (Amir, R. E. et al., "Mutations in exon 1 of MECP2 are a rare cause of Rett syndrome," *J Med Genet.*, 42: e15 (2005); Evans, J. C. et al., "Variation in exon 1 coding region and promoter of MECP2 in Rett syndrome and controls," *Eur J Hum Genet.*, 13: 124-126 (2005); and Quenard, A. et al., "Deleterious mutation in exon 1 of MECP2 in Rett syndrome," *Eur J Med Genet.*, 49: 313-322 (2006)). However, the results of the study described herein, which spanned two years with a total of 51 female patients tested, a minority of whom met the clinical criteria for classical RTT (9) or variant RTT (2), were quite different. Other clinical presentations such as autism or developmental delay were much more frequent in this testing population, which would be less likely to be associated with a MECP2 mutation. Seven other studies examining the exon 1 mutation frequency in Rett females have been published to date (see Table 3). All of these studies were restricted to patients meeting criteria for classic or variant RTT and except for one study (Quenard, A. et al., "Deleterious mutation in exon 1 of MECP2 in Rett syndrome," *Eur J Med Genet.*, 49: 313-322 (2006)), all were looking at patients who had previously tested negative for mutations in exons 2-4. The detection rates for mutations within exon 1 range from 0% to 25% (See Table 3) in these studies, with several groups concluding that exon 1 mutations are a rare cause of RTT (Amir, R. E. et al., "Mutations in exon 1 of MECP2 are a rare cause of Rett syndrome," *J Med Genet.*, 42: e15 (2005); Evans, J. C. et al., "Variation in exon 1 coding region and promoter of MECP2 in Rett syndrome and controls," *Eur J Hum Genet.*, 13: 124-126 (2005); and Quenard, A. et al., "Deleterious mutation in exon 1 of MECP2 in Rett syndrome," *Eur J Med Genet.*, 49: 313-322 (2006)). In this study of 51 unselected patients, 4 had exon 1 mutations (7.8%). For the sake of comparison, if the numbers are restricted to only those patients who fit the classic or atypical RTT criteria, then the exon 1 mutation frequency is 36%. The average detection rate from the reports listed in Table 3 is 8.1% (median 5%). Taken together, these data indicate that exon 1 mutations detectable by sequencing are slightly more common than previously reported (Amir, R. E. et al., "Mutations in exon 1 of MECP2 are a rare cause of Rett syndrome," *J Med Genet.*, 42: e15 (2005); Evans, J. C. et al., "Variation in exon 1 coding region and promoter of MECP2 in Rett syndrome and controls," *Eur J Hum Genet.*, 13: 124-126 (2005); and Quenard, A. et al., "Deleterious mutation in exon 1 of MECP2 in Rett syndrome," *Eur J Med Genet.*, 49: 313-322 (2006)).

Although genotype-phenotype correlations are difficult to make in RTT because of differences in X-chromosome inactivation (XCI), several authors have observed that patients with exon 1 mutations result in a severe RTT phenotype (Amir, R. E. et al., "Mutations in exon 1 of MECP2 are a rare cause of Rett syndrome," *J Med Genet.*, 42: e15 (2005); Bartholdi, D. et al., "Clinical profiles of four patients with Rett syndrome carrying a novel exon 1 mutation or genomic rearrangement in the MECP2 gene," *Clin Genet.*, 69: 319-326 (2006); and Chunshu, Y. et al., "A patient with classic Rett syndrome with a novel mutation in MECP2 exon 1," *Clin Genet.*, 70: 530-531 (2006)). This could be because exon 1 mutations cause premature truncation of the more relevant, brain-dominant isoform (Kriaucionis, S. and Bird, A., "The major form of MECP2 has a novel N-terminus generated by alternative splicing," *Nucleic Acids Res*, 32: 1818-1823 (2004) and Mnatzakanian, G. et al., "A previously unidentified MECP2 open reading frame defines a new protein isoform relevant to Rett syndrome," *Nat Genet.*, 36: 339-341 (2004)).

Out of the 14 patients harboring mutations within exon 1, all but two had classic/severe RTT. The two patients with atypically mild RTT had the same c.47_57del11nt mutation, which has also been reported in classic RTT patients (Table 2), differences for which could be attributed to skewed XCI. All four of the patients in this study had classic RTT, with one dying at an early age from pneumonia at the age of 16. Although the numbers are too small to be of any statistical significance, it is worth noting that 4 of the 14 patients listed in Table 2 died by the age of 25 (median age 17.5). RTT patients do have a decreased survival compared to the general population, but survival to 20 years was 94% in a preliminary study of patients from Texas (del Junco, D. et al., "Survival in a large cohort of US girls and women with Rett syndrome," *J Child Neurol*, 8:101-102 (1993), Abstract.) and 85.3% in a large Australian cohort of 276 RTT patients (Laurvick, C. L. et al., "Rett syndrome in Australia: a review of the epidemiology," *J Pediatr*, 148: 347-352 (2006)).

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

MECP2E1 mutations or variants identified to date.

| Nucleotide change | Position relative to NM_004992 (SEQ ID No. 1) | Amino acid change | Effect of change | Associated phenotype | Number of Patients with mutation |
|---|---|---|---|---|---|
| 11 bp deletion | Between 38 to 54 | Frameshift leads to nonsense mutation, premature truncation of protein after amino acid 36 | MECP2E1 disrupted, MECP2E2 not disrupted | Rett | 1 |
| Exon 1 deletion | 1-69 | No MECP2E1 translation | MECP2E1 and MECP2E2 disrupted | Rett | 1 |
| 1A->T | 8 | 1Met->Leu | MECP2E1 disrupted, MECP2E2 possibly diminished | Rett | 1 |
| del[TG] | 69 to 70 | Destroys exon1/intron 1 splice site, resulting in read through and nonsense translation, with truncation after amino acid 97 | MECP2E1 disrupted, MECP2E2 probably not disrupted | Rett | 1 |
| ins[GCCGCCGCC] | Between nt 11 and 29 | ins[Ala]3 within N terminal polyalanine stretch of MECP2E1 | May affect function and or translation of MECP2E1, but not MECP2E2 | Developmental Delay | 2 |
| del[GCC] | Between nt 11 and 29 | del Ala within N terminal polyalanine stretch of MECP2E1 | May affect function and or translation of MECP2E1, but not MECP2E2 | Developmental Delay | 1 |
| ins[GGA] | Between 38 to 54 | ins Gly | May affect function and or translation of MECP2E1, but not MECP2E2 | Developmental Delay | 5 |
| −45 del [GC] | −38 to −39 relative to BX538060 | In 5'UTR, 45 nt upstream of START codon- potential SP1 transcription factor binding site | May affect transcription or translation of MECP2E1 | Developmental Delay | 1 |
| −26 del [AG] | −19 to −20 relative to BX538060 | In 5'UTR, 26 nt upstream of START codon | May affect transcription or translation of MECP2E1 | Developmental Delay | 1 |

"del" indicates a deletion;
"ins" indicates an insertion

TABLE 2

Summary of reported exon 1 sequence mutations in MECP2 to date.

| Mutation | Patient Age | Age at Death (Cause) | XCI | RTT Phenotype |
|---|---|---|---|---|
| c.1A>T (p.Met1?) | 20 | n/a | 63:37 | classic |
| c.1A>G (p.Met1?) | 28 | n/a | 90:10 | classic |
| c.5C>T (p.A2V) | | 16 (pneumonia) | Not done | classic |
| c.23_27dup5nt (p.Ser10Argfs) | | 25 (not given) | — | classic |
| c.30delCinsGA (p.Ser10Argfs) | | 19 (pneumonia) | 70:30 | classic |
| c.47_57del11nt (p.Gly16Glufs) | 27 | n/a | — | classic |
| c.47_57del11nt (p.Gly16Glufs) | 37 | n/a | — | classic |
| c.47_57del11nt (p.Gly16Glufs) | ? | n/a | 44:56 | atypical (mild) |
| c.47_57del11nt (p.Gly16Glufs) | 13 | n/a | 73:27 | atypical (mild) |
| c.48_55dup (p.Glu19Alafs) | 5 | n/a | Random | classic |
| c.59_60delGA (p.Arg20Thrfs) | 5 | n/a | 48:52 | classic |
| c.62+1delGT | 8 | n/a | 68:32 | classic |
| c.62+1delGT | 7 | n/a | 78:22 | classic |
| c.62+2_62+3del | | 6½ (not given) | Random | atypical (severe) |

TABLE 3

Literature reports of exon 1 mutation frequency in females with RTT and variant RTT phenotype.

| Frequency of Mutations in Exon 1 | Phenotype | Previously Negative for Exons 2-4 | Large Gene Rearrangements Including Exon 1 |
|---|---|---|---|
| 1/19; 5.2% | Typical RTT | Yes | 1 patient, exon 1 |
| 2/63; 3.2% | 38 classic RTT, 25 atypical RTT | Yes | Not tested |
| 2/212; .9% | 211 typical RTT, 1 atypical (severe) RTT | No | 4 patients, large deletions* |
| 2/10; 20% | Typical RTT | Yes | None |
| 1/20; 5% | 12 classic RTT, 8 variant RTT, | Yes | 1 patient, exons 1-2 |
| 1/20; 5% | Classic and atypical RTT | Yes | Not tested |
| 0/97; 0% | 37 classic RTT and 60 atypical | Yes | None (Not all were tested) |
| 1/4; 25% | Classic RTT | Not specified | n/a |
| 4/51; 7.8% | 9 classical RTT, 2 variant RTT; (the rest have autism, MR, microcephaly, etc.) | 21 Patients | Not tested |
| Total: 14/496; 2.8% | | | 6 Deletions |

*One deletion including promoter and exon 1, one including exons 1-2, one including promoter and exons 1-2, and one complete gene deletion

We claim:

1. A nucleic acid molecule comprising a fragment of a MECP2 sequence or the complementary sequence of the fragment, wherein the MECP2 sequence has the sequence of SEQ ID NO: 1, wherein the fragment comprises an adenine to thymine mutation at the nucleotide position corresponding to position 8 of SEQ ID NO: 1, and the complementary sequence of the fragment comprises a mutation complementary to the adenine to thymine mutation at the nucleotide position corresponding to position 8 of SEQ ID NO: 1; and
   wherein the nucleic acid molecule specifically binds under high stringency conditions to the MECP2 sequence comprising the mutation, and wherein the nucleic acid molecule is detectably labeled with a radioactive label, a fluorescent compound, an enzyme, or a chemiluminescent compound, and wherein the nucleic acid molecule is 15-50 nucleotides long.

2. The nucleic acid molecule of claim 1, wherein the nucleic acid molecule is 15-30 nucleotides long.

3. The nucleic acid molecule of claim 1, wherein the nucleic acid molecule is 15-25 nucleotides long.

4. A kit for detecting a mutation in MECP2 in a nucleic acid sample, comprising the nucleic acid molecule of claim 1.

5. The kit of claim 4, further comprising a reagent required for detecting the presence of the mutation in the MECP2 sequence.

6. The kit of claim 4, further comprising one or more primers selected from the group consisting of SEQ ID NOs: 5-9 and 19-20.

* * * * *